(12) United States Patent
Srouji

(10) Patent No.: US 11,839,747 B2
(45) Date of Patent: Dec. 12, 2023

(54) SYRINGE WITH DUAL NESTED CHAMBERS AND METHOD OF USE

(71) Applicant: MEDEVICENG, Nazareth Illit (IL)

(72) Inventor: Fares Srouji, Nazareth Illit (IL)

( * ) Notice: Subject to any disclaimer, the term of this patent is extended or adjusted under 35 U.S.C. 154(b) by 874 days.

(21) Appl. No.: 16/871,239

(22) Filed: May 11, 2020

(65) Prior Publication Data

US 2020/0338268 A1    Oct. 29, 2020

Related U.S. Application Data

(63) Continuation-in-part of application No. PCT/IL2018/051215, filed on Nov. 18, 2018.

(60) Provisional application No. 62/583,503, filed on Nov. 9, 2017.

(51) Int. Cl.
*A61M 5/19* (2006.01)
*A61M 1/16* (2006.01)
*A61M 39/10* (2006.01)

(52) U.S. Cl.
CPC .............. *A61M 5/19* (2013.01); *A61M 1/168* (2013.01); *A61M 39/10* (2013.01); *A61M 2039/1077* (2013.01)

(58) Field of Classification Search
CPC ........ A61M 5/19; A61M 1/168; A61M 39/10; A61M 2039/1077; A61M 2005/1787; A61M 2005/31598; A61B 5/150251
See application file for complete search history.

(56) References Cited

U.S. PATENT DOCUMENTS

| 2,939,459 A | 6/1960 | Lazarte |
| 3,010,705 A * | 11/1961 | Brown .............. B01F 33/50112 604/82 |
| 3,680,558 A | 8/1972 | Kapelowitz |
| 4,702,737 A | 10/1987 | Pizzino |
| 5,102,388 A | 4/1992 | Richmond |
| 5,181,909 A | 1/1993 | McFarlane |
| 5,372,586 A | 12/1994 | Haber |
| 5,489,267 A | 2/1996 | Moreno |

(Continued)

FOREIGN PATENT DOCUMENTS

| KR | 101763753 B1 | 8/2017 |
| WO | 2012006555 A1 | 1/2012 |
| WO | 2014165058 A1 | 10/2014 |

*Primary Examiner* — Laura A Bouchelle
*Assistant Examiner* — John A Doubrava
(74) *Attorney, Agent, or Firm* — ALPHAPATENT ASSOCIATES, LTD; Daniel J. Swirsky

(57) ABSTRACT

A nested syringe comprising: a first chamber comprising: an inner tube extending from a base of the first chamber and defining a base opening in the base; an adapter tube in fluid communication with the inner tube via the base opening; at least one base port in the base for providing fluid communication between the adaptor tube and a first inner volume of the first chamber; a second chamber, adapted for insertion into the first chamber wherein the second chamber comprises a third port adapted to provide fluid communication between the inner tube and a second inner volume of the second chamber and adapted for preventing fluid communication between the first inner volume and the second inner volume when the second chamber is inserted into the first chamber and the inner tube penetrates the third port; and a plunger, wherein the plunger is adapted for insertion into the second chamber.

9 Claims, 69 Drawing Sheets

(56) References Cited

U.S. PATENT DOCUMENTS

| | | | |
|---|---|---|---|
| 5,569,193 | A | 10/1996 | Hofstetter |
| 5,599,312 | A | 2/1997 | Higashikawa |
| 5,772,665 | A | 6/1998 | Glad |
| 5,785,682 | A | 7/1998 | Grabenkort |
| 6,723,074 | B1 | 4/2004 | Halseth |
| 8,353,866 | B2 | 1/2013 | Evans, Jr. |
| 8,936,577 | B2 | 1/2015 | Lee |
| 9,155,495 | B2 | 10/2015 | Bullington et al. |
| 10,369,285 | B2 * | 8/2019 | Hopkins .......... A61B 5/150221 |
| 10,576,205 | B2 | 3/2020 | Saab |
| 10,835,674 | B2 | 11/2020 | Cowan |
| 2010/0082015 | A1 * | 4/2010 | Chebator ............... A61M 5/284 |
| | | | 604/533 |
| 2010/0228121 | A1 | 9/2010 | Kazuhiro |
| 2010/0286513 | A1 | 11/2010 | Pollard, Jr. |
| 2015/0190576 | A1 | 7/2015 | Lee |
| 2018/0214876 | A1 * | 8/2018 | Muldoon ......... A61B 5/150992 |

\* cited by examiner

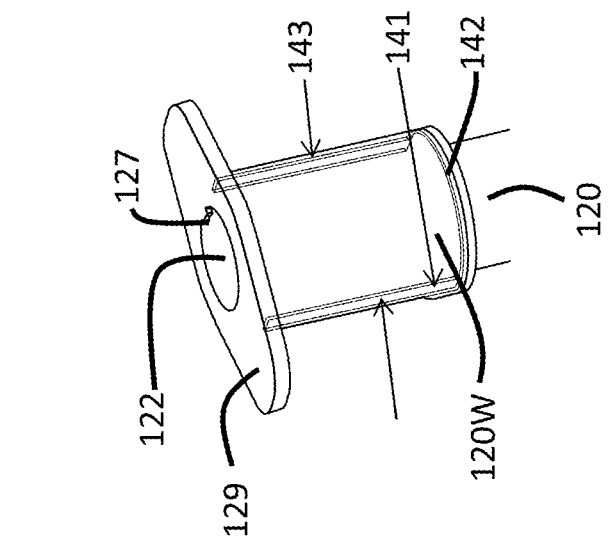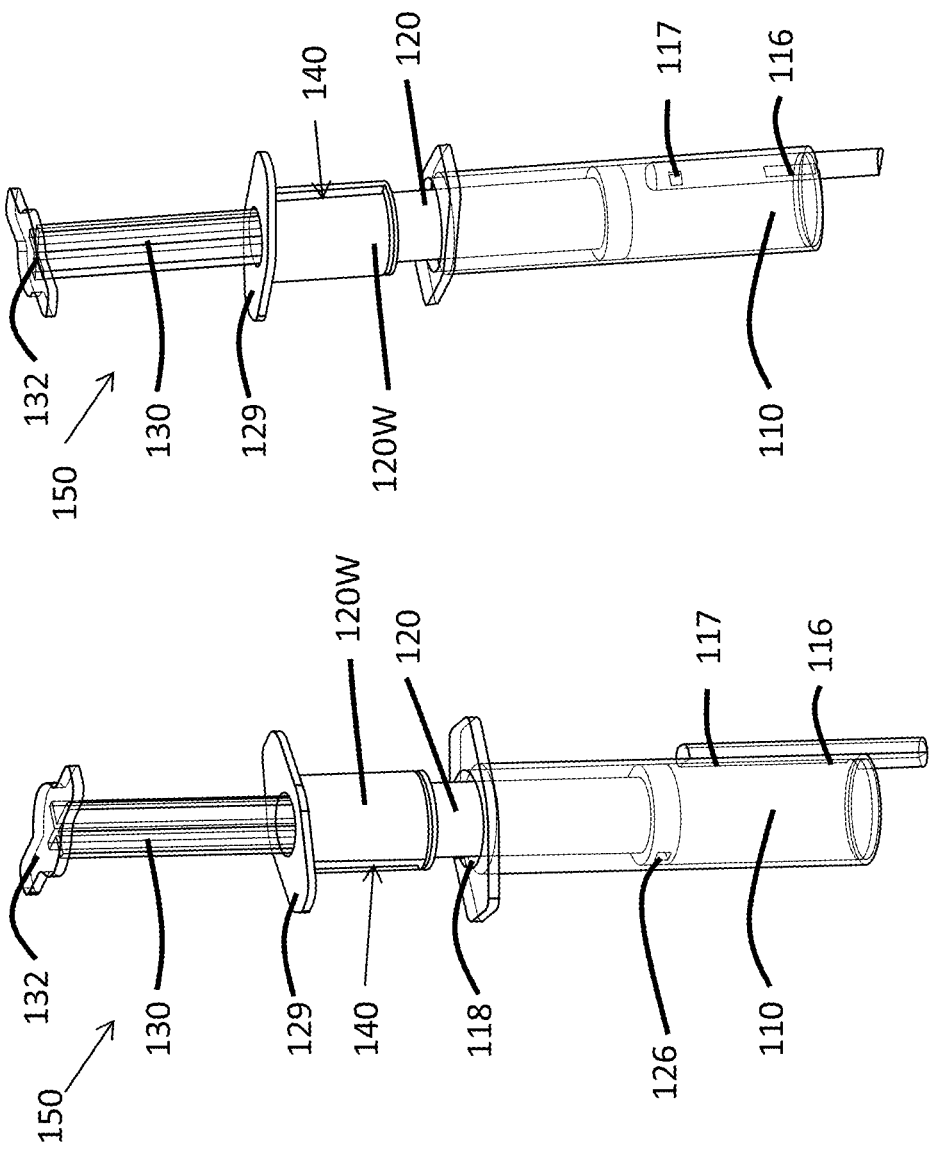

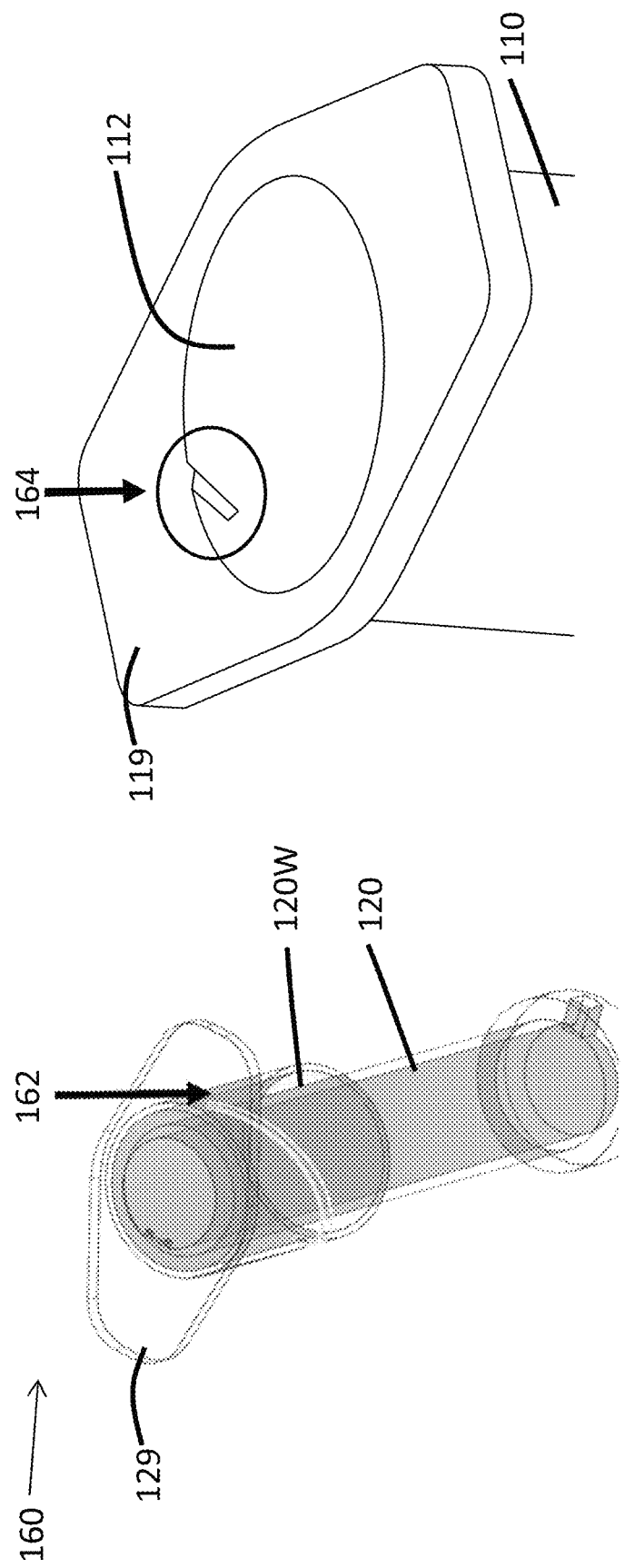

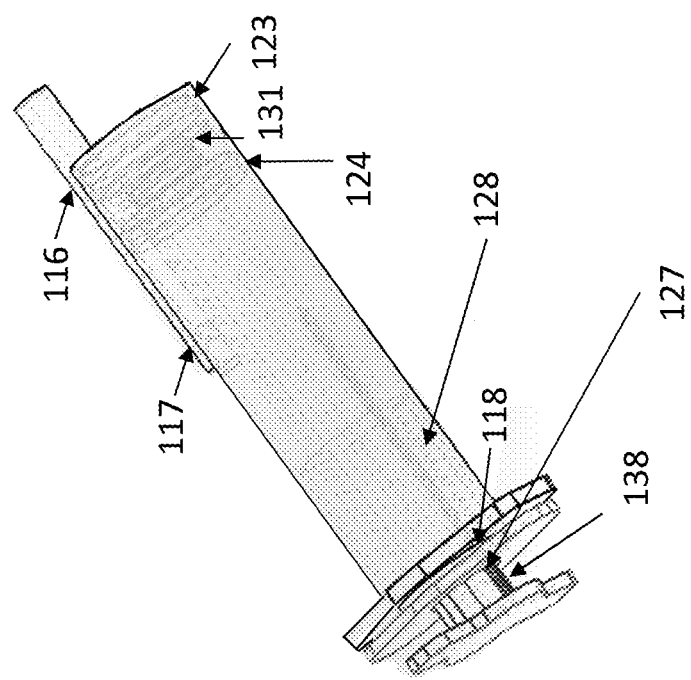

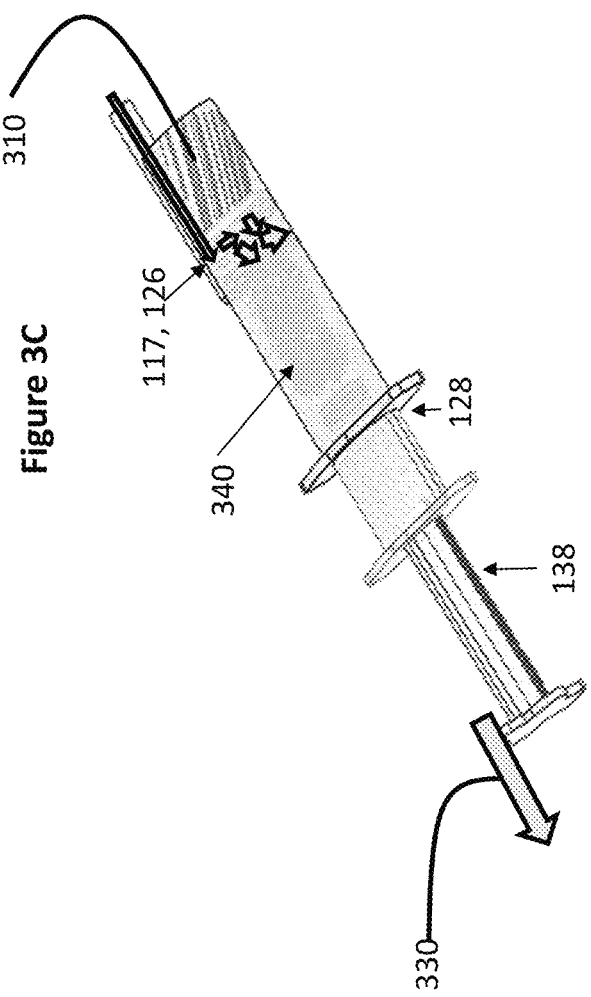

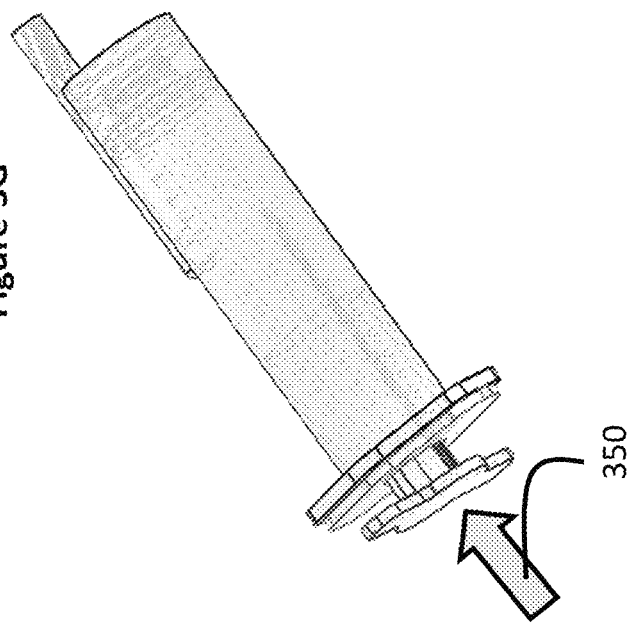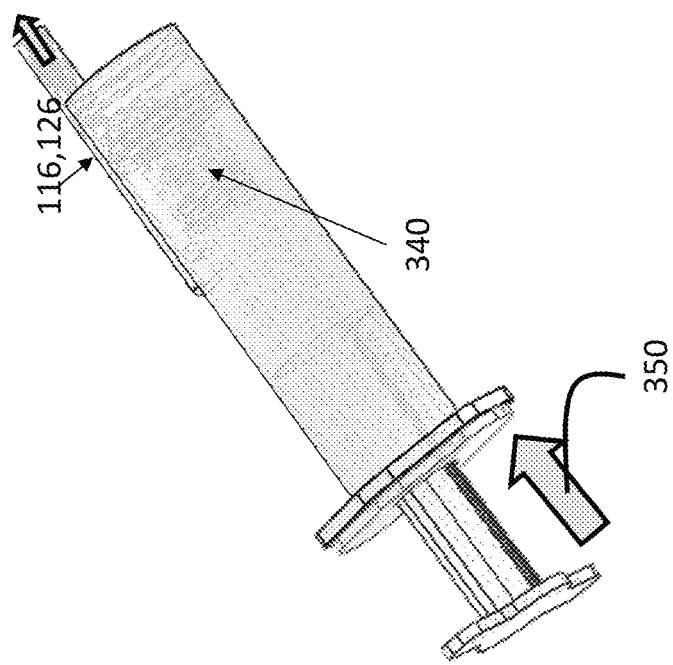

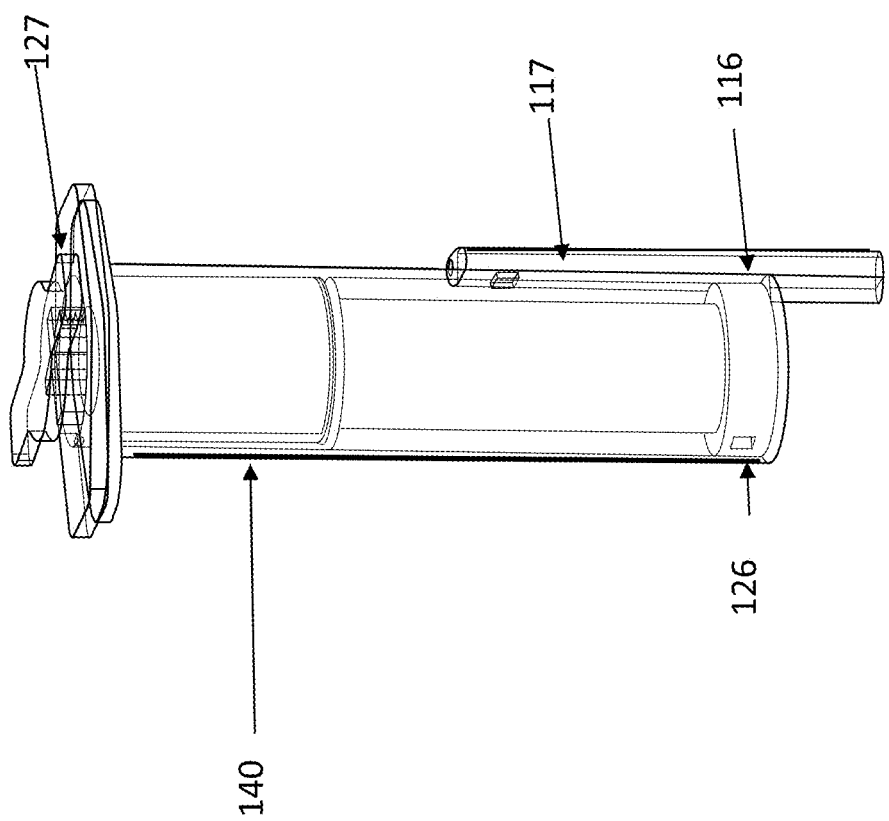
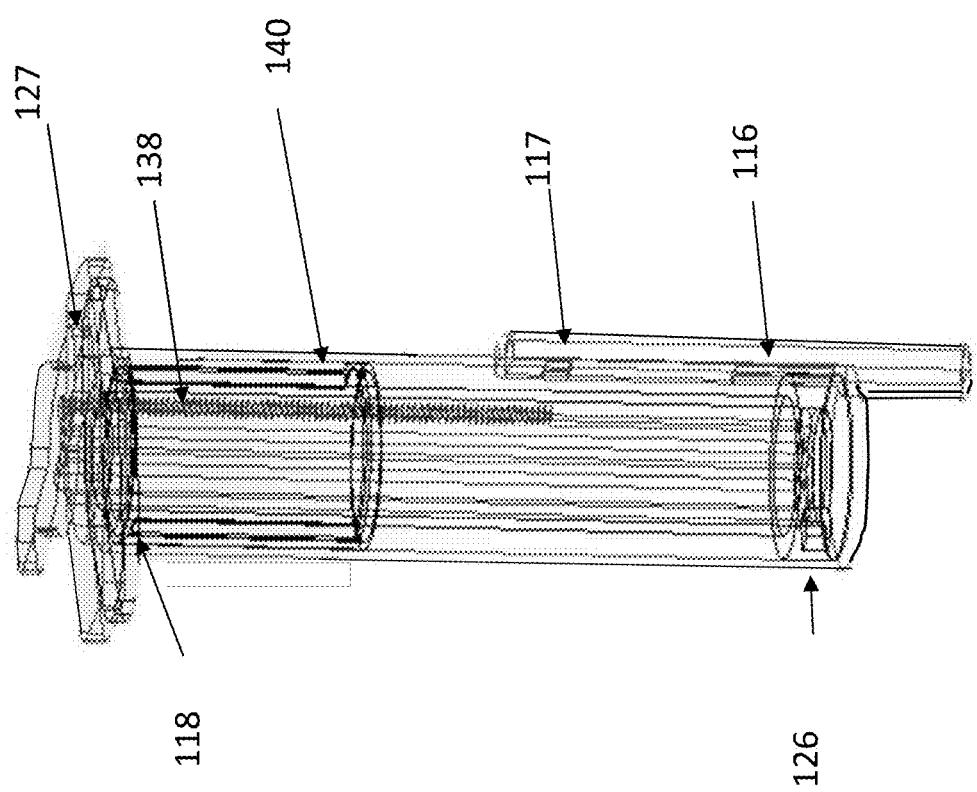

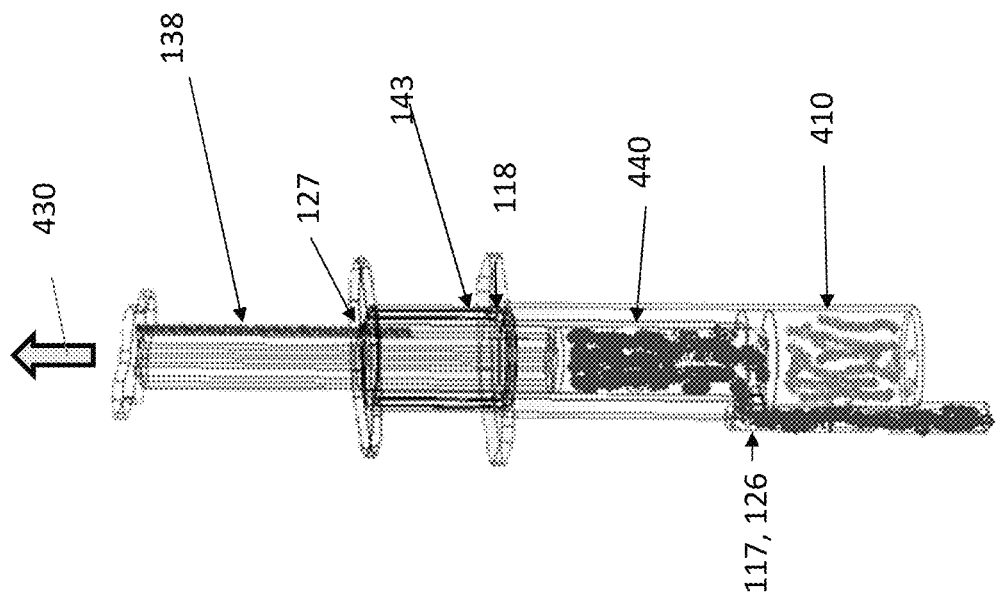

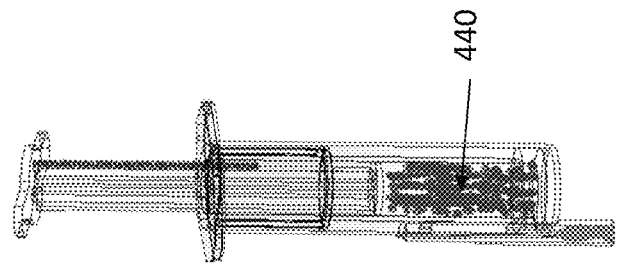
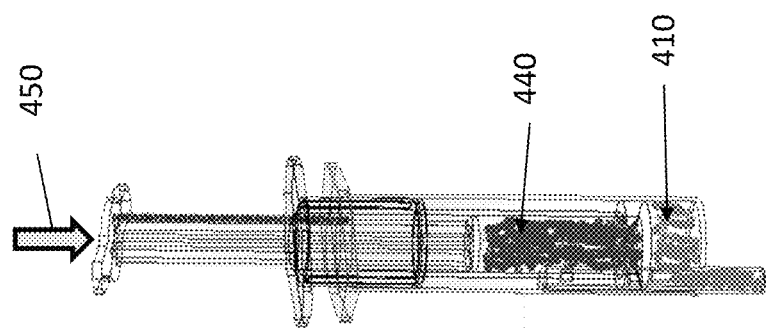
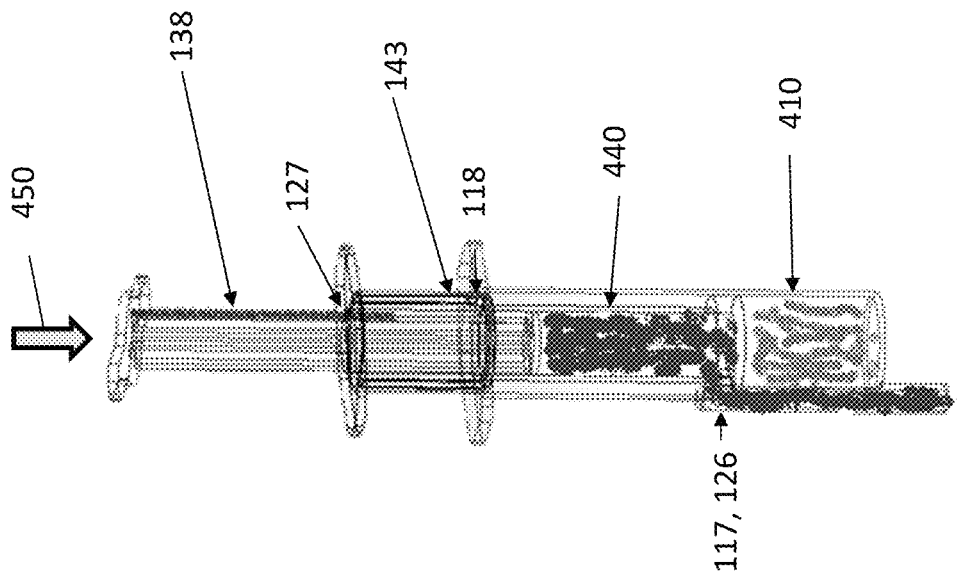

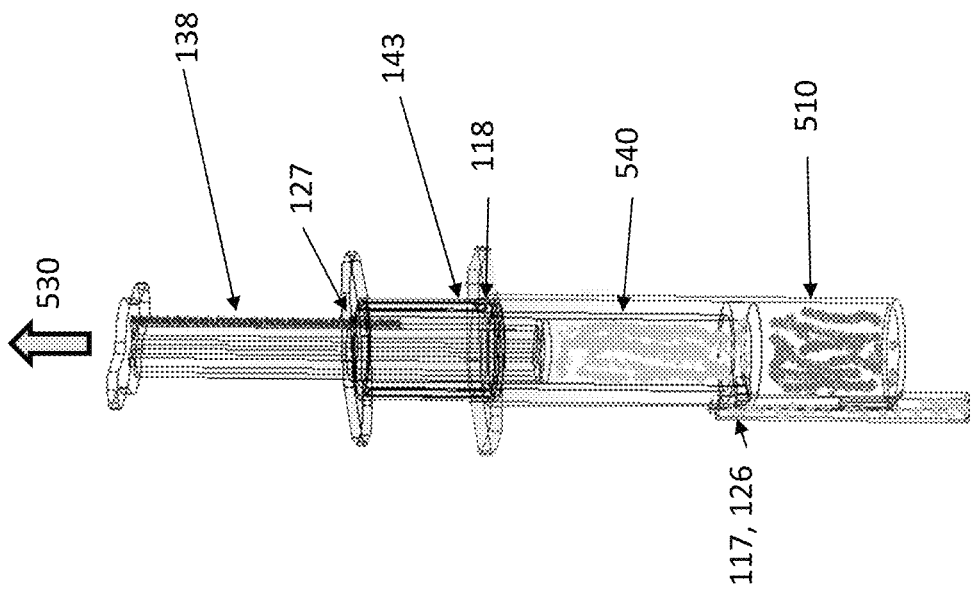

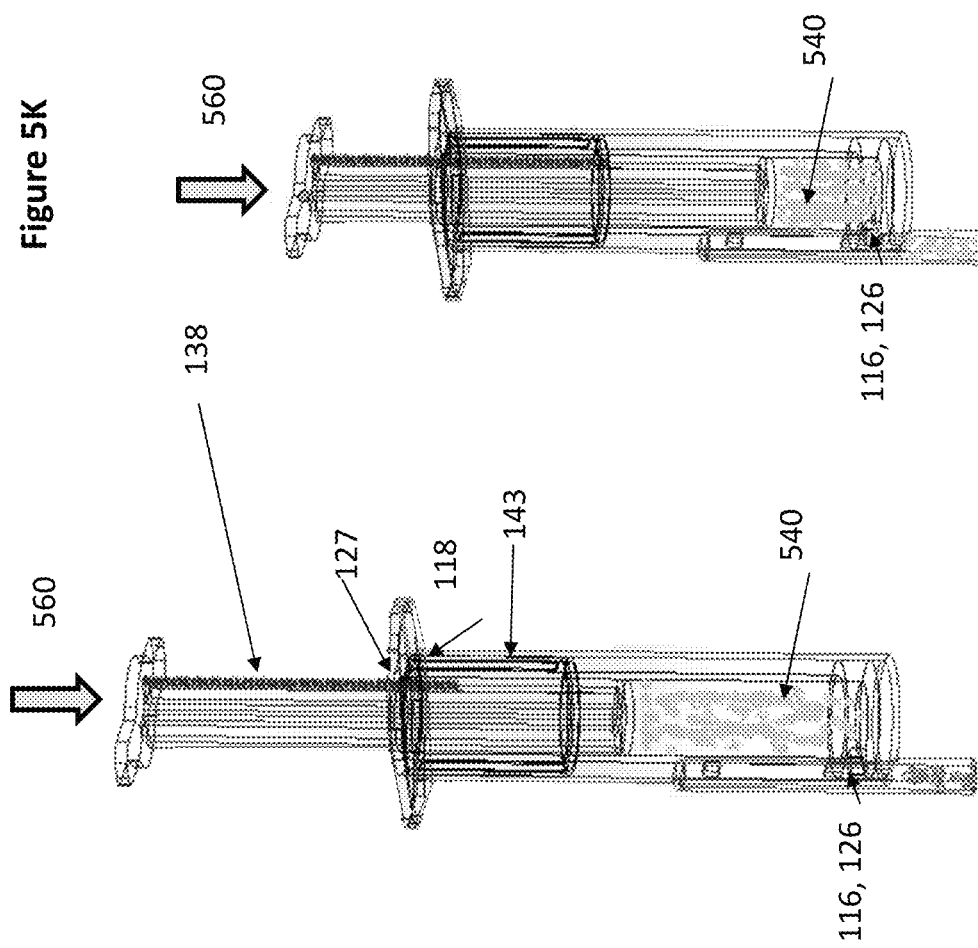

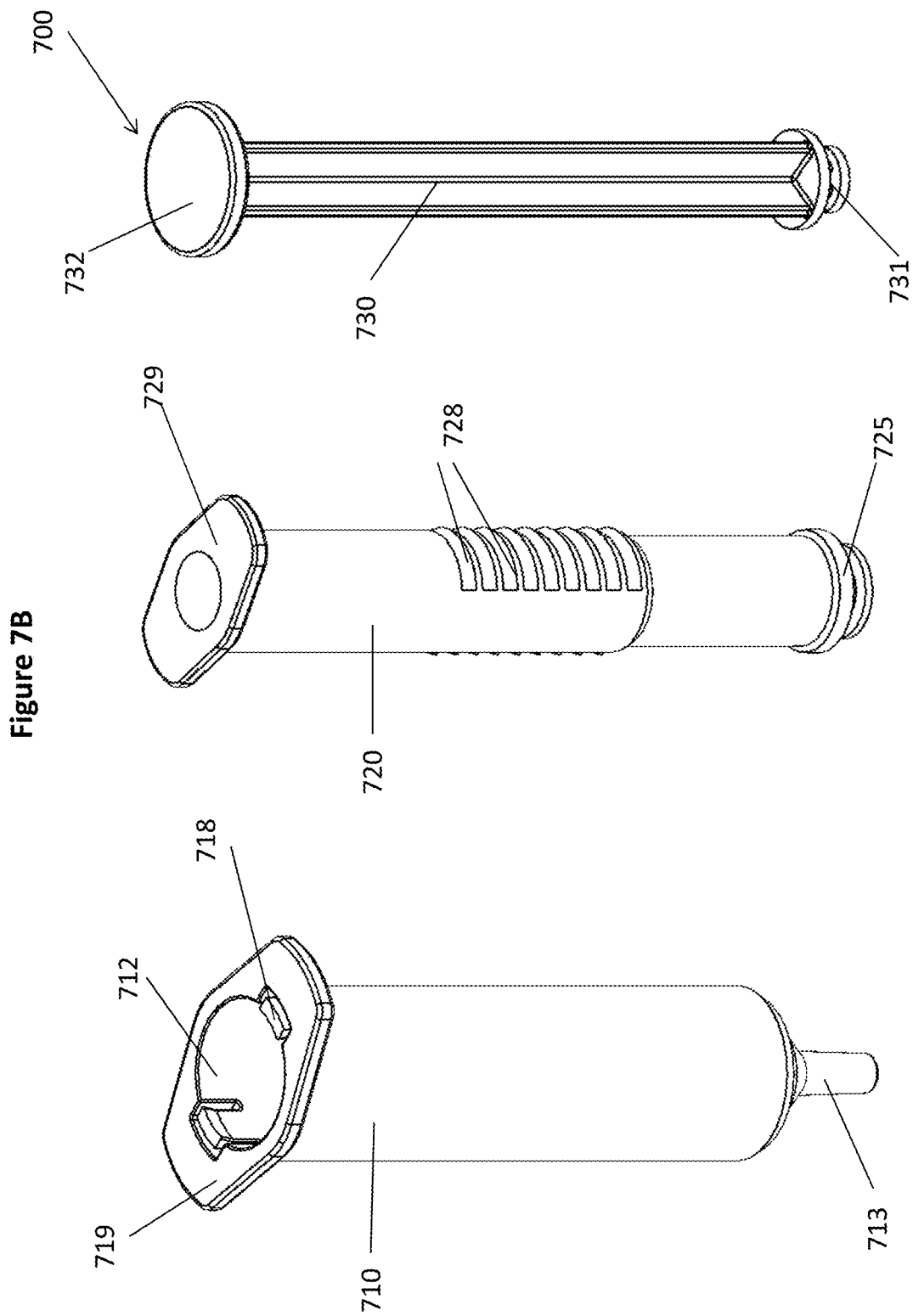

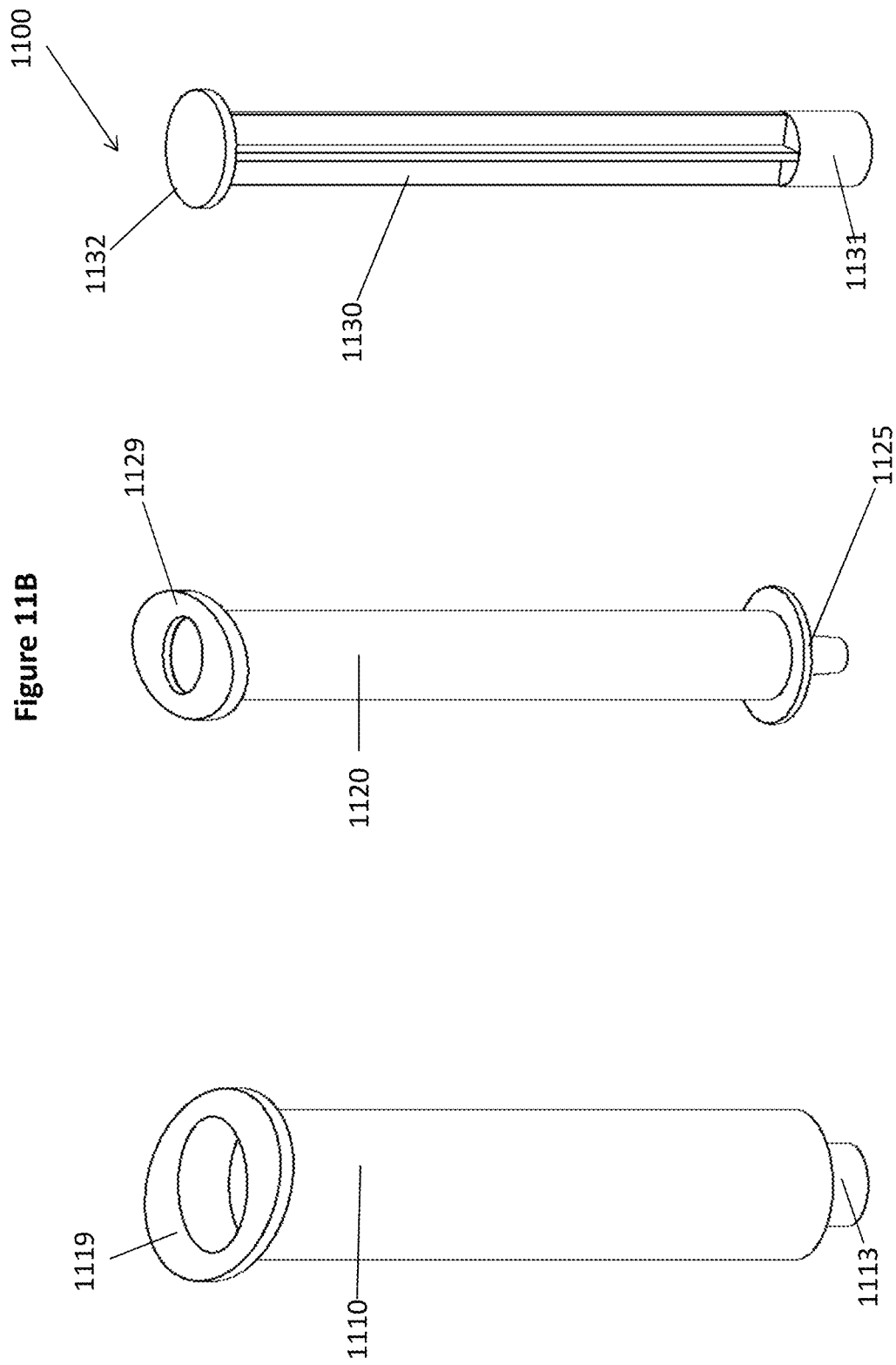

SYRINGE WITH DUAL NESTED CHAMBERS AND METHOD OF USE

FIELD

The present disclosure is of a syringe or more particularly for a syringe with dual nested chambers that are alternately fluidly connected to a single adaptor, and methods of use.

BACKGROUND

When using a hemodialysis machine, it is necessary to perform a variety of pumping and cleaning actions before connecting the patient catheters. This procedure is essential for the maintenance of normal catheter function and flow and for the prevention of blockages. Each time the dialysis machine is connected to a patient, the medical practitioner such as a doctor or nurse must clear the contents of the catheter from the previous treatment. When disconnecting the machine the catheters must be rinsed and then filled/rinsed with an anticoagulant solution.

In typical usage with dual catheters attached to the patient, the following procedure is followed:
  Connection: The hemodialysis locking solution must be withdrawn from each of the arterial and venous lumens prior to initiating dialysis. For each catheter, withdraw (suction) and discard several ml of fluid (blood) using a syringe for each catheter; Then, for each catheter, flush (inject) several ml of physiological solution (usually saline) using a syringe for each catheter; Thus the connection requires the use of four syringes (two injections per catheter arm);
  Disconnection: For each catheter, flush (inject) several ml of physiological solution (usually Saline) using a syringe for each catheter; Then, for each catheter, flush (inject) several ml of anticoagulant solution (depending on accepted protocols for each medical institution) using a syringe for each catheter; Thus the disconnection requires the use of four syringes (two injections per catheter arm);
  Preparation of all four syringes (per catheter) for each of the connection/disconnection processes is time-consuming and exposes medical staff to the risk of being injured by syringe needles (from needle stick due to recapping). In addition, each time a different syringe is connected to the catheters, there is a risk of air embolism, contaminating the sterilization of the catheter, and increased risk of infections to the patient. Finally, although washing the catheter prior to treatment is essential, it is not always performed due to time constraints or the reasons listed above.

In light of the above, there is an urgent need for a solution that will expose staff and the patient to fewer risks, which will require fewer syringes, and that will make it easier for medical staff to complete the connection and disconnection processes without skipping steps.

SUMMARY

The present disclosure overcomes the deficiencies of the background art by providing a dual plunger, nested dual chamber, single adaptor syringe enabling sequential actions of suction and flushing, or flushing and flushing from/into separate chambers within the same device. The dual syringe of the present disclosure significantly eases the process of connecting/disconnecting catheters from a dialysis machine.

As disclosed, only one syringe is required per catheter arm/lumen for connection (as compared to two for the prior art method), and only one syringe is required per catheter arm/lumen for disconnection as compared to two for the prior art method. The use of fewer syringes reduces the dangers to medical staff and to patients and the ease of use ensures correct following of the connection or disconnection procedure/protocols. These in turn provide a positive financial effect due to reduction of the indirect costs of the medical procedure such as reducing catheter related blood stream infections (CRBSI), occlusions, and needle stick injury related costs. Additional benefits are also expected, including workflow efficiencies and improved health care worker safety. Furthermore, the reduction in the disposable medical devices that are required for such procedures have a positive environmental effect (plastic medical waste reduction).

The syringe comprises two nested chambers wherein the second chamber functions as a plunger for insertion into the first chamber. Separate fluid ports connect each chamber to the adaptor tube such that the chambers are not in fluid communication with one another. Thus, in use for connection, one of the chambers can be used for storage of suctioned fluids, while the other chamber can hold physiological fluid for injection. In use for disconnection, one chamber can hold a flushing solution and the other chamber can hold an anticoagulant solution.

As described herein, different embodiments of the syringe are disclosed for connection or disconnection and the methods of use are adapted accordingly. Some embodiments of the syringe comprises a linear ratchet mechanism to prevent insertion or withdrawal of plungers as required by the specific embodiment. These will be further described below. An alternative embodiment provides for rotation of the chambers relative to one another to ensure complete separation during the sequential processes.

The methods of use as described herein primarily relate to use before and after dialysis, however this should not be considered limiting and other uses are contemplated. The syringe is preferably for use in any application requiring subsequent suction/injection or non-simultaneous consecutive injection of more than one fluid. Non-limiting examples of other medical or industrial uses include: medical uses which require flushing with sterile solution after administration to ensure a full dose injection to bloodstream; such as Adenosine Tri phosphate (ATP) for supraventricular arrhythmia, Adrenaline/Atropine for Cardio-Pulmonary Resuscitation (CPR), steroid injection for allergic reaction or COPD exacerbation; sterilizing a cannula after injecting a fluid; or bleeding brake fluid in a vehicle by first sucking out air and fluid and then injecting brake fluid.

According to some embodiments of the present disclosure, a nested syringe comprises: a first chamber comprising: an inner tube extending from a base of the first chamber and defining a base opening in the base; an adapter tube in fluid communication with the inner tube via the base opening; at least one base port in the base for providing fluid communication between the adaptor tube and a first inner volume of the first chamber; a second chamber, adapted for insertion into the first chamber wherein the second chamber comprises a third port adapted to provide fluid communication between the inner tube and a second inner volume of the second chamber and adapted for preventing fluid communication between the first inner volume and the second inner volume when the second chamber is inserted into the first chamber and the inner tube penetrates the third port; and a plunger, wherein the plunger is adapted for insertion into the second chamber.

Preferably the first chamber comprises at least one notch, and the second chamber comprises at least one linear ratchet, and the notch engages the linear ratchet. Preferably the resistance to pulling the plunger out of the second chamber is greater than the resistance to pulling the second chamber out of the first chamber. Preferably the linear ratchet comprises a stop at the bottom of the linear ratchet to prevent removal of the second chamber from the first chamber.

According to some embodiments of the present disclosure a method of preparing a catheter for connection comprises: providing the disclosed nested syringe wherein the second chamber is filled with a physiological solution, the second chamber is fully inserted into the first chamber and the plunger is partially inserted into the second chamber; connecting the syringe to the catheter; pulling the plunger outward from the syringe such that the second chamber is pulled out of the first chamber to thereby draw fluid from the catheter into the first chamber; and pressing the plunger into the syringe such that the plunger moves into the second chamber to thereby force the solution out of the second chamber into the catheter.

Optionally the second chamber comprises at least one notch, and the plunger comprises at least one linear ratchet, and the notch engages the linear ratchet. Optionally the resistance to pulling the plunger out of the second chamber is less than the resistance to pulling the second chamber out of the first chamber. Optionally the linear ratchet comprises a stop at the bottom of the linear ratchet to prevent removal of the plunger from the second chamber.

According to some embodiments of the present disclosure a method of preparing a catheter for connection comprises: providing the disclosed nested syringe wherein the first chamber is filled with a physiological solution, the second chamber is partially inserted into the first chamber and the plunger is fully inserted into the second chamber; connecting the syringe to the catheter; pulling the plunger outward from the syringe such that the plunger is pulled out of the second chamber to thereby draw fluid from the catheter into the second chamber; and pressing the plunger into the syringe such that the second chamber moves into the first chamber to thereby force the solution out of the first chamber into the catheter.

According to some embodiments of the present disclosure a nested syringe comprises: a first chamber comprising: an inner tube extending from a base of the first chamber and defining a base opening in the base; an adapter tube in fluid communication with the inner tube via the base opening; at least one base port in the base for providing fluid communication between the adaptor tube and a first inner volume of the first chamber; a second chamber, adapted for insertion into the first chamber wherein the second chamber comprises: a third port adapted to provide fluid communication between the inner tube and a second inner volume of the second chamber and adapted for preventing fluid communication between the first inner volume and the second inner volume when the second chamber is inserted into the first chamber and the inner tube penetrates the third port; a first stopper, a ridge positioned near the back of the second chamber; and a plunger comprising a second stopper, wherein the plunger is adapted for insertion into the second chamber.

Optionally the resistance to pushing the second chamber into the first chamber is less than the resistance to pushing the plunger into the second chamber. Optionally the difference in resistance is provided by different diameter ratios of a diameter of the first stopper to an inner diameter of the first chamber vs. a diameter of the second stopper to an inner diameter of the second chamber. Optionally the difference in resistance is provided by the plunger having to pass the ridge for further insertion into the second chamber.

According to some embodiments of the present disclosure a method of preparing a catheter for disconnection comprises: providing the disclosed nested syringe wherein the first chamber is filled with a first fluid and the second chamber is filled with a second fluid, the second chamber is partially inserted into the first chamber and the plunger is partially inserted into the second chamber with the second stopper behind the ridge; connecting the syringe to the catheter; pressing the plunger into the syringe such that the second chamber is pushed into the first chamber to thereby force the first fluid out from the first chamber into the adaptor tube and into the catheter; and pressing the plunger into the syringe such that the plunger moves into the second chamber to thereby force the second fluid out of the second chamber into the adaptor tube and into the catheter.

According to some embodiments of the present disclosure, a nested syringe comprises: a first chamber comprising: an adapter tube in fluid communication with a first inner volume of the first chamber via a base opening; a second chamber, adapted for insertion into the first chamber wherein the second chamber comprises: a third port adapted to provide fluid communication between the adaptor tube and a second inner volume of the second chamber; a ridge positioned near the back of the second chamber; a first stopper; and a plunger comprising a second stopper, wherein the plunger is adapted for insertion into the second chamber; wherein the resistance to pushing the second chamber into the first chamber is less than the resistance to pushing the plunger into the second chamber.

Optionally the difference in resistance is provided by different diameter ratios of a diameter of the first stopper to an inner diameter of the first chamber vs. a diameter of the second stopper to an inner diameter of the second chamber. Optionally the difference in resistance is provided by the plunger having to pass the ridge for further insertion into the second chamber.

According to some embodiments of the present disclosure, a method of preparing a catheter for disconnection comprises: providing the disclosed nested syringe wherein the first chamber is filled with a first fluid and the second chamber is filled with a second fluid, the second chamber is partially inserted into the first chamber and the plunger is partially inserted into the second chamber with the second stopper behind the ridge; connecting the syringe to the catheter; pressing the plunger into the syringe such that the second chamber is pushed into the first chamber to thereby force the first fluid out from the first chamber into the adaptor tube and into the catheter; and pressing the plunger into the syringe such that the plunger moves into the second chamber to thereby force the second fluid out of the second chamber into the adaptor tube and into the catheter.

According to some embodiments of the present disclosure, a nested syringe comprises: a first chamber; a second chamber, wherein the second chamber is inserted into the first chamber; and a plunger, wherein the plunger is inserted into the second chamber.

According to further embodiments of the present disclosure, a nested syringe comprises: a first chamber comprising a first port, a second port, and an adaptor tube wherein the first port provides for fluid communication between the inner volume of the first chamber and the inner volume of the adaptor tube; a second chamber, wherein the second chamber comprises a third port, wherein the second chamber is inserted into the first chamber such that the third port provides for fluid communication between the inner volume of the second chamber and the inner volume of the adaptor tube; and a plunger, wherein the plunger is inserted into the second chamber. Preferably the first chamber is a cylindrical hollow chamber sealed on its front end and open at its rear end.

Preferably the first chamber comprise a chamber flange. Preferably the first chamber is tapered on its inner surface near the rear end. Preferably the adaptor tube comprises an adaptor tip adapted for connection to a catheter or medical device. Preferably the first chamber comprises a first notch, and the second chamber comprises a first ratchet, and the first notch engages the first ratchet.

Preferably the second chamber is a cylindrical hollow chamber sealed on its front end and open at a second chamber flange. Preferably the second chamber comprises a plunger stopper comprising a leading ring and a trailing ring wherein the rings are sized so as to firmly engage the inner surface of the first chamber. Preferably the third port is positioned between the rings. Preferably the second chamber is wider at its rear portion. Preferably the first ratchet is one of toothed or smooth. Preferably the second chamber comprises a second notch and wherein the plunger comprises a second ratchet and the second notch engages with the second ratchet. Preferably the circumference of the inner wall of the second chamber is fixed along the majority of its length so as to engage the plunger. Preferably the inner wall of the second chamber is tapered at its rear end. Preferably the plunger comprises up to four parallel blades. Preferably the plunger comprises a plunger stopper affixed to the front of the plunger and wherein the stopper is sized so as to sealably engage the inner wall of the second chamber.

Preferably the plunger comprises a plunger head at its rear end. Preferably the second ratchet is formed on one of the blades of the plunger. Preferably the second ratchet is one of unidirectional or bidirectional. Preferably the first chamber comprises a first notch, and the second chamber comprises a rotation ratchet for engaging with the first notch and wherein the rotation ratchet comprises a third ratchet, rotation guide and fourth ratchet.

Preferably the third and fourth ratchets are one of toothed or smooth. Preferably the first chamber comprises an angled notch, and the second chamber comprises a spiral rotation ratchet for engaging with the angled notch. Preferably each tooth on the first ratchet represents 0.1 cc of volume in the first chamber. Preferably each tooth on the second ratchet represents 0.1 cc of volume in the second chamber.

According to further embodiments of the present disclosure, a method of preparing a catheter for connection comprises: providing the nested syringe of as described hereinabove wherein the first chamber is filled with a physiological solution and the second port is aligned with the third port; connecting the syringe to the catheter; pulling the plunger outward from the syringe such that the plunger is pulled out of the second chamber to draw fluid from the catheter into the second chamber; and depressing the plunger into the syringe to force the solution out of the syringe into the catheter.

Preferably filling the first chamber with the physiological solution comprises: connecting the syringe to a container of physiological solution; pulling the plunger outward from the syringe such that the second chamber is pulled out of the first chamber to draw the solution into the first chamber and to cause the second port to be aligned with the third port; and disconnecting the container of the solution.

According to further embodiments of the present disclosure, a method of preparing a catheter for disconnection comprises: providing the nested syringe of claim 2 wherein the first chamber is filled with a physiological solution and the second chamber is filled with an anticoagulant solution; connecting the syringe to the catheter; depressing the plunger into the syringe to force the second chamber to descend into the first chamber to cause the physiological solution out of the syringe into the catheter and to cause the first port to be aligned with the third port; and depressing the plunger into the second chamber to cause the anticoagulant solution out of the syringe into the catheter.

Preferably filling the first chamber with the physiological solution comprises: connecting the syringe to a container of physiological solution; and pulling the plunger outward from the syringe such that the second chamber is pulled out of the first chamber to draw the solution into the first chamber and to cause the second port to be aligned with the third port. Preferably filling the second chamber with the anticoagulant solution comprises: connecting the syringe to a container of anticoagulant solution; and pulling the plunger outward from the syringe such that the plunger is pulled out of the second chamber to draw the anticoagulant from the catheter into the second chamber.

According to further embodiments of the present disclosure, a method of preparing a catheter for connection comprises: providing the nested syringe wherein the first chamber is filled with a physiological solution and the second port is aligned with the third port; connecting the syringe to the catheter; pulling the plunger outward from the syringe such that the plunger is pulled out of the second chamber to draw fluid from the catheter into the second chamber; and depressing the plunger into the syringe to force the solution out of the syringe into the catheter. Preferably filling the first chamber with the physiological solution comprises: connecting the syringe to a container of physiological solution; pulling the plunger outward from the syringe such that the second chamber is pulled out of the first chamber to draw the solution into the first chamber; and rotating the second chamber within the first chamber to cause the second port to be aligned with the third port.

According to further embodiments of the present disclosure, a method of preparing a catheter for disconnection comprises: providing the nested syringe wherein the first chamber is filled with a physiological solution and the second chamber is filled with an anticoagulant solution; connecting the syringe to the catheter; depressing the plunger into the syringe to force the second chamber to descend into the first chamber to cause the physiological solution out of the syringe into the catheter and to cause the first port to be aligned with the third port; and depressing the plunger into the second chamber to cause the anticoagulant solution out of the syringe into the catheter. Preferably filling the first chamber with the physiological solution comprises: connecting the syringe to a container of physiological solution; and pulling the plunger outward from the syringe such that the second chamber is pulled out of the first chamber to draw the solution into the first chamber; and rotating the second chamber within the first chamber to cause the second port to be aligned with the third port.

Preferably filling the second chamber with the anticoagulant solution comprises: connecting the syringe to a container of anticoagulant solution; and pulling the plunger outward from the syringe such that the plunger is pulled out of the second chamber to draw the anticoagulant from the catheter into the second chamber.

As used herein connection refers to the process of connecting a catheter to a dialysis machine and disconnection refers to the process of disconnecting a catheter from a dialysis machine.

As used herein syringe chamber refers to a syringe barrel or syringe tube.

As used herein syringe adaptor refers to syringe tip or needle hub. The syringe adaptor may comprise a Luer-Lok or adaptor mechanism as known in the art for connecting the adaptor to a catheter, needle, tube or other appliance.

As used herein plunger refers to an injector.

As used herein plunger stopper refers to a plunger piston, plunger tip, plunger rubber, or plunger seal. The stopper comprises a leading ring and a trailing ring wherein the trailing ring is closer to the plunger head.

As used herein plunger head refers to plunger lip, thumb pad, or flat end

As used herein chamber flange refers to a barrel flange, barrel top collar, finger flange, or finger grips.

Physiological solution as used herein refers to one of a group of solutions, including used to maintain tissues in a viable state. These solutions contain specific concentrations of substances that are vital for normal tissue function. The terms saline or physiological saline or saline solution or 0.9% saline may also be used interchangeably herein. As used herein fluid may refer to any fluid typically suctioned into or injected from a syringe.

The term back end as used herein refers to the back end of the plunger and the front end refers to the tip of the adaptor. All components may be referred to with these frames of reference.

Unless otherwise defined, all technical and scientific terms used herein have the same meaning as commonly understood by one of ordinary skill in the art to which this disclosure belongs. The materials, methods, and examples provided herein are illustrative only and not intended to be limiting.

Implementation of the method and system of the present disclosure involves performing or completing certain selected tasks or steps manually, automatically, or a combination thereof.

BRIEF DESCRIPTION OF THE DRAWINGS

The disclosure is herein described, by way of example only, with reference to the accompanying drawings. With specific reference now to the drawings in detail, it is stressed that the particulars shown are by way of example and for purposes of illustrative discussion of the preferred embodiments of the present disclosure only, and are presented in order to provide what is believed to be the most useful and readily understood description of the principles and conceptual aspects of the disclosure. In this regard, no attempt is made to show structural details of the disclosure in more detail than is necessary for a fundamental understanding of the disclosure, the description taken with the drawings making apparent to those skilled in the art how the several forms of the disclosure may be embodied in practice.

In the drawings:

FIGS. 1A-1F are schematic illustrations of a syringe according to at least some embodiments of the present disclosure;

FIGS. 2A-2G are schematic illustrations of a syringe and a flow diagram according to at least some embodiments of the present disclosure;

FIGS. 3A-3H are schematic illustrations of a syringe and a flow diagram according to at least some embodiments of the present disclosure;

FIGS. 4A-4K are schematic illustrations of a syringe and a flow diagram according to at least some embodiments of the present disclosure;

FIGS. 5A-5M are schematic illustrations of a syringe and a flow diagram according to at least some embodiments of the present disclosure;

FIGS. 7A-7H are schematic illustrations of a syringe according to at least some embodiments of the present disclosure;

FIGS. 11A-11D are schematic illustrations of a syringe according to at least some embodiments of the present disclosure;

DETAILED DESCRIPTION

Headings are included herein to aid in locating certain sections of detailed description. These headings should not be considered to limit the scope of the concepts or embodiments described under any specific heading. Furthermore, concepts or embodiments described in any specific heading are generally applicable in other sections or may optionally be combined with other sections throughout the entire specification.

The present disclosure is of a syringe for use in applications requiring sequential or non-simultaneous suction/injection or non-simultaneous injection of more than one fluid. The following dimensions and materials apply to any of the embodiments herein but are exemplary and should not be considered limiting.

Preferably, the syringe is of external diameter of between 0.5 to 3 cm.

Preferably, the internal chamber diameter is between 0.3 to 2 cm.

The material of the syringe is preferably medical grade plastic or any other suitable material. Optionally the syringe is made from a biocompatible material.

The length of the extended syringe is preferably 2-30 cm, more preferably 5-20 cm and most preferably 8-15 cm.

Figure 1A:
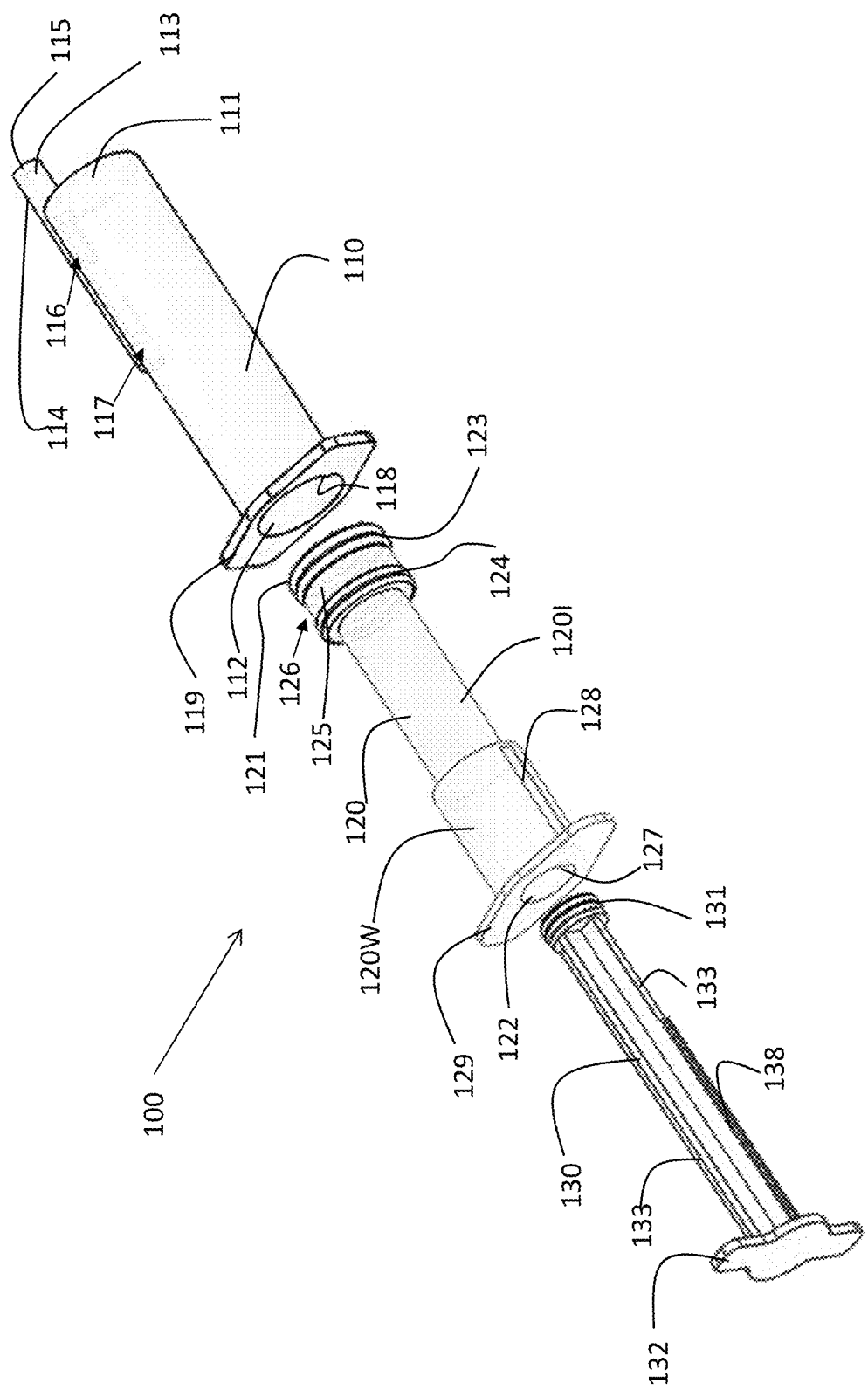

Reference is now made to FIGS. 1A-1F which are schematic illustrations of a syringe according to at least some embodiments of the present disclosure. As shown in FIG. 1A, a syringe 100 comprises a first chamber 110, second chamber 120, and plunger 130. First chamber 110 is a cylindrical hollow chamber sealed on its front end 111 and open at opening 112 at chamber flange 119. First chamber 110 is preferably tapered as known in the art on its inner surface near opening 112 to provide greater resistance and prevent easy removal of inserted second chamber 120. First chamber 110 comprise adaptor 113 for attachment to a catheter (not shown) or other medical device (not shown). Adaptor 113 comprises adaptor tube 114 which is open at adapter tip 115. Adaptor tip 115 has dimensions of syringe adaptors as known in the art including but not limited to Luer Lock tapered termination. First port 116 and second port 117 fluidly connect the volumes within first chamber 110 and adaptor tube 114 depending on the position of second chamber 120 as will be described further below. Optionally First port 116 is longer than second port 117 as will be explained below. Chamber flange 119 comprises first notch 118 for engaging with first ratchet 128 of second chamber 120.

Second chamber 120 is a cylindrical hollow chamber sealed on its front end 121 and open at opening 122 at chamber flange 129. Chamber 122 comprises leading ring 123 and trailing ring 124 of plunger stopper 125. Rings 123 and 124 are sized so as to firmly engage the inner surface of first chamber 110. Rings comprise rubber, silicone or other material known in the art for use in syringe plunger stoppers. Third port 126 is positioned between rings 123 and 124 for lining up with second port 117 as will be described further below.

Second chamber 120 is wider at its rear portion 120W which comprises first linear ratchet 128 for engaging with notch 118 of first chamber 110. First ratchet 128 may be toothed (for connection processes) or may be smooth (for disconnection processes) as further described below. Chamber flange 129 comprises second notch 127 for engaging with second ratchet 138 of plunger 130. The circumference of inner wall 120I of second chamber 120 is fixed along the majority of its length so as to engage plunger 130. Inner wall 120I is tapered at its rear end as is known in the art such that plunger 130 cannot be easily pulled out.

Plunger 130 is formed as a typical plunger as known in the art. The body of plunger 130 comprises up to four parallel blades 133 running the length of plunger 130. Alternatively more blades or no blades are provided. Plunger stopper 131 is affixed to the front of plunger 130. Stopper 131 is sized so as to sealably engage the inner wall 120I of second chamber 120. Plunger 130 comprises a plunger head 132 at its rear end formed for pushing plunger 130 into second chamber 120. Linear second ratchet 138 is formed on one of the blades 133 of plunger 130 so as to engage second notch 127. Second ratchet 138 may be unidirectional (for connection processes) or bidirectional (for disconnection processes) as further described below.

Reference is now made to FIGS. 1B-1D which are schematic illustrations of a syringe according to at least some embodiments of the present disclosure. As shown in FIGS. 1B-1C, second chamber 120 is inserted into first chamber 110 and plunger 130 is inserted into second chamber 120. The components of FIGS. 1B-1D are identical to those of FIG. 1A with the exception of first ratchet 128. As shown, second chamber 120 comprises rotation ratchet 140 which comprises third ratchet 141, rotation guide 142 and fourth ratchet 143. Third and fourth ratchets 141 and 142 may be toothed (for connection processes) or may be smooth (for disconnection processes) as further described below. The operation of rotation ratchet 140 will be further described below. This embodiment of the syringe of the present disclosure comprising rotation ratchet 140 is referred to as syringe 150 herein.

Reference is now made to FIGS. 1E-1F which are schematic illustrations of a syringe according to at least some embodiments of the present disclosure. The components of FIGS. 1E-1F are identical to those of FIG. 1A with the exception of first ratchet 128. Instead of first ratchet 128, second chamber 120 comprises spiral ratchet 162 which spirals around the inside surface of second chamber 120. A further difference is in first chamber 110 which comprises angled notch 164 and not first notch 118. Spiral ratchet 162 may be toothed (for connection processes) or may be smooth (for disconnection processes) as further described below. Angled notch 164 is angled so as to engage spiral ratchet 162. The operation of spiral ratchet 162 will be further described below (with reference to FIG. 6). This embodiment of the syringe of the present disclosure comprising spiral ratchet 162 is referred to as syringe 160 herein.

Figure 2B:
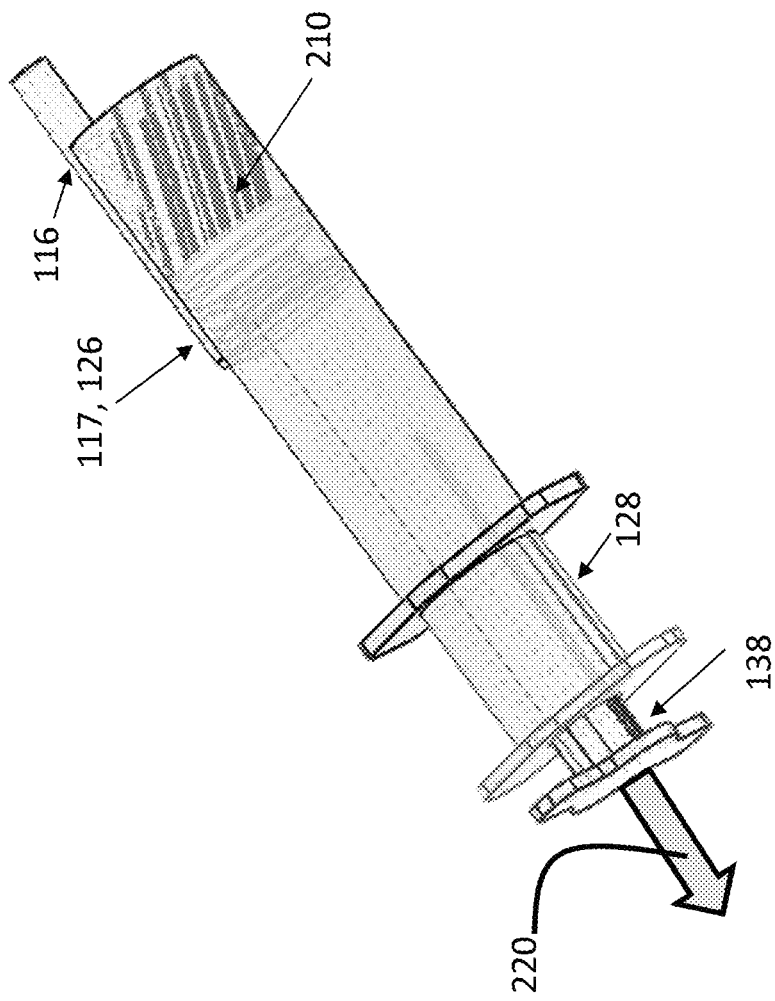

Reference is now made to FIGS. 2A-2G which are schematic illustrations of a syringe and a flow diagram according to at least some embodiments of the present disclosure. The process of FIGS. 2A-2G relates to connection of a CVC (Central Venous Catheter) to a dialysis machine or any process requiring suction followed by injection of different fluids. As shown in FIG. 2A, the syringe 100 of FIG. 1A is provided with second chamber 120 inserted into first chamber 110 and plunger 130 inserted into second chamber 120. Plunger stopper 125 sealably engages the inner walls of first chamber 110 and second chamber 120 thus functions as a syringe plunger for first chamber 110. Plunger head 132 sealably engages the inner walls 120I of second chamber 120 and thus plunger 130 functions as a syringe plunger for second chamber 120. First notch 118 is engaged with first ratchet 128 and second notch 127 is engaged with second ratchet 138.

In stage 1, syringe 100 is connected at adaptor tip 115 to a container of physiological solution (not shown). In stage 2 plunger 130 is pulled outward from syringe 100 in the direction as shown by arrow 220. The resistance of first ratchet 128 is far less than second ratchet 138 and therefore, as shown in FIG. 2B, plunger 130 will pull second chamber 120 outwards from first chamber 110. Since stopper 125 is sealably engaged with the inner wall of chamber 110, negative pressure will be created inside first chamber 110 and since first port 116 is in fluid communication with adaptor tube 114, physiological solution 210 will be drawn through adaptor tip 115 and tube 114 through first port 116 into first chamber 110. It should be appreciated that no fluid is drawn into second chamber 120 as third port 126 is not in fluid communication with adaptor tube 114 and no negative pressure is created in second chamber 120. First notch 118 will move along first ratchet 128 until the front end of first ratchet 128 is reached and second chamber 120 cannot be pulled outwards from first chamber 110 anymore. Alternatively the tapered inner surface of said the first chamber 110 prevent the second chamber 120 from being fully withdrawn from the first chamber 110.

At this point, first chamber 110 has been filled with physiological solution 210 and second port 117 will be aligned with third port 126 and syringe 100 is disconnected from the container of physiological solution. Preferably, syringe 100 may be provided in this state, such as from a manufacturer, i.e., where first chamber 110 is already filled with physiological solution 210 and second port 117 is aligned with third port 126, and stages 1 and 2 may then be skipped, with the process starting at stage 3. This alternative of a prefilled syringe 100 further eases use of the syringe 100 as intended.

Figure 2C:
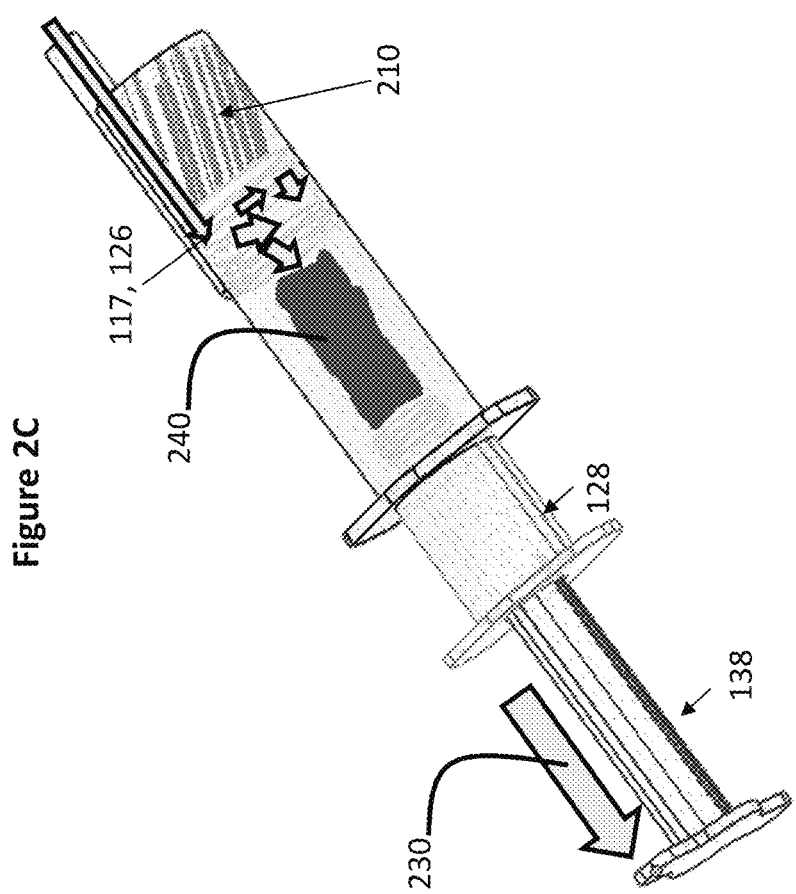

In stage 3, syringe 100 is connected to a catheter (not shown). In stage 4, as shown in FIG. 2C, plunger 130 is pulled outward from syringe 100 in the direction as shown by arrow 230. Since first notch 118 is at the front end of first ratchet 128 and is blocked from moving further, second chamber 120 will no longer be pulled outward from first chamber 110. The pulling force on plunger 130 will thus pull plunger 130 outwards from second chamber 120 and second notch 127 will slide/click along second ratchet 138. Since plunger stopper 131 is sealably engaged with the inner wall 120I of second chamber 120, negative pressure will be created inside second chamber 120 and since third port 126 is in fluid communication with adaptor tube 114 through second port 117, biological fluid 240 such as blood will be drawn through adaptor tube 114 through second port 117 and third port 126 into second chamber 120. It should be appreciated that no fluid is drawn into first chamber 110 as no negative pressure is created inside first chamber 110 since second chamber 120 does not move relative to first chamber 110.

Plunger 130 is preferably withdrawn until a desired volume of fluid has been drawn into second chamber 120. Plunger 130 is pulled out and second notch 127 preferably makes audible sounds as it moves along the notches of second ratchet 138. Optionally each notch of ratchet 138 represents a particular measurement such that the amount of fluid that is drawn into the syringe 100 can be measured. Each notch on ratchet 138 preferably represents 0.1 cc. Optionally first chamber 110 and second chamber 120 each have markings to indicate the volume of fluid therein.

As above, inner wall 120I is tapered such that plunger 130 is prevented from being pulled out of second chamber 120. Alternatively ratchet 138 may comprise a stop notch at its lowest end to prevent plunger 130 from being easily withdrawn. Further, ratchet 138 is unidirectional such that following withdrawal as in stage 4, plunger 130 cannot be pushed into second chamber 120. At the end of stage 4, second chamber 120 has therefore been filled with fluid 240 and first chamber 110 remains filled with physiological solution 210.

Figure 2E:
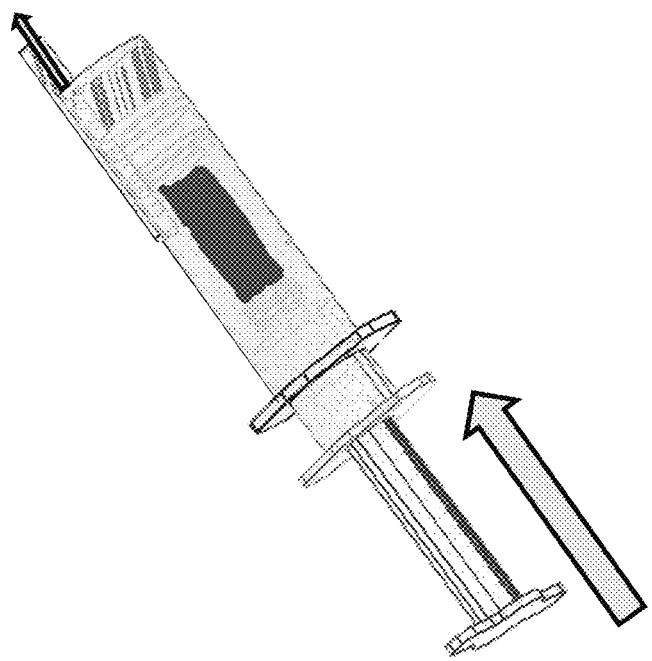
Figure 2D:
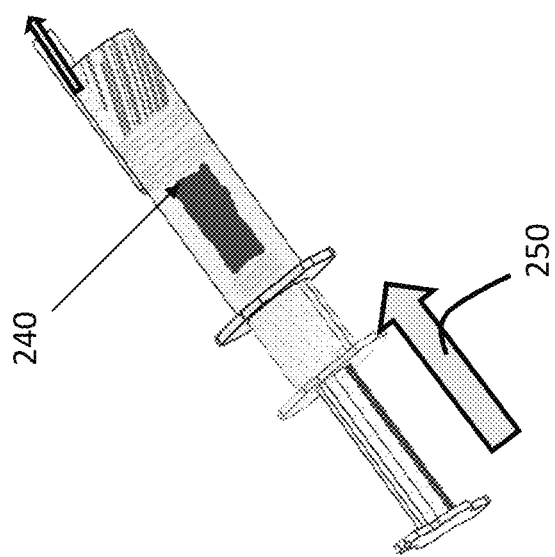
Figure 2F:
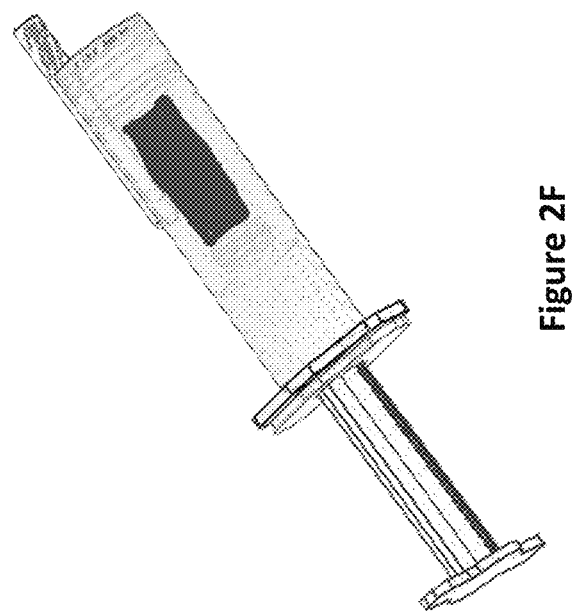
Figure 2G:
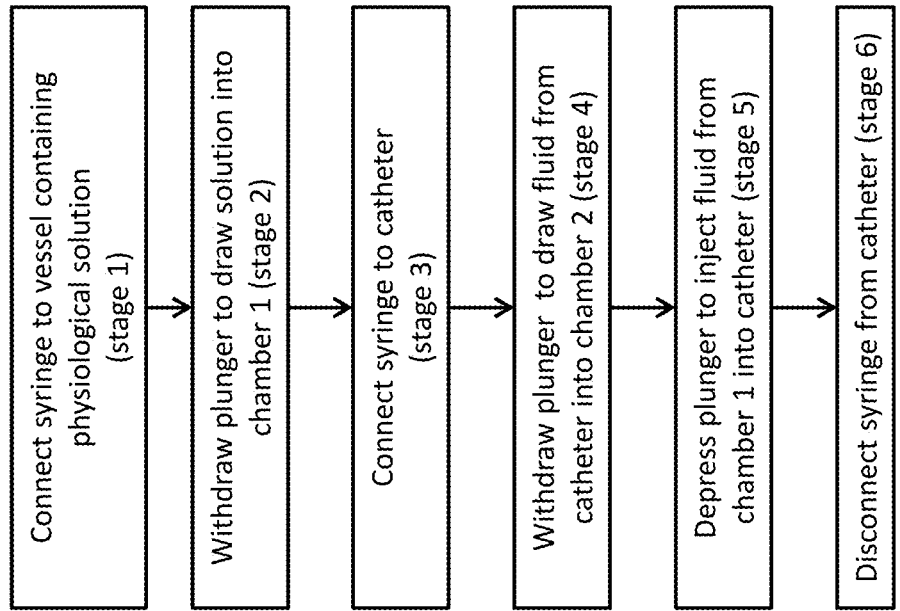

In stage 5, as shown in FIGS. 2D-2F the physiological solution in first chamber 110 is injected into the catheter. Plunger 130 is depressed in the direction as shown by arrow 250. As above, second ratchet 138 prevents plunger 130 from being pushed into second chamber 120 and the pressing force therefore overcomes the resistance of first notch 118 with first ratchet 128 such that second chamber 120 now descends into first chamber 110 and plunger stopper 125 is sealably engaged with the inner walls of first chamber 110 creating positive pressure and pushing the physiological solution 210 out of first chamber 110 through first port 116 into adaptor tube 114 and out of adaptor tip 115 into the attached catheter (not shown). When plunger stopper 125 reaches the bottom of first chamber 110, it can no longer be pushed any further. At the end of stage 5, first chamber 110 is emptied of the physiological solution 210 and second chamber 120 remains filled with fluid 240.

In stage 6 the syringe is disconnected from the catheter and is preferably discarded.

Figure 3A:
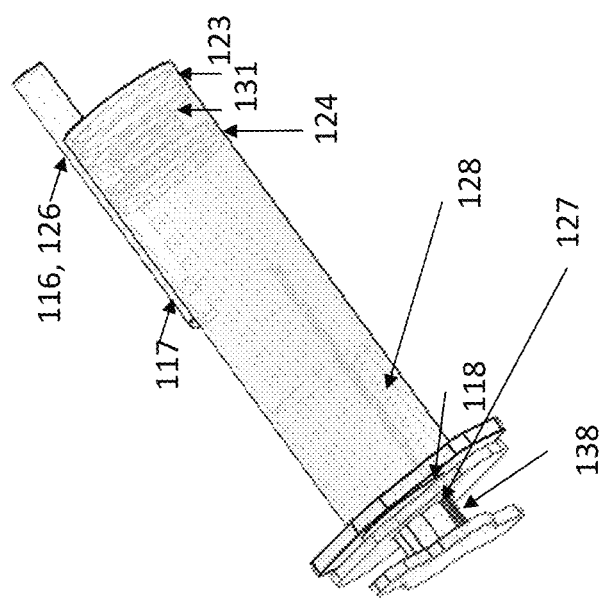

Reference is now made to FIGS. 3A-3H which are schematic illustrations of a syringe and a flow diagram according to at least some embodiments of the present disclosure. The process of FIGS. 3A-3H relates to disconnection of a CVC (Central Venous Catheter) from a dialysis machine or any process requiring sequential injection of different fluids. As shown in FIG. 3A, the syringe 100 of FIG. 1A is provided with second chamber 120 inserted into first chamber 110 and plunger 130 inserted into second chamber 120. Plunger stopper 125 sealably engages the inner walls of first chamber 110 and second chamber 120 thus functions as a syringe plunger for first chamber 110. Plunger head 132 sealably engages the inner walls 120I of second chamber 120 and thus plunger 130 functions as a syringe plunger for second chamber 120. First notch 118 is engaged with first ratchet 128 and second notch 127 is engaged with second ratchet 138.

Figure 3B:
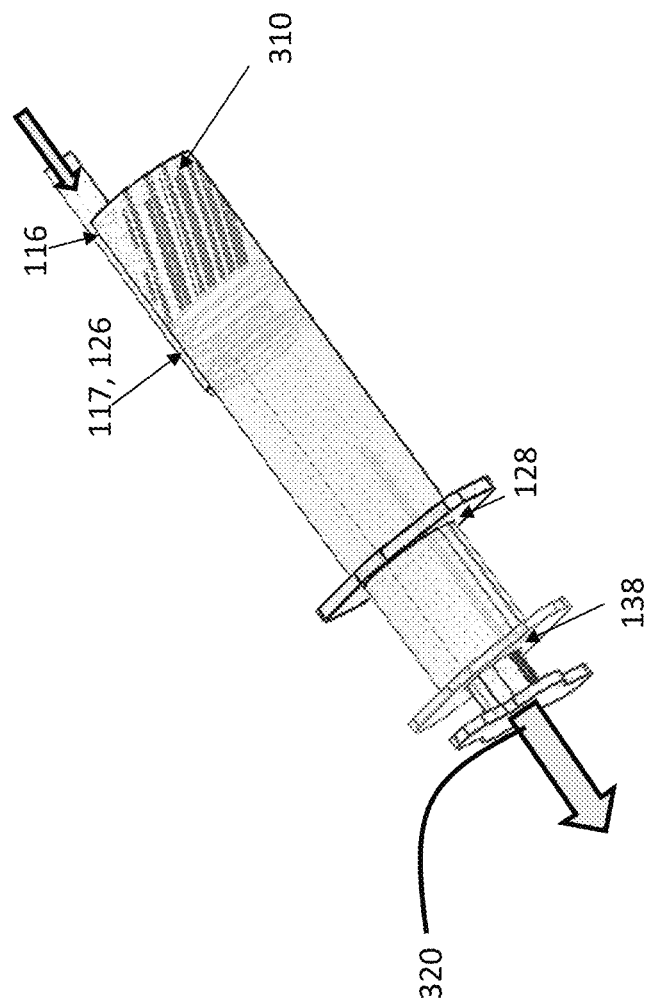

In stage 1, syringe 100 is connected at adaptor tip 115 to a container of physiological solution (not shown). In stage 2, as shown in FIG. 3B, plunger 130 is pulled outward from syringe 100 in the direction as shown by arrow 320. For this process, first ratchet 128 is flat along its length and thus provides no resistance while second ratchet 138 does provide resistance and therefore, as shown in FIG. 2B, plunger 130 will pull second chamber 120 outwards from first chamber 110. Since stopper 125 is sealably engaged with the inner wall of chamber 110, negative pressure will be created inside first chamber 110 and since first port 116 is in fluid communication with adaptor tube 114, physiological solution 210 will be drawn through adaptor tip 115 and tube 114 through first port 116 into first chamber 110. It should be appreciated that no fluid is drawn into second chamber 120 as third port 126 is not in fluid communication with adaptor tube 114 and no negative pressure is created in second chamber 120.

Second chamber 120 is preferably withdrawn until a desired volume of fluid has been drawn into first chamber 110. Preferably first chamber 110 and second chamber 120 each have markings to indicate the volume of fluid therein. Optionally notches of ratchet 128 make audible sounds as first notch 118 engages them where each notch represents a particular measurement such that the amount of fluid that is drawn into the first chamber 110 can be measured. Each notch on ratchet 128 preferably represents 1 cc.

As above, inner wall of first chamber 110 is tapered such that second chamber 120 is prevented from being easily pulled out of first chamber 110. Alternatively ratchet 128 may comprise a stop notch at its lowest end to prevent second chamber 120 from being withdrawn. In this case, first notch 118 will move along first ratchet 128 until the raised front end of first ratchet 128 is reached and second chamber 120 cannot be pulled outwards from first chamber 110 anymore.

At this point, first chamber 110 has been filled with physiological solution 210 and second port 117 will be aligned with third port 126 and syringe 100 is disconnected from the container of physiological solution.

In stage 3, syringe 100 is connected to a container containing an anticoagulant. In stage 4, as shown in FIG. 3C, plunger 130 is pulled outward from syringe 100 in the direction as shown by arrow 330. Since first notch 118 is at the front end of first ratchet 128 and is blocked from moving further, second chamber 120 will no longer be pulled outward from first chamber 110. The pulling force on plunger 130 will thus pull plunger 130 outwards from second chamber 120 and second notch 127 will slide/click along second ratchet 138. Since plunger stopper 131 is sealably engaged with the inner wall 120I of second chamber 120, negative pressure will be created inside second chamber 120 and since third port 126 is in fluid communication with adaptor tube 114 through second port 117, anticoagulant 340 will be drawn through adaptor tube 114 through second port 117 and third port 126 into second chamber 120. It should be appreciated that no fluid is drawn into first chamber 110 as no negative pressure is created inside first chamber 110 since second chamber 120 does not move relative to first chamber 110.

Plunger 130 is preferably withdrawn until a desired volume of fluid has been drawn into second chamber 120. Plunger 130 is pulled out and second notch 127 preferably makes audible sounds as it moves along the notches of second ratchet 138. Optionally each notch of ratchet 138 represents a particular measurement such that the amount of fluid that is drawn into the syringe 100 can be measured. Each notch on ratchet 138 preferably represents 0.1 cc. Optionally first chamber 110 and second chamber 120 each have markings to indicate the volume of fluid therein.

As above, inner wall 120I is tapered such that plunger 130 is prevented from being easily pulled out of second chamber 120. Alternatively ratchet 138 may comprise a stop notch at its lowest end to prevent plunger 130 from being easily withdrawn. At the end of stage 4, second chamber 120 has therefore been filled with anticoagulant 340 and first chamber 110 remains filled with physiological solution 310.

Preferably, syringe 100 may be provided in this state, such as from a manufacturer, i.e., where first chamber 110 is already filled with physiological solution 310 and second chamber 120 is already filled with anticoagulant 340, and stages 1-4 may then be skipped, with the process starting at stage 5. This alternative of a prefilled syringe 100 further eases use of the syringe 100 as intended.

Figure 3E:
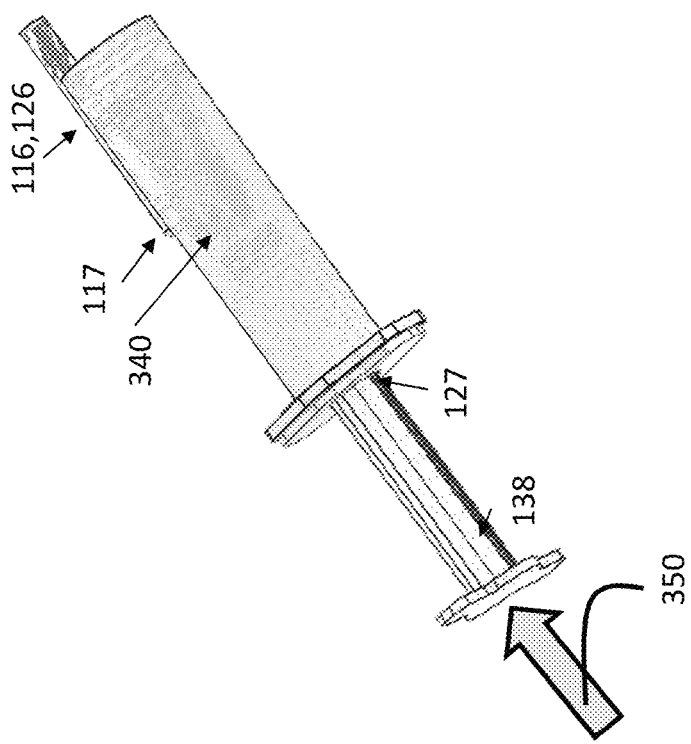
Figure 3D:
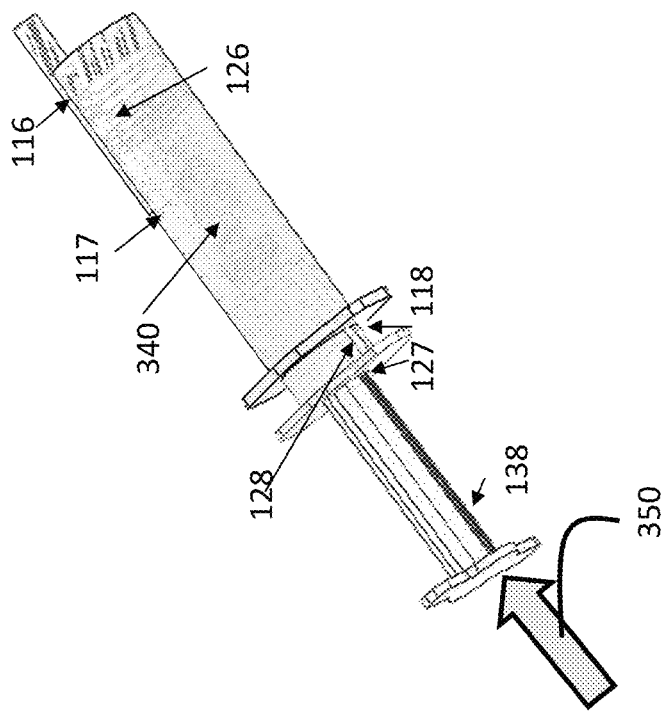
Figure 3H:
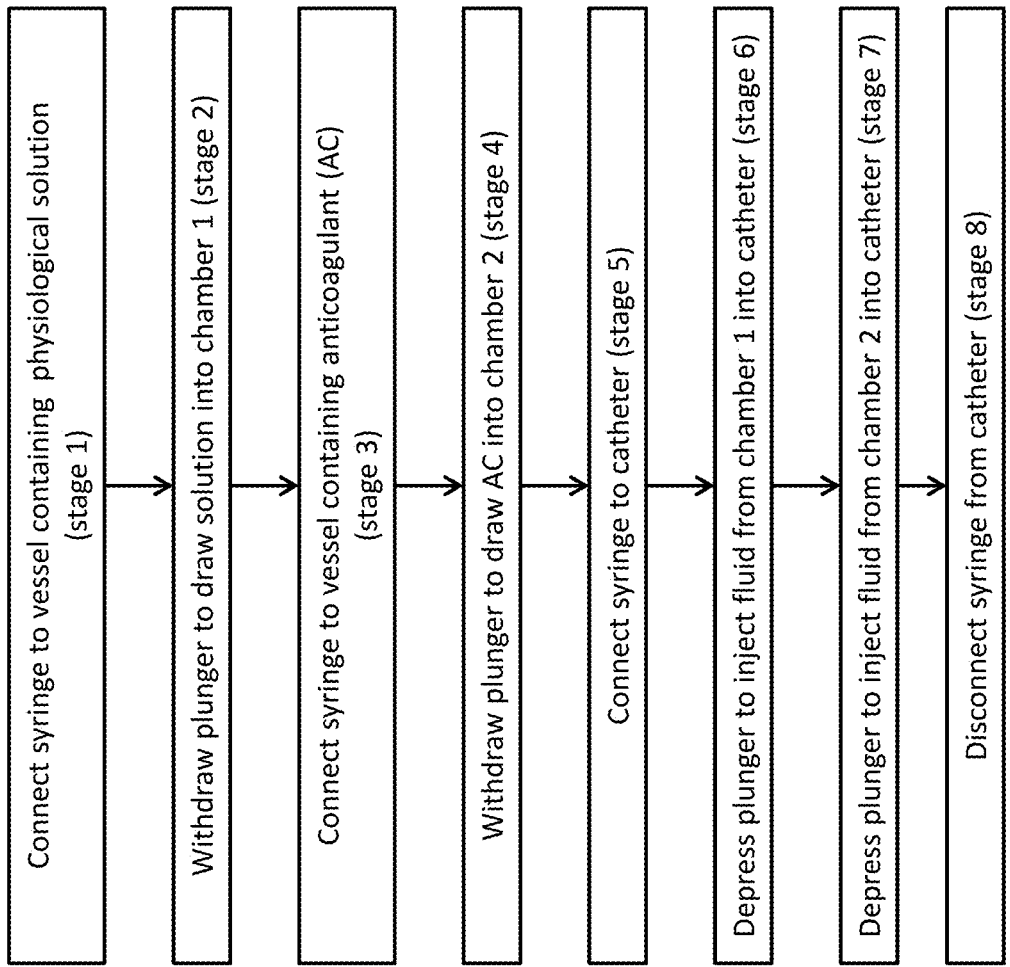

In stage 5, syringe 100 is connected to a catheter (not shown). In stage 6, as shown in FIGS. 3D-3E the physiological solution in first chamber 110 is injected into the catheter. Plunger 130 is depressed in the direction as shown by arrow 350. As above, first ratchet 128 is smooth and therefore provides no resistance compared to second ratchet 138 and second chamber 120 now descends into first chamber 110 and plunger stopper 125 is sealably engaged with the inner walls of first chamber 110 creating positive pressure and pushing the physiological solution 210 out of first chamber 110 through first port 116 into adaptor tube 114 and out of adaptor tip 115 into the attached catheter (not shown). When plunger stopper 125 reaches the bottom of first chamber 110, it can no longer be pushed any further. At the end of stage 5, first chamber 110 is emptied of the physiological solution 210, second chamber remains filled with anticoagulant 340, and first port 116 is aligned with third port 126.

In stage 7, as shown in FIGS. 3F-3G the anticoagulant 340 in second chamber 120 is injected into the catheter. Plunger 130 is depressed in the direction as shown by arrow 350. Since second chamber 120 cannot descend further into first chamber 110, the pressing force on plunger 130 overcomes the resistance of second ratchet 138 and plunger 130 now descends into second chamber 120 and plunger stopper 131 is sealably engaged with the inner walls 120I of second chamber 120 creating positive pressure and pushing the anticoagulant 340 out of second chamber 120 through third port 126 and first port 116 into adaptor tube 114 and out of adaptor tip 115 into the attached catheter (not shown). When plunger stopper 131 reaches the bottom of second chamber 120, it can no longer be pushed any further.

In stage 8 the syringe is disconnected from the catheter and is preferably discarded.

Figure 4D:
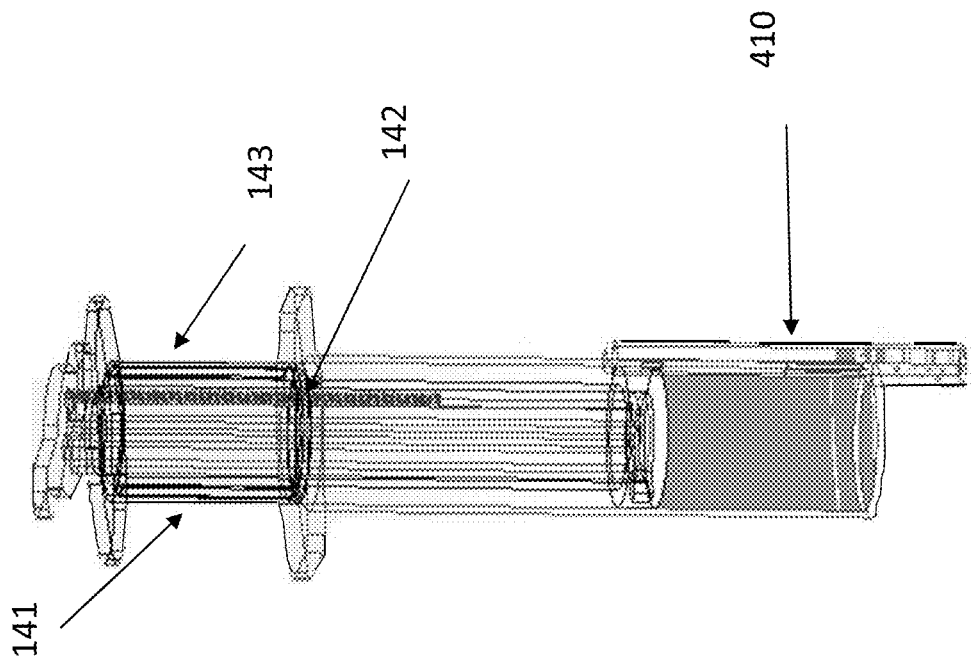

Reference is now made to FIGS. 4A-4K which are schematic illustrations of a syringe and a flow diagram according to at least some embodiments of the present disclosure. The process of FIGS. 4A-4K relates to connection of a dialysis machine or any process requiring suction followed by injection of different fluids. As shown in FIG. 4A, the syringe 150 of FIGS. 1B-1D is provided with second chamber 120 inserted into first chamber 110 and plunger 130 inserted into second chamber 120. Plunger stopper 125 sealably engages the inner walls of first chamber 110 and second chamber 120 thus functions as a syringe plunger for first chamber 110. Plunger head 132 sealably engages the inner walls 120I of second chamber 120 and thus plunger 130 functions as a syringe plunger for second chamber 120. First notch 118 is engaged with third ratchet 141 and second notch 127 is engaged with second ratchet 138.

Figure 4C:
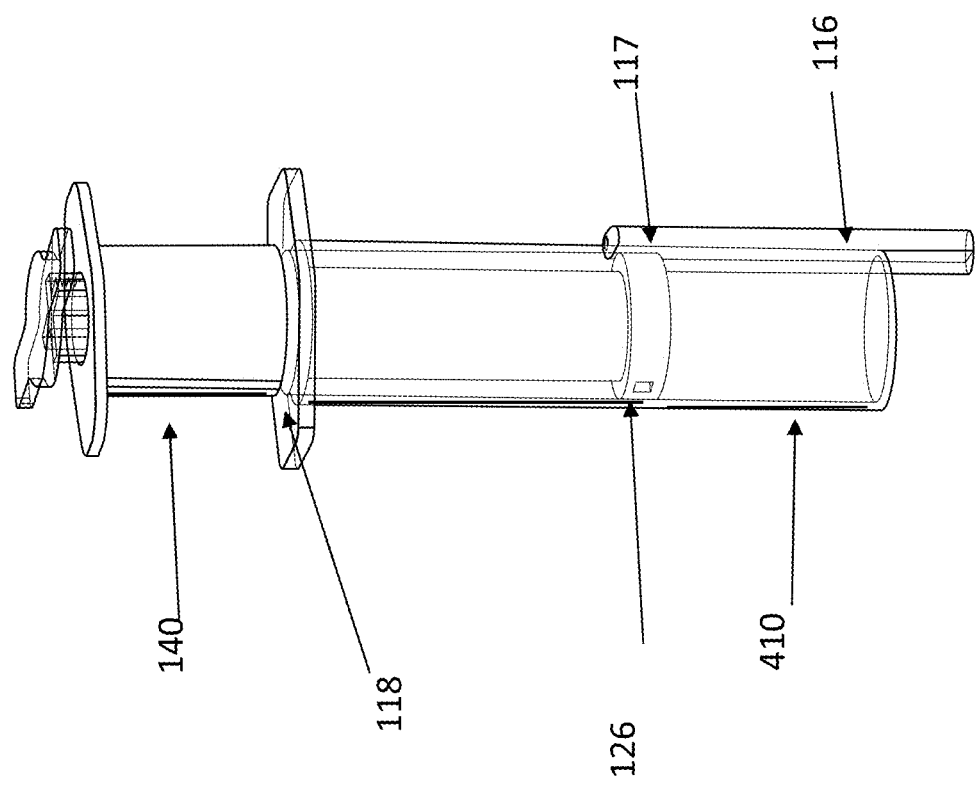

In stage 1, syringe 100 is connected at adaptor tip 115 to a container of physiological solution (not shown). In stage 2, as shown in FIGS. 4C and 4D, plunger 130 is pulled outward from syringe 100 in the direction as shown by arrow 420. The resistance of third ratchet 141 is far less than second ratchet 138 and therefore, as shown in FIGS. 4C-4D, plunger 130 will pull second chamber 120 outwards from first chamber 110. Since stopper 125 is sealably engaged with the inner wall of chamber 110, negative pressure will be created inside first chamber 110 and since first port 116 is in fluid communication with adaptor tube 114, physiological solution 210 will be drawn through adaptor tip 115 and tube 114 through first port 116 into first chamber 110. It should be appreciated that no fluid is drawn into second chamber 120 as third port 126 is rotated 180 degrees away from adaptor 113 and is not in fluid communication with adaptor tube 114 and no negative pressure is created in second chamber 120. First notch 118 will move along third ratchet 128 until the front end of first ratchet 128 is reached and second chamber 120 cannot be pulled outwards from first chamber 110 anymore. Syringe 150 is then disconnected from the container of physiological solution.

Figure 4F:
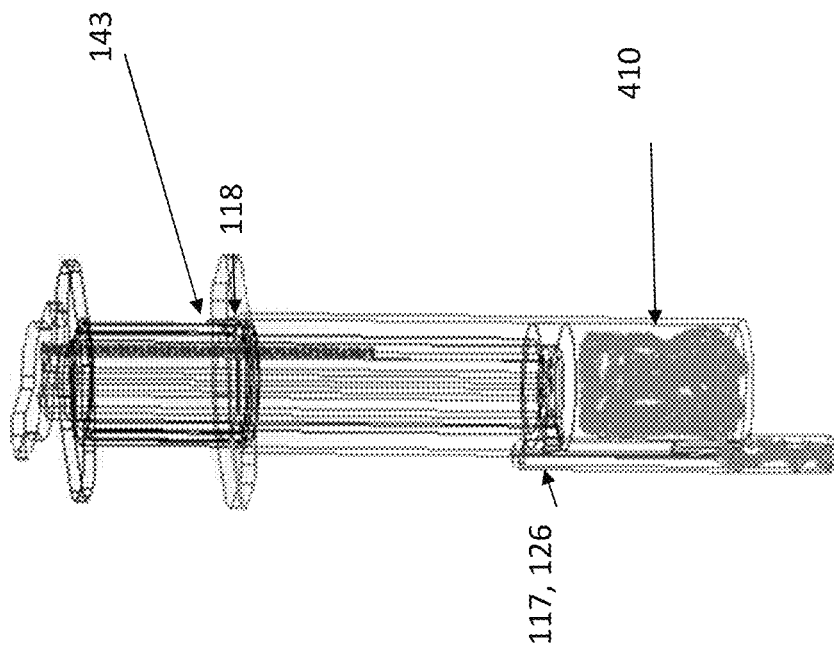
Figure 4E:
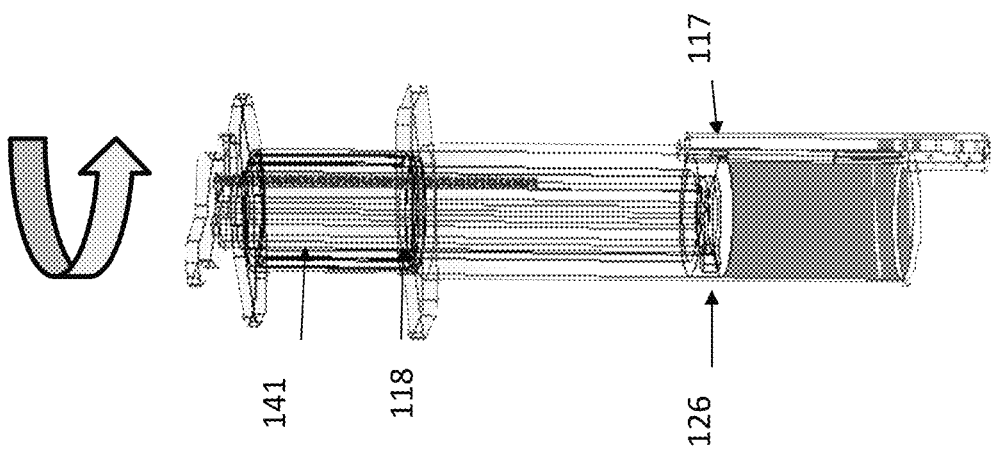
Figure 4K:
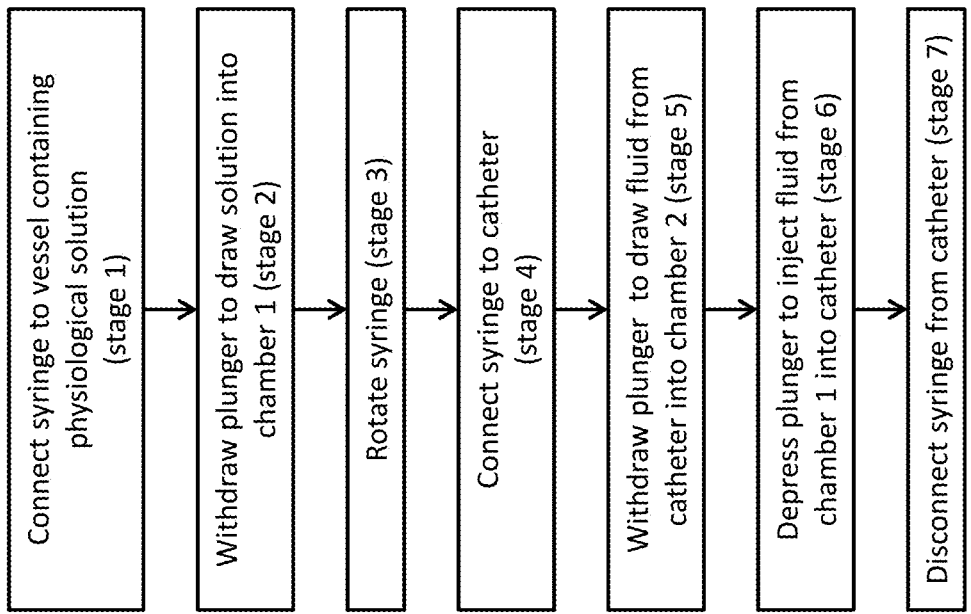

At this point, first chamber 110 has been filled with physiological solution 410. In stage 3, as shown in FIGS. 4E and 4F, in order to align second port 117 with third port 126, first chamber 110 is held while plunger 130 is rotated. First notch 118 now engages rotation guide 142 and moves within guide 142 until notch 118 is aligned with fourth ratchet 143. At this point second port 117 will be aligned with third port 126.

In stage 4, syringe 150 is connected to a catheter (not shown). In stage 5, as shown in FIG. 4G, plunger 130 is pulled outward from syringe 100 in the direction as shown by arrow 430. Since first notch 118 is at the front end of fourth ratchet 128 and is blocked from moving further, second chamber 120 will not be pulled outward from first chamber 110. The pulling force on plunger 130 will thus pull plunger 130 outwards from second chamber 120 and second notch 127 will slide/click along second ratchet 138. Since plunger stopper 131 is sealably engaged with the inner wall 120I of second chamber 120, negative pressure will be created inside second chamber 120 and since third port 126 is in fluid communication with adaptor tube 114 through second port 117 (following the rotation of stage 3), biological fluid 440 such as blood will be drawn through adaptor tube 114 through second port 117 and third port 126 into second chamber 120. It should be appreciated that no fluid is drawn into first chamber 110 as no negative pressure is created inside first chamber 110 since second chamber 120 does not move relative to first chamber 110.

Plunger 130 is preferably withdrawn until a desired volume of fluid has been drawn into second chamber 120. Plunger 130 is pulled out and second notch 127 preferably makes audible sounds as it moves along the notches of second ratchet 138. Optionally each notch of ratchet 138 represents a particular measurement such that the amount of fluid that is drawn into the syringe 100 can be measured. Each notch on ratchet 138 preferably represents 0.1 cc. Optionally first chamber 110 and second chamber 120 each have markings to indicate the volume of fluid therein.

As above, inner wall 120I is tapered such that plunger 130 is prevented from being pulled out of second chamber 120. Alternatively ratchet 138 may comprise a stop notch at its lowest end to prevent plunger 130 from being easily withdrawn. Further, for connection applications, ratchet 138 is unidirectional such that following withdrawal as in stage 5, plunger 130 cannot be pushed into second chamber 120. At the end of stage 5, second chamber 120 has therefore been filled with fluid 440 and first chamber 110 remains filled with physiological solution 410.

In stage 6, as shown in FIGS. 4H-4J the physiological solution 410 in first chamber 110 is injected into the catheter. Plunger 130 is depressed in the direction as shown by arrow 450. As above, second ratchet 138 prevents plunger 130 from being pushed into second chamber 120 and the pressing force therefore overcomes the resistance of first notch 118 with fourth ratchet 143 such that second chamber 120 now descends into first chamber 110 and plunger stopper 125 is sealably engaged with the inner walls of first chamber 110 creating positive pressure and pushing the physiological solution 210 out of first chamber 110 through first port 116 into adaptor tube 114 and out of adaptor tip 115 into the attached catheter (not shown). When plunger stopper 125 reaches the bottom of first chamber 110, it can no longer be pushed any further. At the end of stage 6, first chamber 110 is emptied of the physiological solution 410 and second chamber 120 remains filled with fluid 440.

In stage 7 the syringe is disconnected from the catheter and is preferably discarded.

Figure 5B:
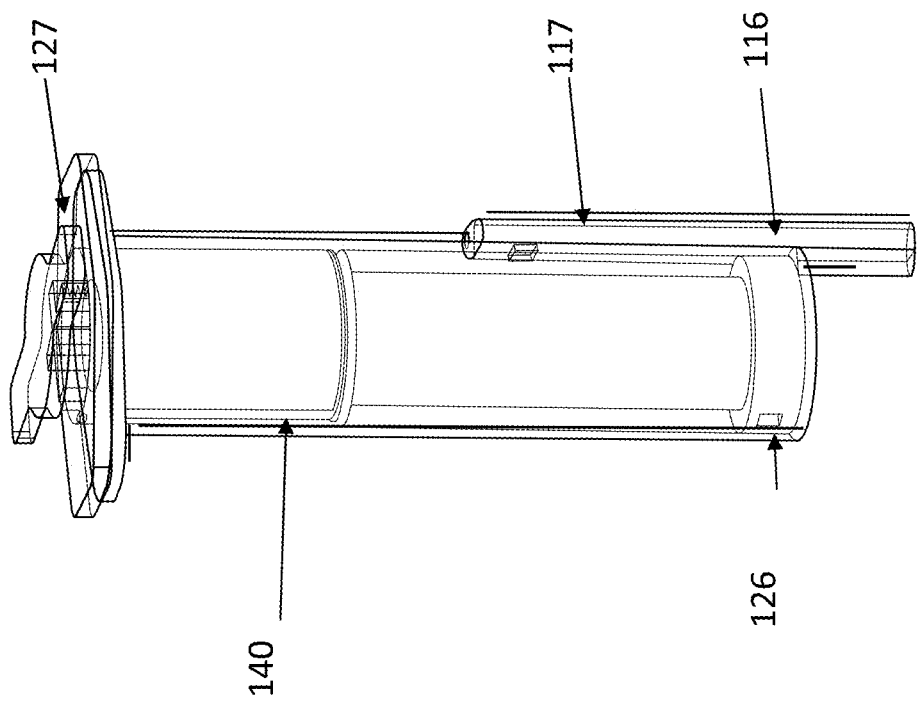
Figure 5A:
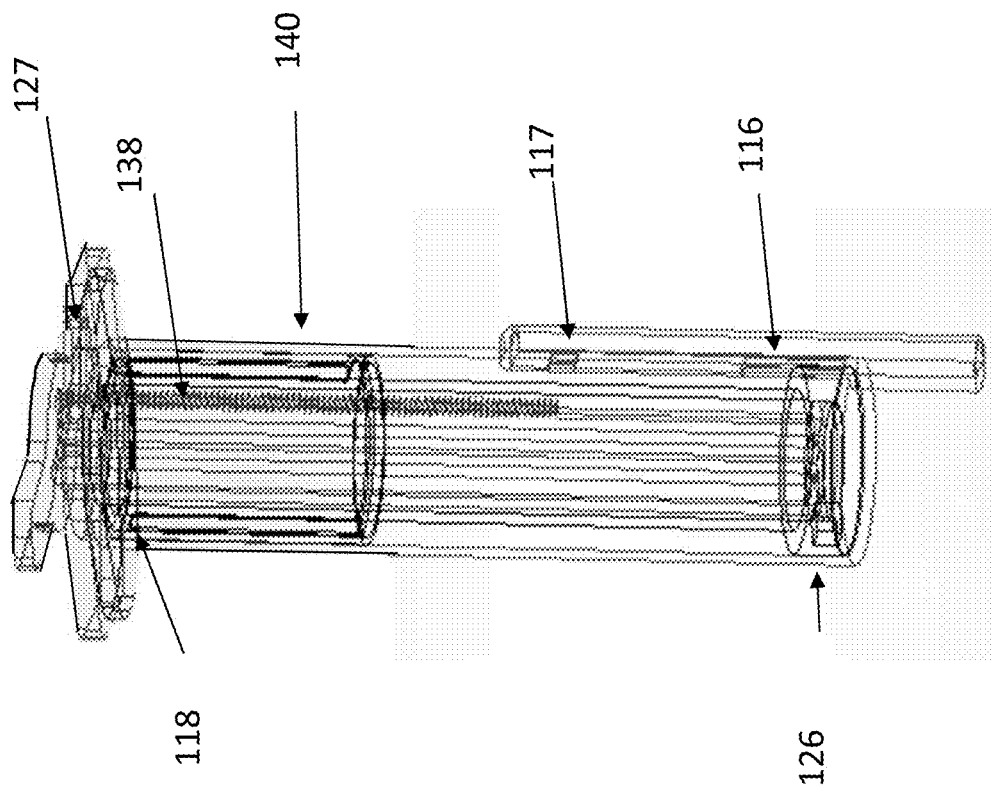

Reference is now made to FIGS. 5A-5M which are schematic illustrations of a syringe and a flow diagram according to at least some embodiments of the present disclosure. The process of FIGS. 5A-5M relates to disconnection of a dialysis machine or any process requiring sequential injection of different fluids. As shown in FIGS. 5A-5B, the syringe 150 of FIGS. 1B-1D is provided with second chamber 120 inserted into first chamber 110 and plunger 130 inserted into second chamber 120. Plunger stopper 125 sealably engages the inner walls of first chamber 110 and second chamber 120 thus functions as a syringe plunger for first chamber 110. Plunger head 132 sealably engages the inner walls 120I of second chamber 120 and thus plunger 130 functions as a syringe plunger for second chamber 120. First notch 118 is engaged with third ratchet 141 and second notch 127 is engaged with second ratchet 138.

Figure 5D:
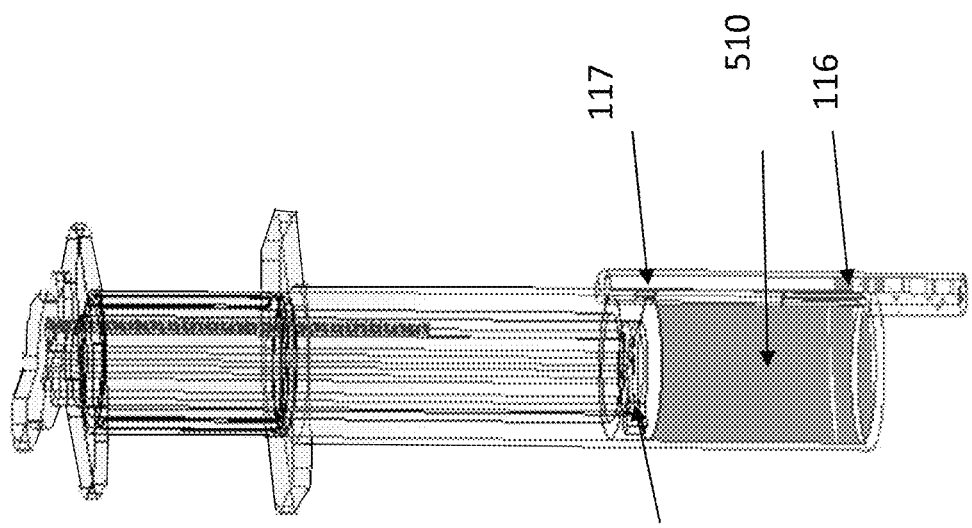
Figure 5C:
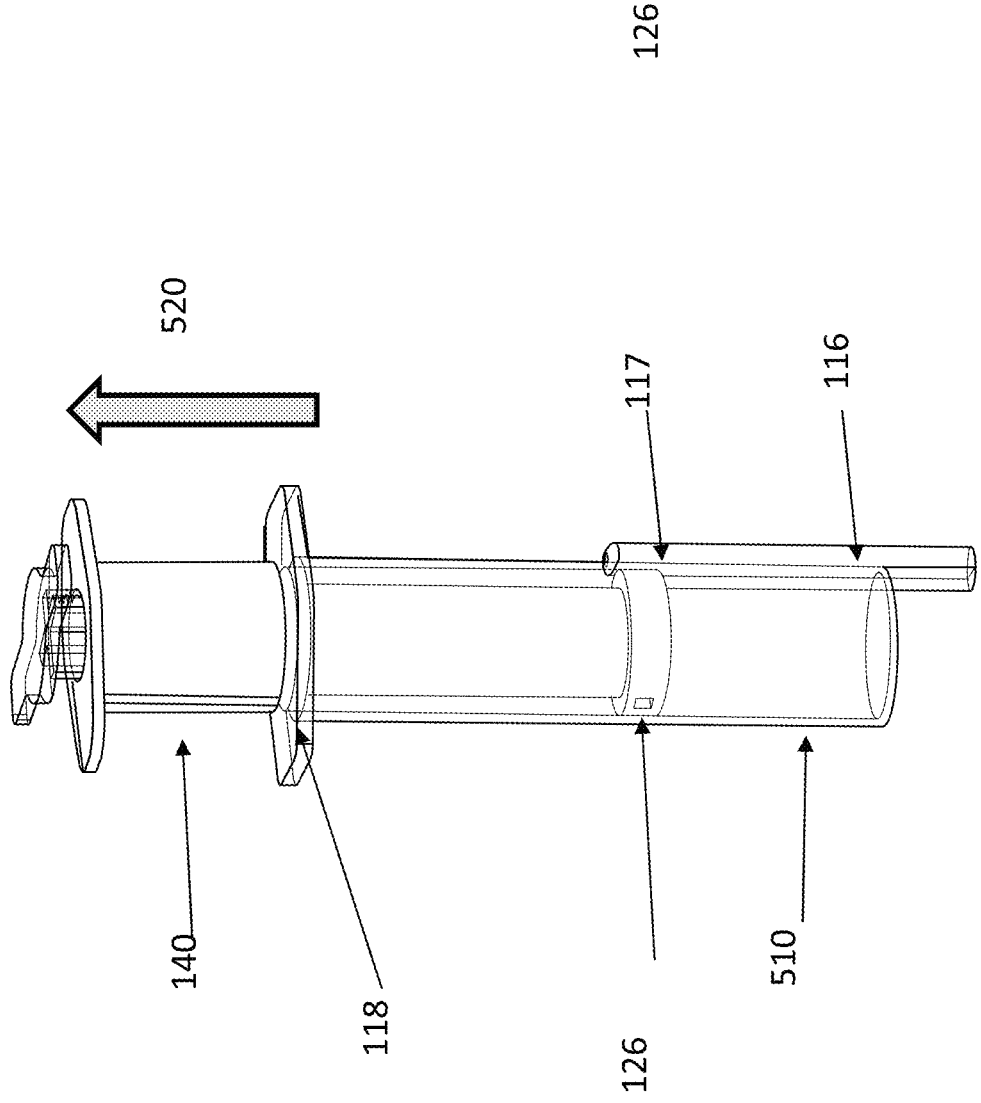

In stage 1, syringe 150 is connected at adaptor tip 115 to a container of physiological solution (not shown). In stage 2, as shown in FIGS. 5C and 5D, plunger 130 is pulled outward from syringe 100 in the direction as shown by arrow 520. For this process, third ratchet 128 is flat along its length and thus provides no resistance while second ratchet 138 does provide resistance and therefore, as shown in FIG. 2B, plunger 130 will pull second chamber 120 outwards from first chamber 110. Since stopper 125 is sealably engaged with the inner wall of chamber 110, negative pressure will be created inside first chamber 110 and since first port 116 is in fluid communication with adaptor tube 114, physiological solution 510 will be drawn through adaptor tip 115 and tube 114 through first port 116 into first chamber 110. It should be appreciated that no fluid is drawn into second chamber 120 as third port 126 is rotated 180 degrees away from adaptor 113 and is not in fluid communication with adaptor tube 114 and no negative pressure is created in second chamber 120. First notch 118 will move along third ratchet 141 until the raised front end of third ratchet 141 is reached and second chamber 120 cannot be pulled outwards from first chamber 110 anymore. Syringe 150 is now disconnected from the container of physiological solution.

Figure 5F:
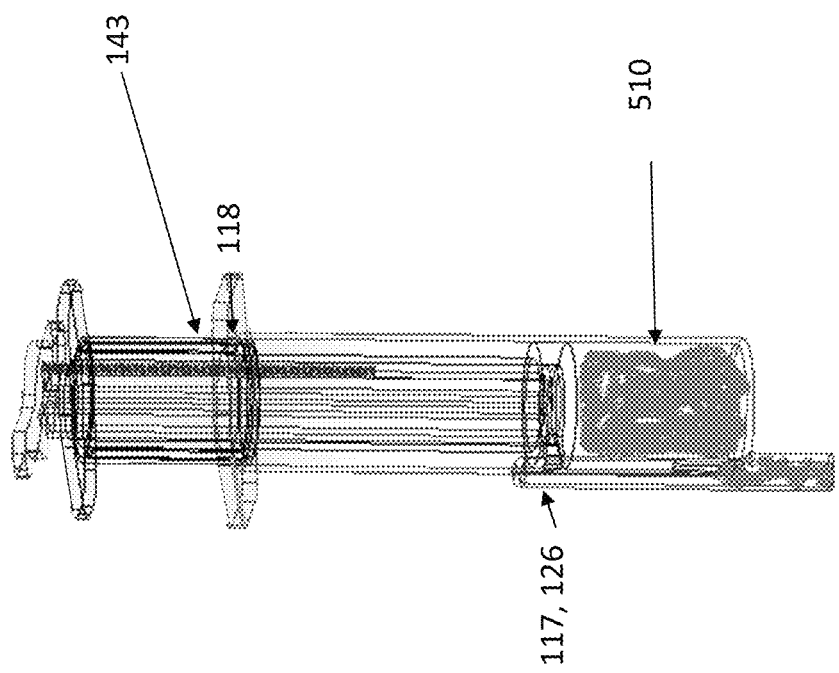
Figure 5E:
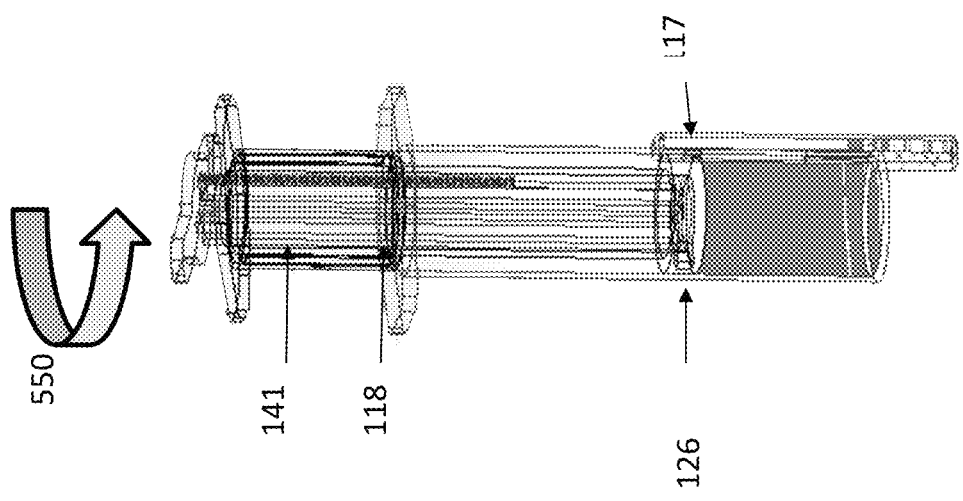

At this point, first chamber 110 has been filled with physiological solution 510. In stage 3, as shown in FIGS. 5E and 5F, in order to align second port 117 with third port 126, first chamber 110 is held while plunger 130 is rotated in the direction shown by arrow 550. First notch 118 now engages rotation guide 142 and moves within guide 142 until notch 118 is aligned with fourth ratchet 143. At this point second port 117 will be aligned with third port 126.

In stage 4, syringe 150 is connected to a container containing an anticoagulant. In stage 5, as shown in FIG. 5G, plunger 130 is pulled outward from syringe 100 in the direction as shown by arrow 530. Since first notch 118 is at the front end of fourth ratchet 143 and is blocked from moving further, second chamber 120 will no longer be pulled outward from first chamber 110. The pulling force on plunger 130 will thus pull plunger 130 outwards from second chamber 120 and second notch 127 will slide/click along second ratchet 138. Since plunger stopper 131 is sealably engaged with the inner wall 120I of second chamber 120, negative pressure will be created inside second chamber 120 and since third port 126 is in fluid communication with adaptor tube 114 (following the rotation of stage 3) through second port 117, anticoagulant 540 will be drawn through adaptor tube 114 through second port 117 and third port 126 into second chamber 120. It should be appreciated that no fluid is drawn into first chamber 110 as no negative pressure is created inside first chamber 110 since second chamber 120 does not move relative to first chamber 110.

Plunger 130 is preferably withdrawn until a desired volume of fluid has been drawn into second chamber 120. Plunger 130 is pulled out and second notch 127 preferably makes audible sounds as it moves along the notches of second ratchet 138. Optionally each notch of ratchet 138 represents a particular measurement such that the amount of fluid that is drawn into the syringe 100 can be measured. Each notch on ratchet 138 preferably represents 0.1 cc. Optionally first chamber 110 and second chamber 120 each have markings to indicate the volume of fluid therein.

As above, inner wall 120I is tapered such that plunger 130 is prevented from being easily pulled out of second chamber 120. Alternatively ratchet 138 may comprise a stop notch at its lowest end to prevent plunger 130 from being easily withdrawn. At the end of stage 5, second chamber 120 has therefore been filled with anticoagulant 540 and first chamber 110 remains filled with physiological solution 510 and syringe 150 is disconnected from the container of anticoagulant.

Figure 5I:
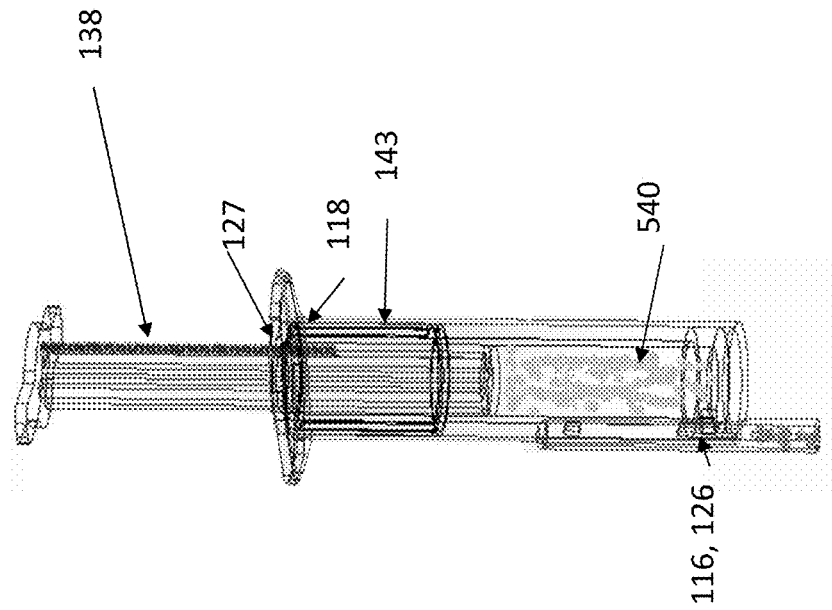
Figure 5H:
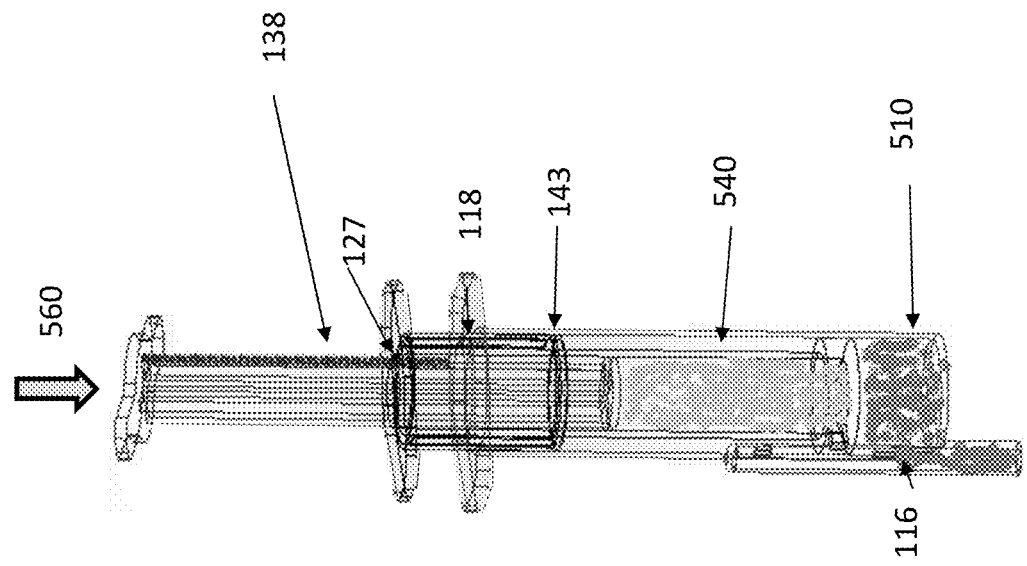
Figure 5M:
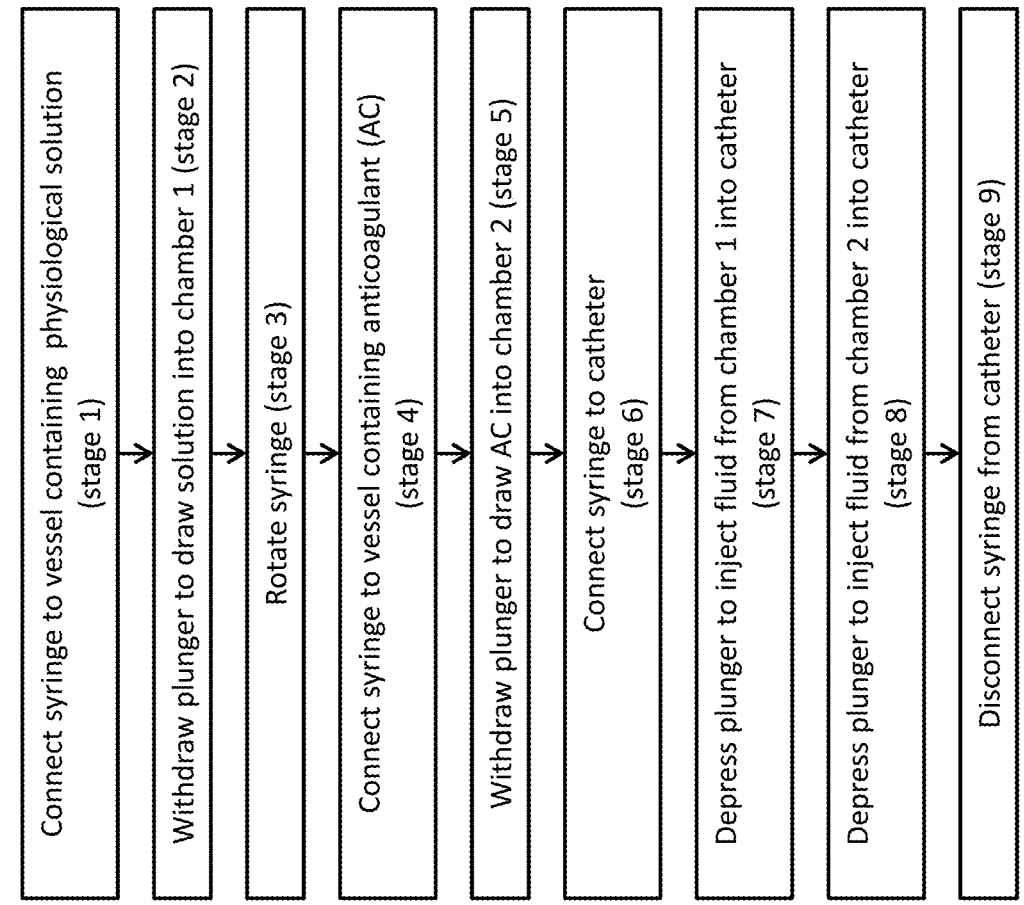

In stage 6, syringe 150 is connected to a catheter (not shown). In stage 7, as shown in FIGS. 5H-5I the physiological solution in first chamber 110 is injected into the catheter. Plunger 130 is depressed in the direction as shown by arrow 560. Fourth ratchet 143 is smooth and therefore provides no resistance compared to second ratchet 138 and second chamber 120 now descends into first chamber 110 and plunger stopper 125 is sealably engaged with the inner walls of first chamber 110 creating positive pressure and pushing the physiological solution 210 out of first chamber 110 through first port 116 into adaptor tube 114 and out of adaptor tip 115 into the attached catheter (not shown). When plunger stopper 125 reaches the bottom of first chamber 110, it can no longer be pushed any further. At the end of stage 7, first chamber 110 is emptied of the physiological solution 510, second chamber remains filled with anticoagulant 540, and first port 116 is aligned with third port 126.

In stage 8, as shown in FIGS. 5J-5L the anticoagulant 540 in second chamber 120 is injected into the catheter. Plunger 130 is depressed in the direction as shown by arrow 550. Since second chamber 120 cannot descend further into first chamber 110, the pressing force on plunger 130 overcomes the resistance of second ratchet 138 and plunger 130 now descends into second chamber 120 and plunger stopper 131 is sealably engaged with the inner walls 120I of second chamber 120 creating positive pressure and pushing the anticoagulant 540 out of second chamber 120 through third port 126 and first port 116 into adaptor tube 114 and out of adaptor tip 115 into the attached catheter (not shown). When plunger stopper 131 reaches the bottom of second chamber 120, it can no longer be pushed any further.

In stage 9 the syringe is disconnected from the catheter and is preferably discarded.

Figure 6:
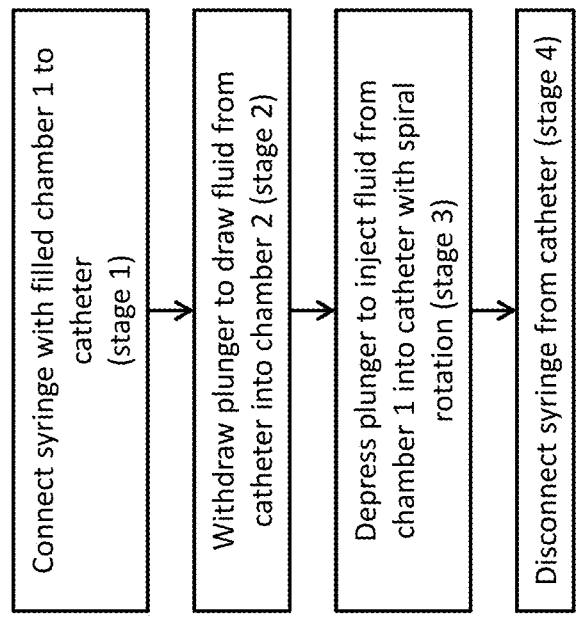
FIG. 6 is a flow diagram for use of a syringe with spiral rotation according to at least some embodiments of the present disclosure.

Reference is now made to FIG. 6 which is a flow diagram of use of a spiral ratchet syringe according to at least some embodiments of the present disclosure. The process of FIG. 6 relates to connection of a CVC (Central Venous Catheter) to a dialysis machine or any process requiring suction followed by injection of different fluids. The method of FIG. 6 utilizes syringe 160 comprising spiral ratchet 162.

First chamber 110 is preferably provided filled with physiological solution which as a non-limiting example is preferably 0.9% saline. Second port 117 is aligned with third port 126. In stage 1, syringe 160 is connected to a catheter (not shown) and in stage 2, plunger 130 is pulled outward from syringe 160. Since notch 164 is at the front end of spiral ratchet 162 and is blocked from moving further, second chamber 120 will not be pulled outward from first chamber 110. The pulling force on plunger 130 will thus pull plunger 130 outwards from second chamber 120 and second notch 127 will slide/click along second ratchet 138. Since plunger stopper 131 is sealably engaged with the inner wall 120I of second chamber 120, negative pressure will be created inside second chamber 120 and since third port 126 is in fluid communication with adaptor tube 114 through second port 117, biological fluid such as blood will be drawn through adaptor tube 114 through second port 117 and third port 126 into second chamber 120. It should be appreciated that no fluid is drawn into first chamber 110 as no negative pressure is created inside first chamber 110 since second chamber 120 does not move relative to first chamber 110.

Plunger 130 is preferably withdrawn until a desired volume of fluid has been drawn into second chamber 120. Plunger 130 is pulled out and second notch 127 preferably makes audible sounds as it moves along the notches of second ratchet 138. Optionally each notch of ratchet 138 represents a particular measurement such that the amount of fluid that is drawn into the syringe 100 can be measured. Each notch on ratchet 138 preferably represents 0.1 cc. Optionally first chamber 110 and second chamber 120 each have markings to indicate the volume of fluid therein.

As above, inner wall 120I is preferably tapered such that plunger 130 is prevented from being pulled out of second chamber 120. Alternatively ratchet 138 may comprise a stop notch at its lowest end to prevent plunger 130 from being easily withdrawn. Further, for connection applications, ratchet 138 is unidirectional such that following withdrawal, plunger 130 cannot be pushed into second chamber 120. At the end of stage 2, second chamber 120 has therefore been filled with fluid and first chamber 110 remains filled with physiological solution.

In stage 3, the physiological solution in first chamber 110 is injected into the catheter. Plunger 130 is depressed and as above, second ratchet 138 prevents plunger 130 from being pushed into second chamber 120 and the pressing force therefore results in second chamber 120 descending into first chamber 110. Plunger stopper 125 is sealably engaged with the inner walls of first chamber 110 creating positive pressure and pushing the physiological solution out of first chamber 110 through first port 116 into adaptor tube 114 and out of adaptor tip 115 into the attached catheter (not shown). As second chamber 120 descends, angled notch 164 engages with spiral ratchet 162 and second chamber 120 rotates with respect to first chamber 110 such that third port 126 rotates away from second port 117. When plunger stopper 125 reaches the bottom of first chamber 110, it can no longer be pushed any further. Alternatively, a measured amount of physiological solution is injected based on volume markings on the side of first chamber 110. At the end of stage 3, first chamber 110 is emptied of the physiological solution and second chamber 120 remains filled with fluid.

In stage 4 the syringe is preferably disconnected from the catheter and is preferably discarded.

Syringe 160 is preferably also used for catheter disconnection scenarios similar to those described with reference to FIGS. 5A-5M.

Reference is now made to FIGS. 7A-7H which are schematic illustrations of a syringe according to at least some embodiments of the present disclosure. As shown in FIGS. 7A-7E, a syringe 700 comprises a first chamber 710, second chamber 720, and plunger 730.

First chamber 710 is a cylindrical hollow chamber open at opening 712 at chamber flange 719. First chamber 710 comprises an inner tube 750 extending from the base 752 of first chamber 710 and defining an opening 754 in base 752 at the lower end of the inner tube 750. Tube opening 754 provides for fluid communication between tube 750 and outlet chamber 756. Outlet chamber 756 is in fluid communication with adaptor tube 714.

Figure 7A:
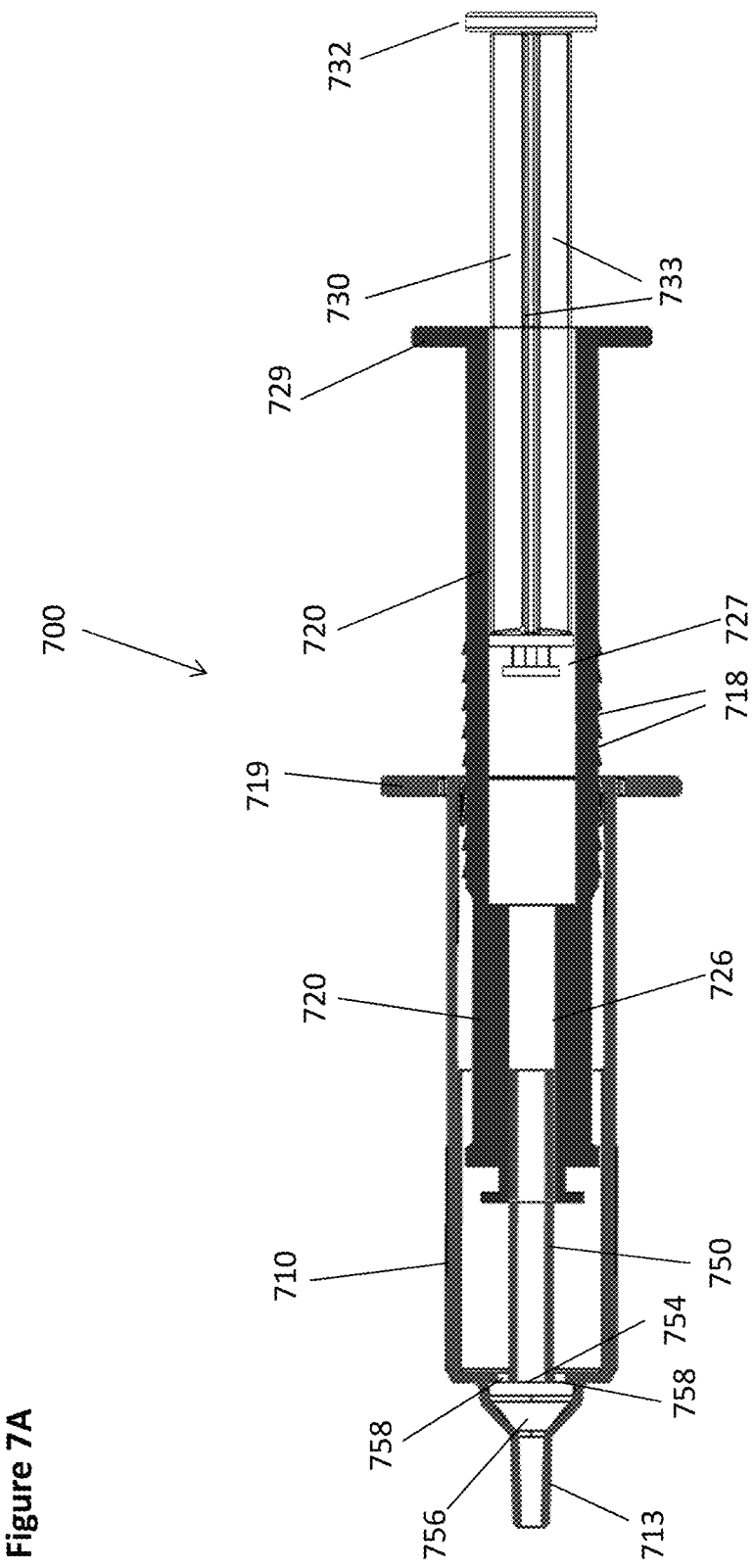
Figure 7C:
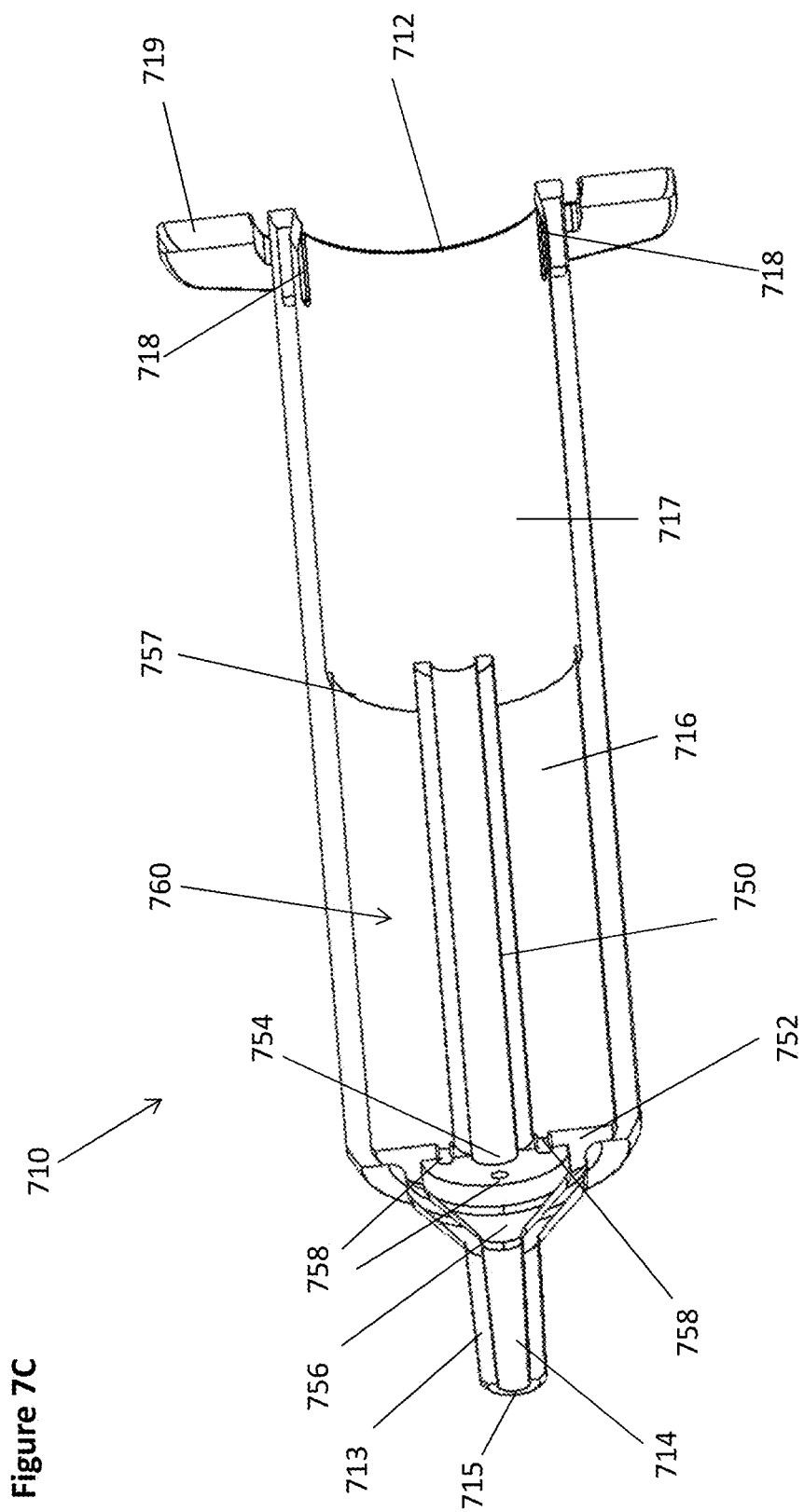
Figure 7D:
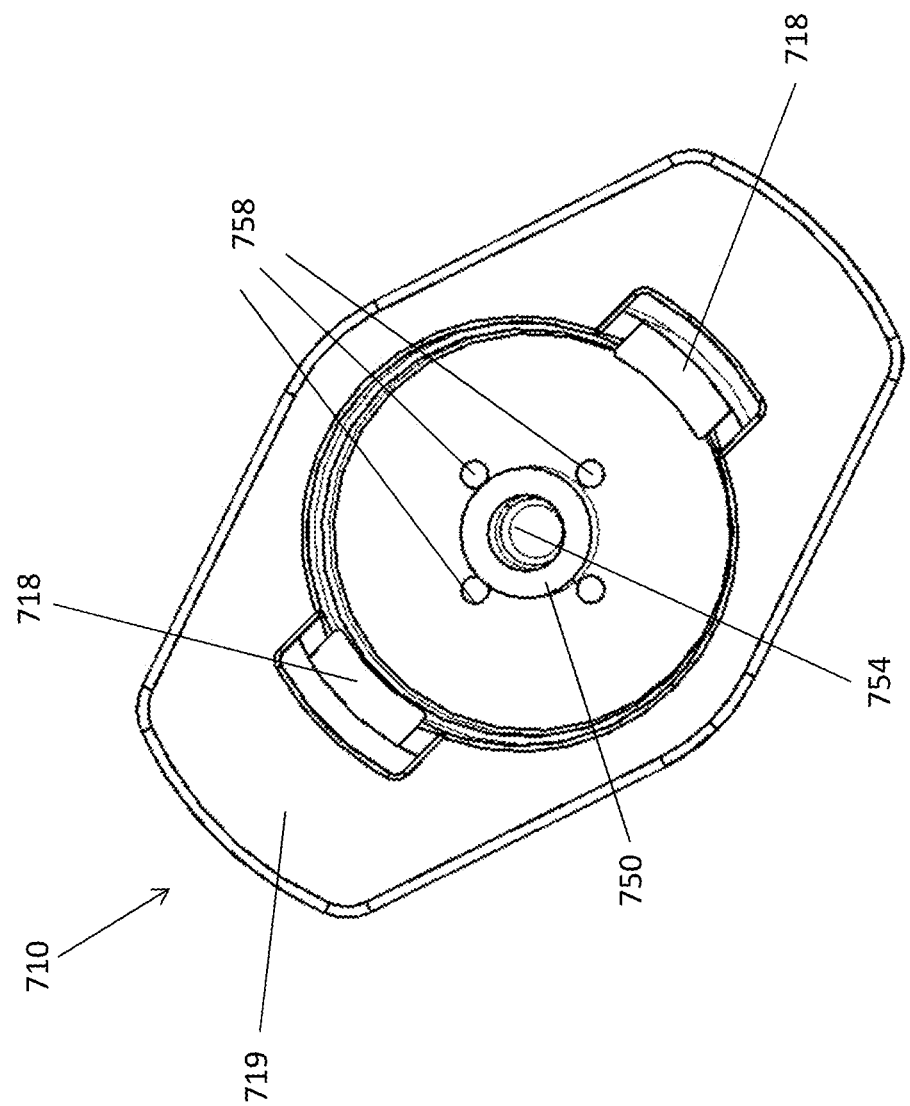
Figure 7E:
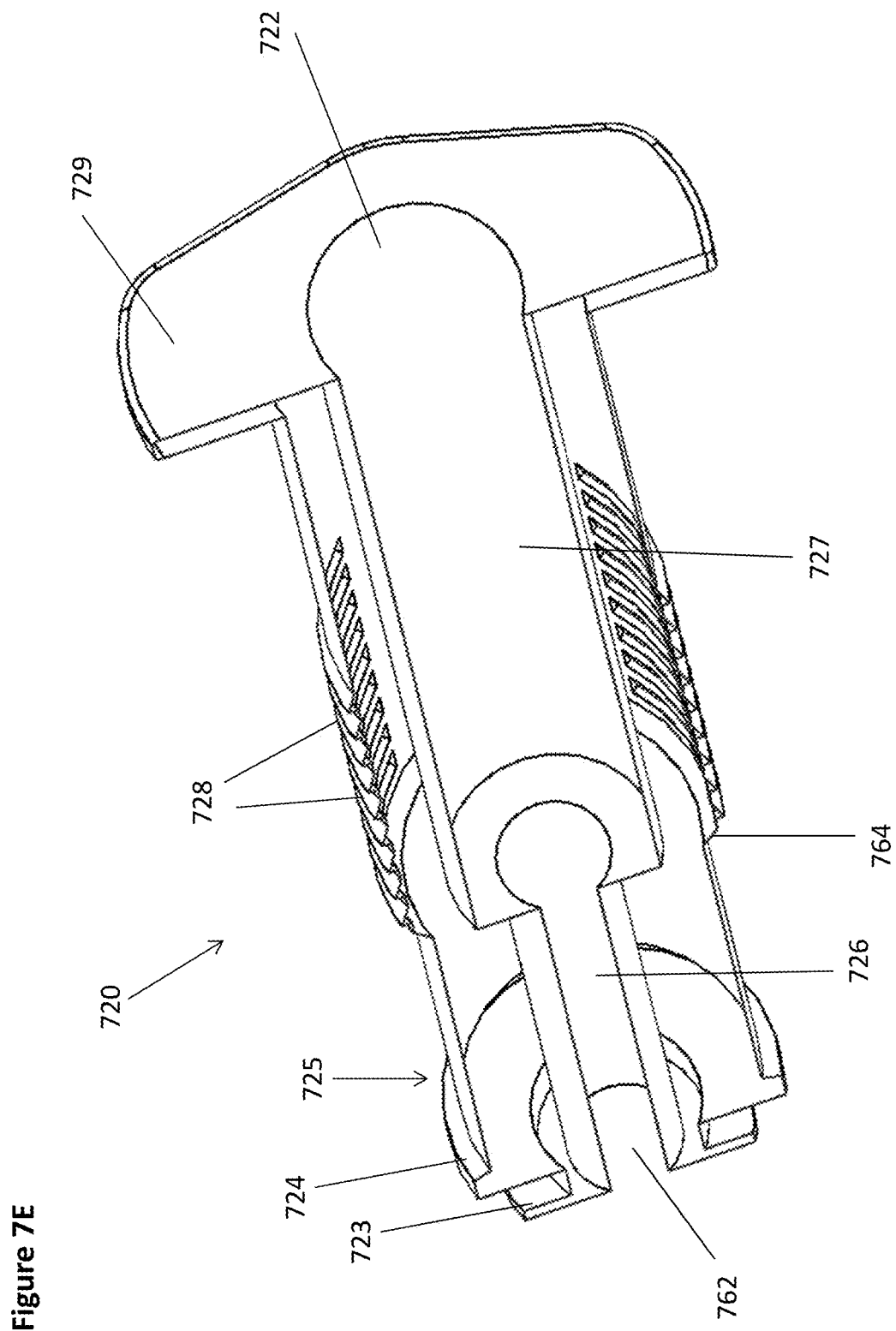

Base 752 further comprises at least one port 758 in base 752 providing fluid communication between outlet chamber 756 and the inner volume 760 of first chamber 710. As shown in FIG. 7D, base 752 comprises four ports 758 but this number should not be considered limiting and optionally more or less ports of the same or different sizes may be provided.

First chamber 710 comprise adaptor 713 for attachment to a catheter (not shown) or other medical device or receptacle (not shown). Adaptor 713 comprises adaptor tube 714 which is open at adapter tip 715. Adaptor 713 has dimensions of syringe adaptors as known in the art including but not limited to Luer Lock tapered termination. In some embodiments, chamber flange 719 comprises notches 718 for engaging with ratchet 728 of second chamber 720.

Second chamber 720 is a cylindrical hollow chamber open at opening 722 at chamber flange 729. In some embodiments, second chamber 720 comprises leading ring 723 and trailing ring 724 of plunger stopper 725. Leading ring 723 is sized so as to seal ports 758 when it makes contact with base 752 by covering them. Trailing ring is sized so as to firmly engage the lower inner surface 716 of first chamber 710. Rings 723, 724 comprise rubber, silicone or other material known in the art for use in syringe plunger stoppers. Second chamber 720 is open at opening 762 in a bottom end of second chamber 720 where opening 762 extends through plunger stopper 725 so that second chamber 720 can fit over inner tube 750.

Second chamber 720 has a wider upper inner chamber 727 and a narrower lower inner chamber 726. Inner chamber 726 is sized so as to sealably fit over inner tube 750 when second chamber 720 is placed inside of first chamber 710. The diameter of second chamber 720 is preferably tapered as known in the art on its upper inner surface 727 near opening 722 to provide greater resistance and prevent easy removal of inserted plunger 730.

In some embodiments, second chamber comprises linear ratchet 728 for engaging with notch 718 of first chamber 710. The diameter of upper wall 727 of second chamber 720 is fixed along the majority of its length so as to engage plunger 730. The diameter of inner upper wall 727 is tapered at its rear end as is known in the art such that plunger 730 cannot be easily pulled out.

Plunger 730 is formed as a typical plunger as known in the art. The body of plunger 730 comprises up to four parallel blades 733 running the length of plunger 730. Alternatively more blades or no blades are provided. Plunger stopper 731 is affixed to the front of plunger 730. Stopper 731 is sized so as to sealably engage the inner upper wall 727 of second chamber 720. Plunger 730 comprises a plunger head 732 at its rear end formed for pushing plunger 730 into second chamber 720.

First chamber 710 has a wider upper inner chamber 717 and a narrower lower inner chamber 716. Wider upper inner chamber 717 has a dimeter wide enough to accommodate linear ratchet 728. Where upper chamber 717 and lower chamber meet, ridge 757 slopes between upper chamber 717 and lower chamber 716. First chamber 710 is preferably tapered as known in the art at the upper part of inner surface 716 to provide greater resistance and prevent removal of inserted second chamber 720. Linear ratchet 728 preferably comprises a stop mechanism at its lower end to prevent removal of second chamber 720 from within first chamber 710 and to prevent lower inner surface 726 from disconnecting with inner tube 750. The stop mechanism may for example be a square tooth or opposite facing tooth on ratchet 728 that cannot be pulled past notch 118.

Figure 7F:
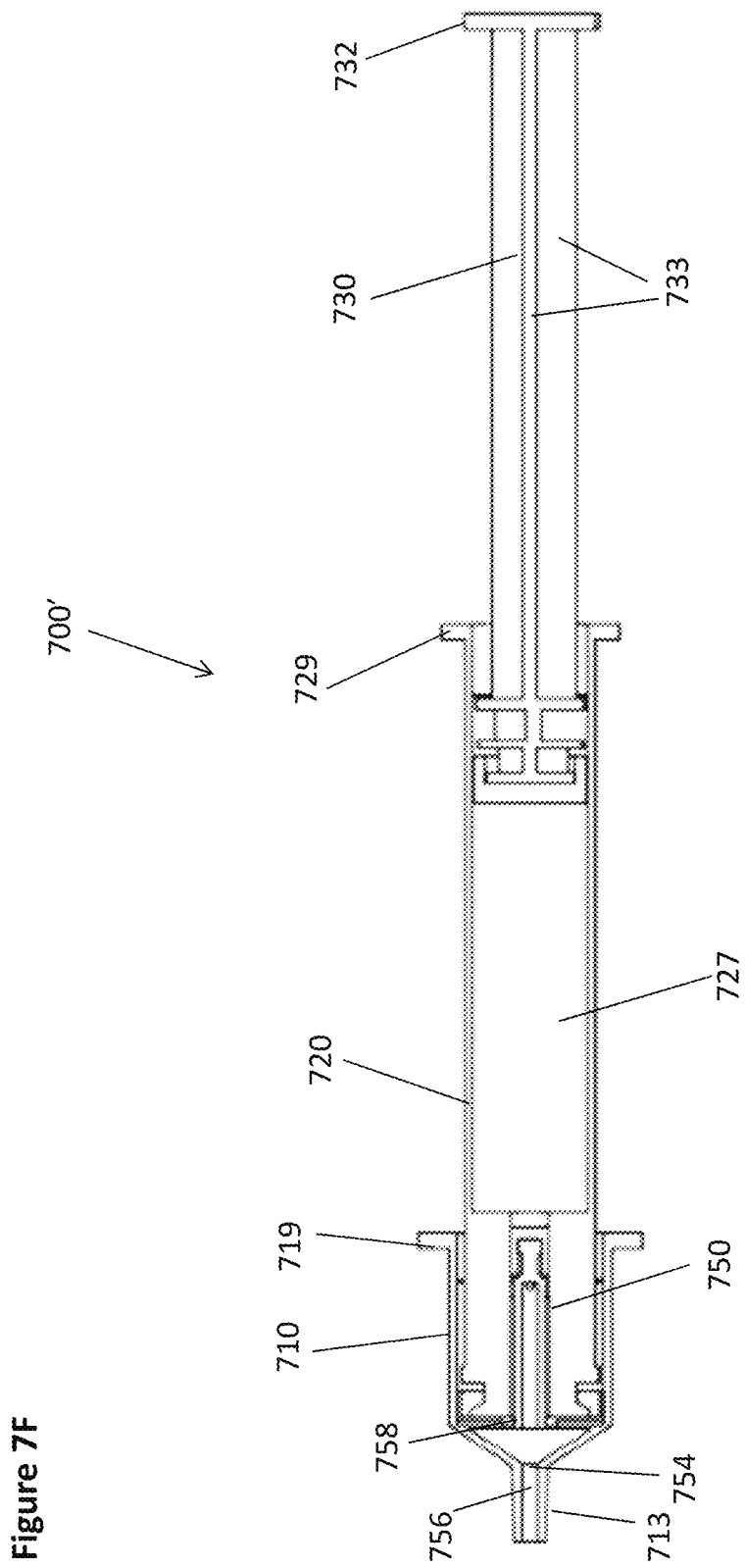
Figure 7G:
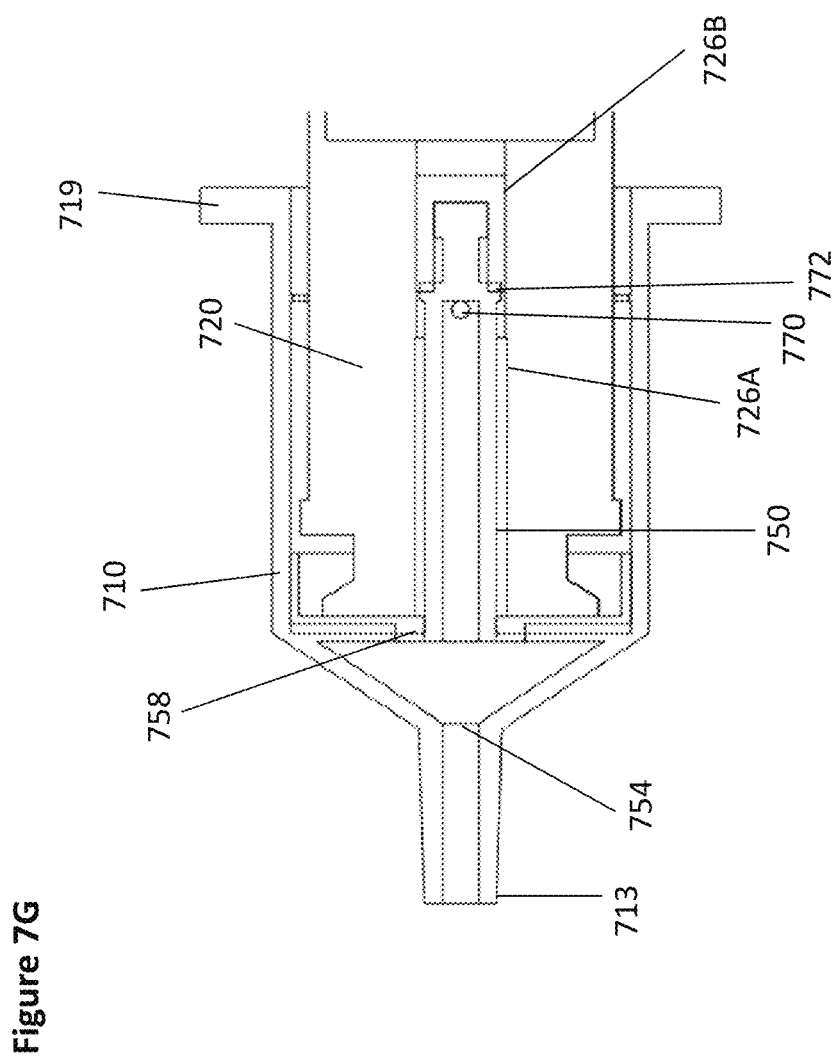
Figure 7H:
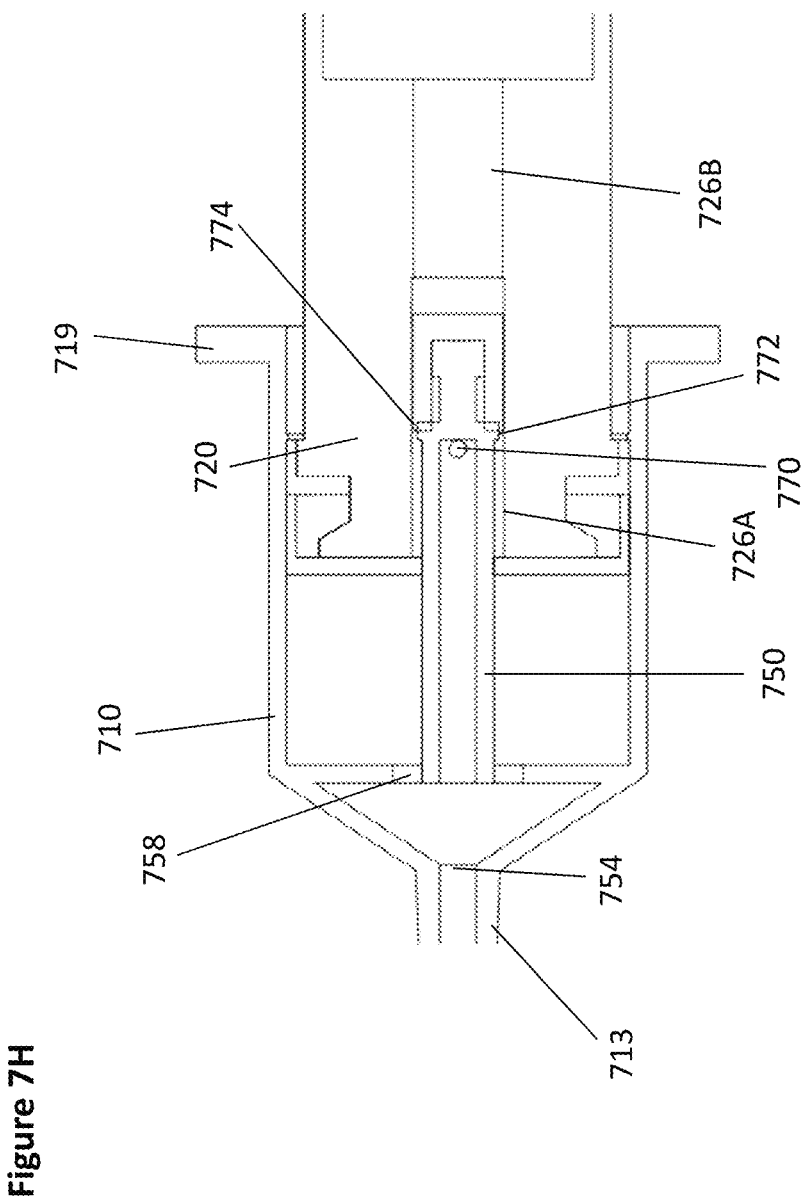

FIGS. 7F-7H show alternative embodiments of syringe 700 herein designated syringe 700'. Syringe 700' is structurally similar to syringe 700 but includes an additional flow safety mechanism for preventing mixing of the contents of first chamber 710 and second chamber 720. Mixing of the contents of first chamber 710 and second chamber 720 in syringe 700 is unlikely to occur due to the structure of syringe 700 but regulatory authorities may require such a flow safety mechanism as depicted in FIGS. 7F-7H.

Inner tube 750 of syringe 700' comprises an upper port 770 for flow of fluids between inner tube 750 and second chamber 720 and an upper ring 772 for preventing or allowing flow of fluids between inner tube 750 and second chamber 720. The lower inner chamber 726 of second chamber 720 comprises a narrower portion 726B and a wider portion 726A.

As shown in FIG. 7G, when second chamber 720 is fully inserted into first chamber 710, and also when second chamber 720 is partially withdrawn from first chamber 710 but with upper ring 772 still engaging narrower portion 726B, no fluid can flow between inner tube 750 and second chamber 720.

As shown in FIG. 7H, when second chamber 720 is withdrawn from first chamber 710 such that upper ring 772 no longer engages narrower portion 726B, but rather sits within wider portion 726A, a gap 774 between upper ring 772 and wider portion 726A allows fluid to flow between inner tube 750 and second chamber 720 via upper port 770.

To further prevent mixing of contents of first chamber 710 and second chamber 720 in syringe 700', tube opening 754 is in direct fluid communication with adaptor tube 714 with no outlet chamber 756.

Figure 8A:
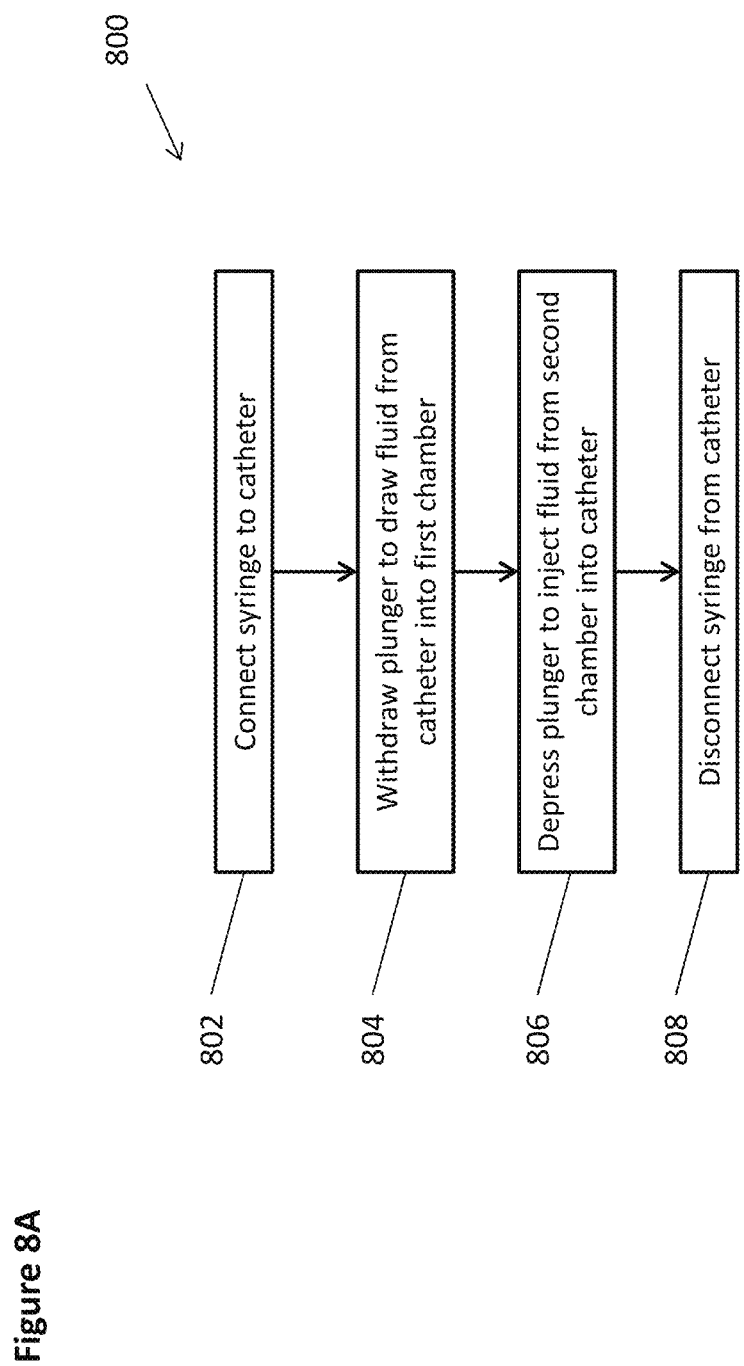
FIGS. 8A and 8B-8D are respectively a flow diagram and schematic illustrations showing operation of a syringe according to at least some embodiments of the present disclosure.
Figure 8B:
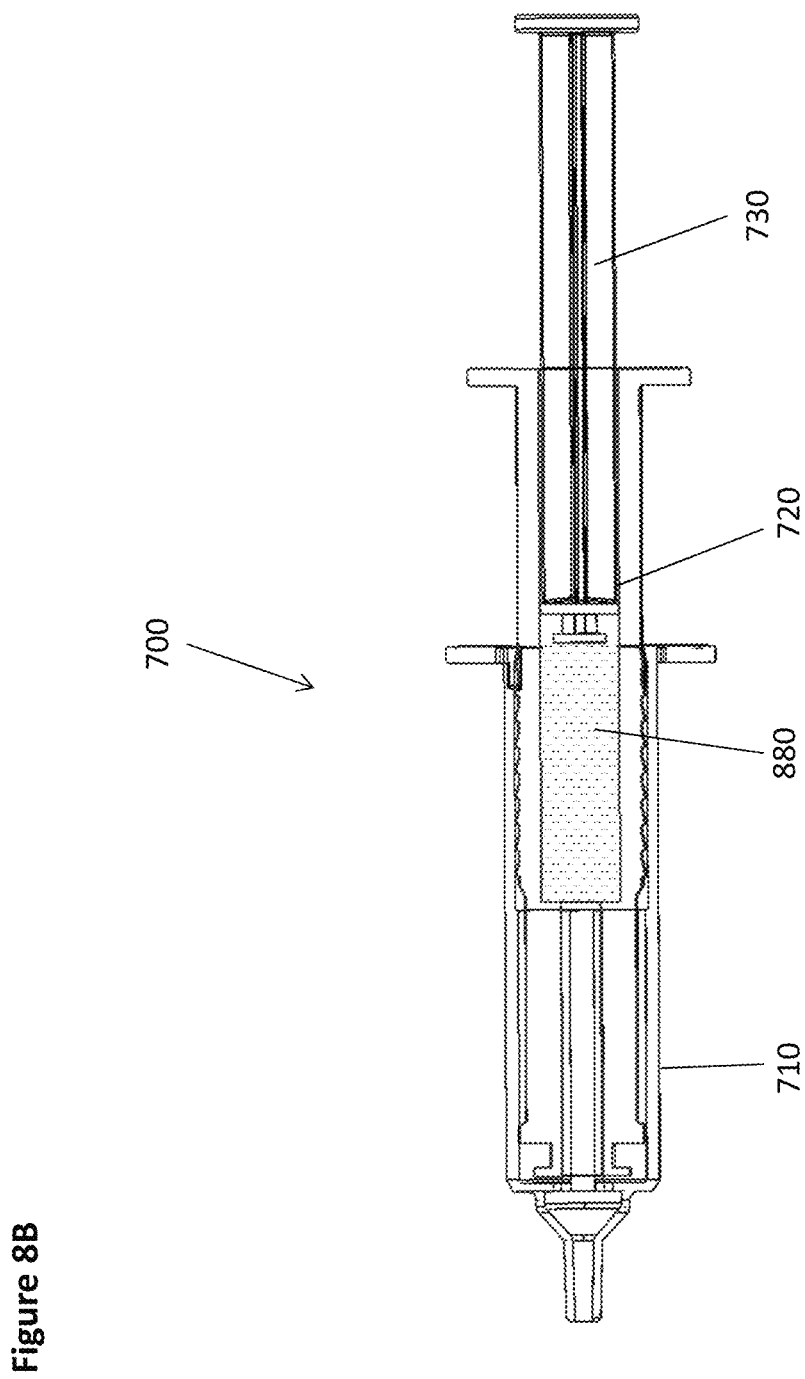

Reference is now made to FIGS. 8A and 8B-8D which are respectively a flow diagram and schematic illustrations showing operation of a syringe according to at least some embodiments of the present disclosure. The process 800 of FIGS. 8A-8D relates to connection of a CVC (Central Venous Catheter) or any catheter or medical tube to a dialysis machine or any process requiring suction followed by injection of different fluids. As shown in FIG. 8B, the syringe 700 of FIGS. 7A-7E is provided with second chamber 720 inserted fully into first chamber 710 and plunger 730 partially inserted into second chamber 720 where second chamber 720 is pre-filled with physiological solution 880. Syringe 700 is shown ready for use in FIG. 8B. Alternatively syringe 700' of FIGS. 7F-7H may be used for process 800.

Plunger stopper 725 sealably engages the inner walls 716 of first chamber 710 and second chamber 720 thus functions as a syringe plunger for first chamber 710. Plunger head 731 sealably engages the inner walls 727 of second chamber 720 and thus plunger 730 functions as a syringe plunger for second chamber 720. First notch 718 is engaged with ratchet 728.

Figure 8C:
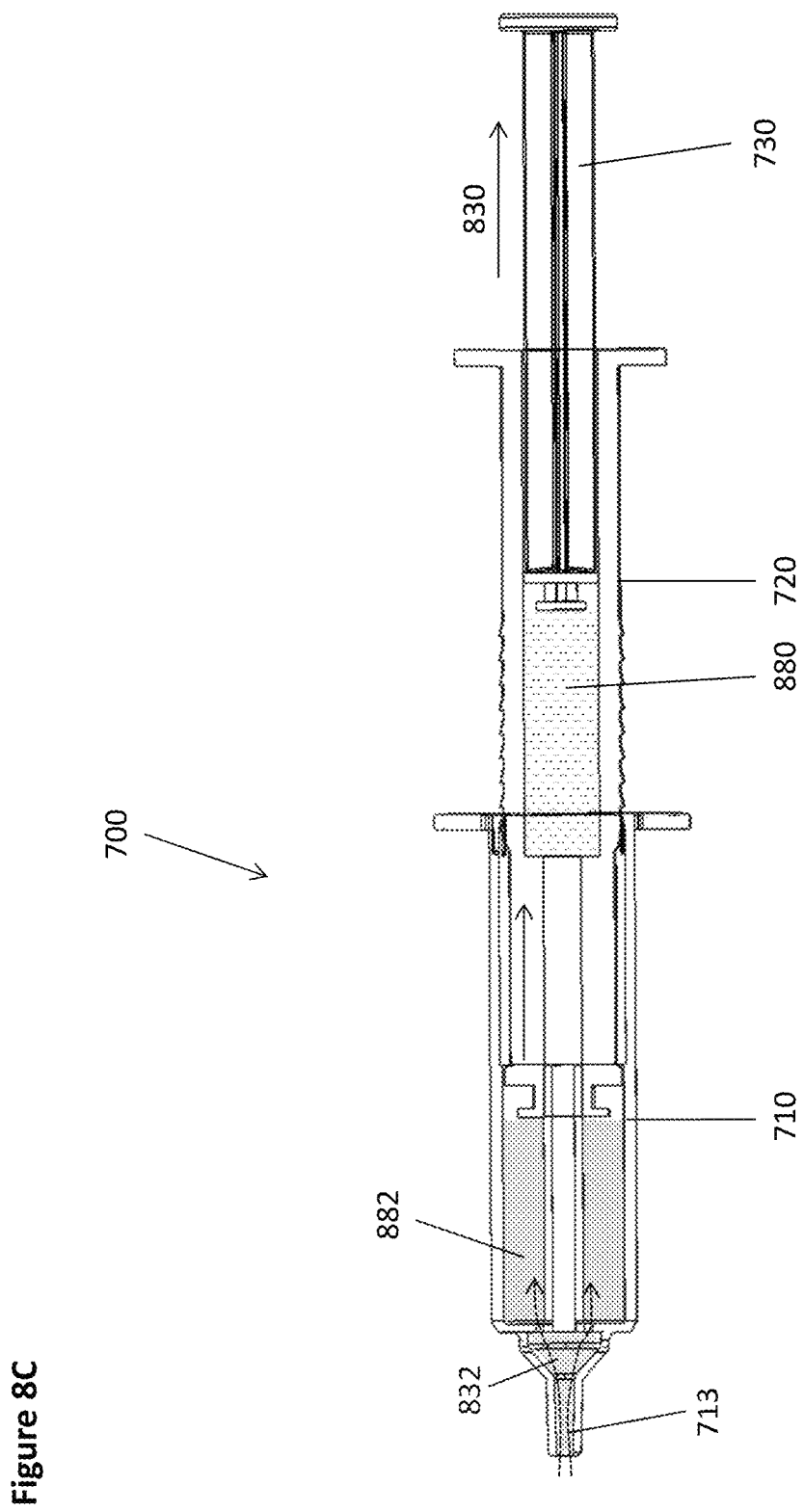

In step 802, syringe 700 is connected at adaptor tip 715 to a catheter (not shown). In step 804, as shown in FIG. 8C, plunger 730 is pulled outward from syringe 700 in the direction as shown by arrow 830. Since plunger 730 is prevented from being pulled out of second chamber 720 by the tight circumference of surface 727, the result is that second chamber 720 is pulled out of first chamber 710. As second chamber 720 is pulled out of first chamber 710, negative pressure is created inside the inner volume 760 of first chamber 710 and blood (or other fluid) 882 is drawn into inner volume 760 via adaptor tube 714, then outlet chamber 756, then ports 758 as shown by arrows 832. Since no pressure change is created in second chamber 720 (since plunger 730 does not move inside second chamber 720), no blood is sucked into inner tube 750. Alternatively the safety mechanism of FIGS. 7F-7H ensures that no blood is sucked into inner tube 750 or second chamber 720.

As second chamber 720 is pulled out of first chamber 710, ratchet 728 clicks against notch 718. Since the teeth of ratchet 728 face against the direction of insertion of second chamber 720, second chamber 720 can no longer be pushed into first chamber 710, thus preventing expulsion of the drawn blood 882. Further, second chamber 720 cannot be drawn out of first chamber 710 due to the stop at the end of linear ratchet 728, to therefore prevent inner surface 726 of second chamber 720 from disconnecting with inner tube 750.

Plunger 730 is preferably withdrawn until a desired volume of blood 882 has been drawn into first chamber 710 or until ratchet 728 prevents further withdrawal. Optionally each notch of ratchet 728 represents a particular measurement such that the amount of fluid that is drawn into the syringe 700 can be measured. Each notch on ratchet 728 preferably represents 0.1 cc. Optionally first chamber 710 and second chamber 720 each have markings to indicate the volume of fluid therein. At the end of step 804, first chamber 710 has therefore been filled with blood 882 and second chamber 720 remains filled with physiological solution 880.

Figure 8D:
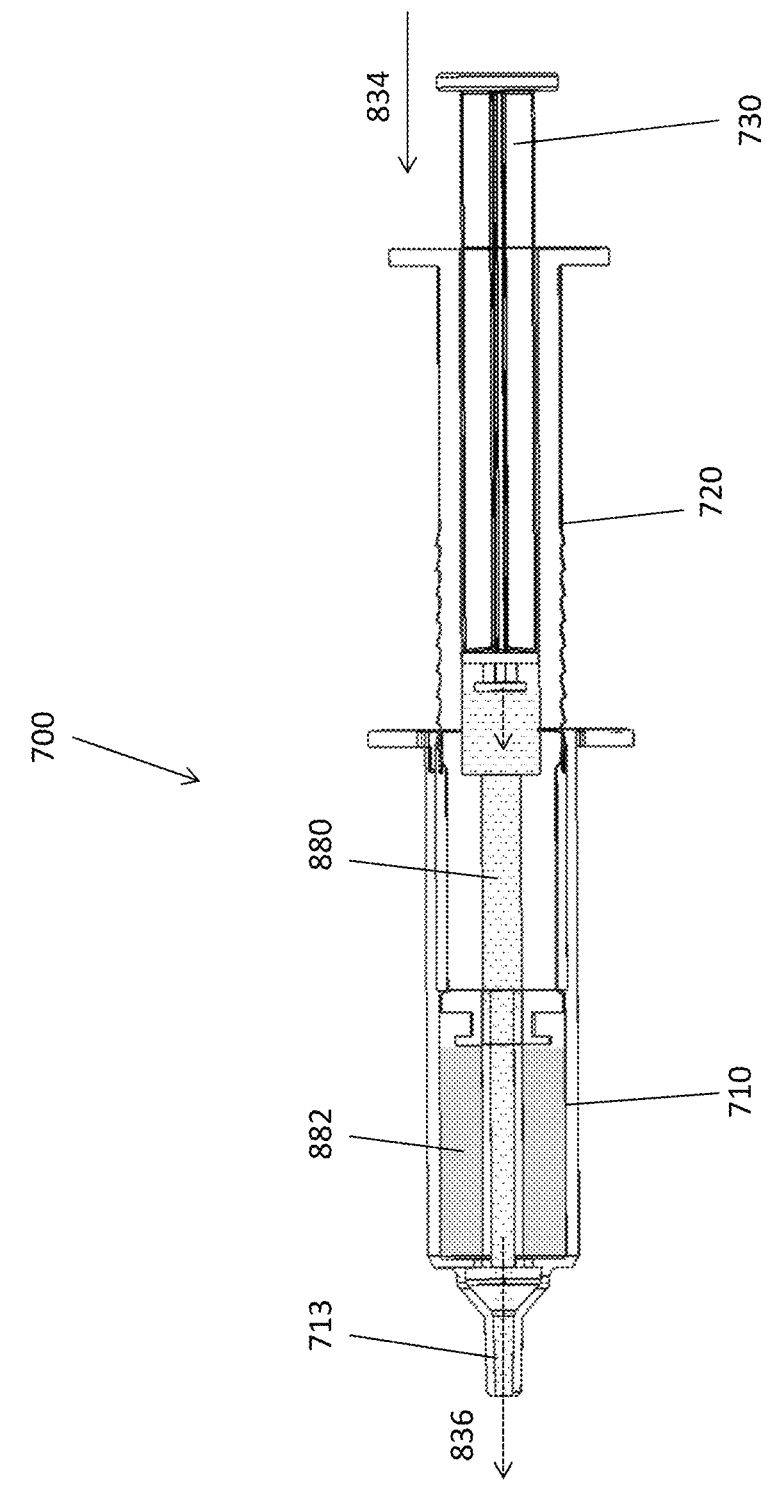

In step 806, as shown in FIG. 8D the physiological solution in second chamber 720 is injected into the catheter.

Plunger 730 is depressed in the direction as shown by arrow 834. As above, ratchet 728 prevents second chamber 720 from being pushed into first chamber 710 and plunger 730 now descends into second chamber 720 and plunger stopper 731 is sealably engaged with the upper inner walls 727 of second chamber 720 creating positive pressure and pushing the physiological solution 880 out of second chamber 720 through lower inner chamber 726, through inner tube 750, through opening 754, through outlet chamber 756, and through adaptor tube 714 into the attached catheter (not shown). When plunger stopper 731 reaches the bottom of upper inner chamber 727, it can no longer be pushed any further. At the end of step 806, second chamber 720 is emptied of the physiological solution 880 and first chamber 710 remains filled with blood 882.

In step 808 the syringe 700 is disconnected from the catheter and is preferably discarded. Although process 800 has been described with reference to a dialysis connection, it should be appreciated that syringe 700 and process 800 can be used for any situation requiring drawing of fluid followed by injection of another fluid into the same receptacle.

Optionally, syringe 700 is provided with first chamber 710 filled with solution 880. In such a situation, in step 804 fluid 882 is drawn into second chamber 720, and in step 806, solution 880 is injected from first chamber 710. This alternative is advantageous when small exact amounts of fluid are required to be drawn from the catheter.

Reference is now made to FIGS. 9A-9H which are schematic illustrations of a syringe according to at least some embodiments of the present disclosure. As shown in FIGS. 9A-9E, a syringe 900 comprises a first chamber 910, second chamber 920, and plunger 930. Syringe 900 is the same as syringe 700 but does not comprise a ratchet 728.

First chamber 910 is a cylindrical hollow chamber open at opening 912 at chamber flange 919. First chamber 910 comprises an inner tube 950 extending from the base 952 of first chamber 910 and defining an opening 954 in base 952 at the lower end of the inner tube 950. Tube opening 954 provides for fluid communication between tube 950 and outlet chamber 956. Outlet chamber 956 is in fluid communication with adaptor tube 914.

Figure 9A:
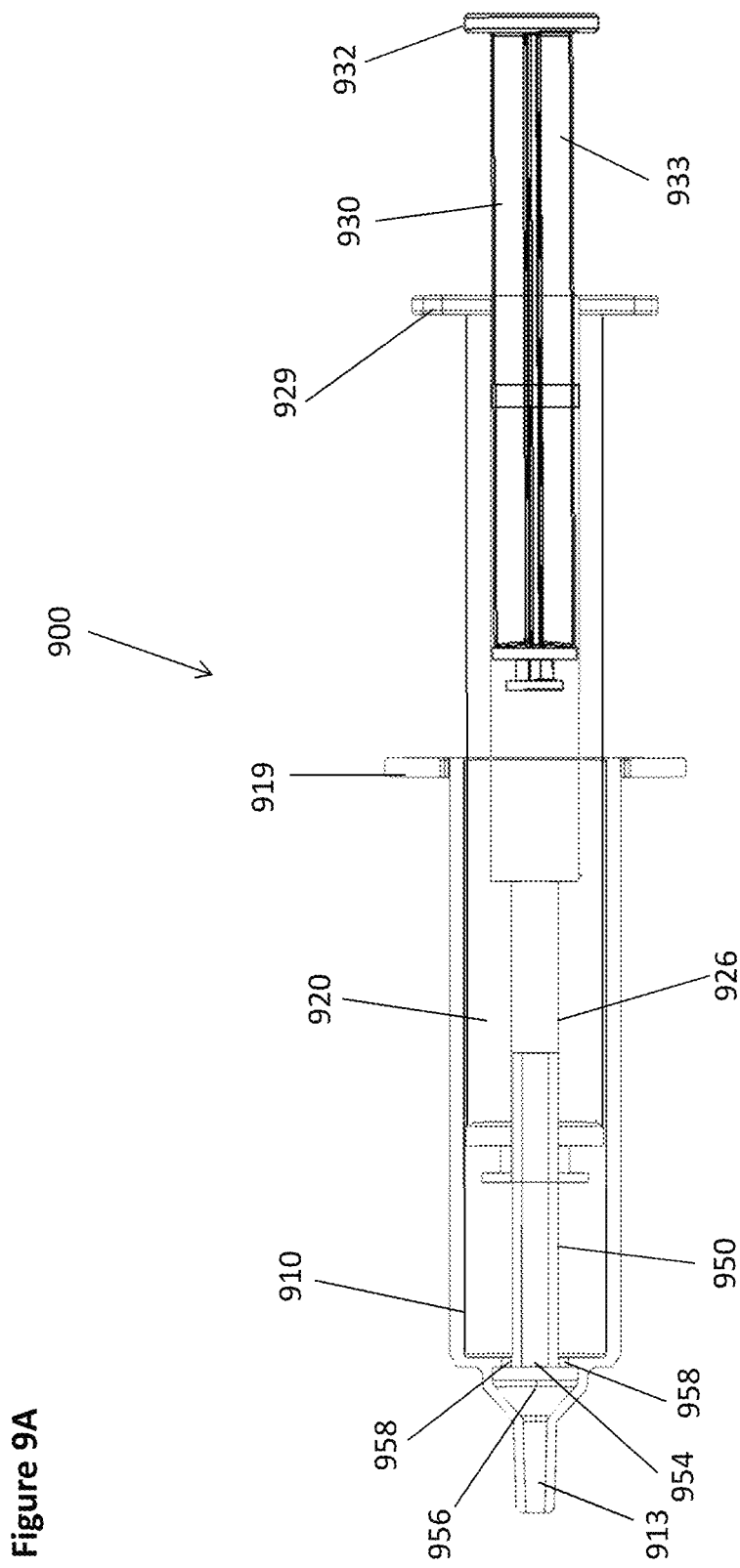
FIGS. 9A-9H are schematic illustrations of a syringe according to at least some embodiments of the present disclosure.
Figure 9B:
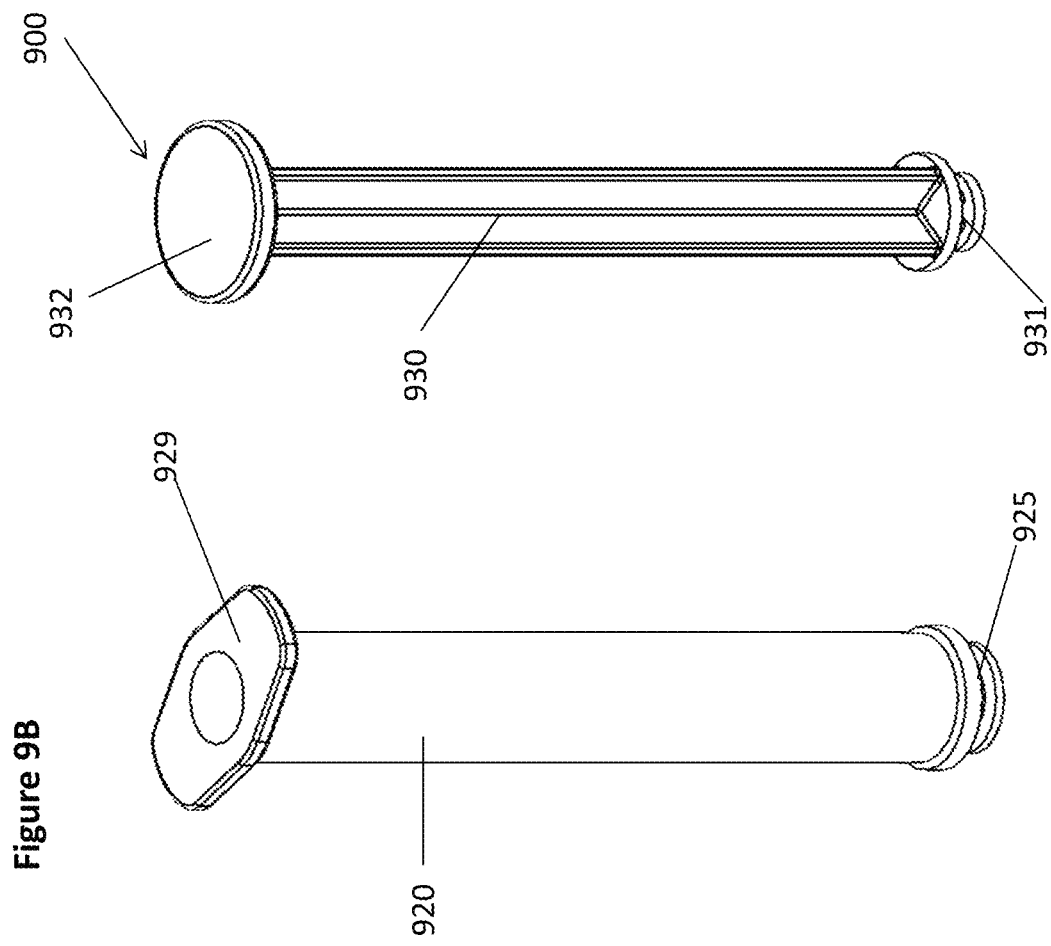
Figure 9B:
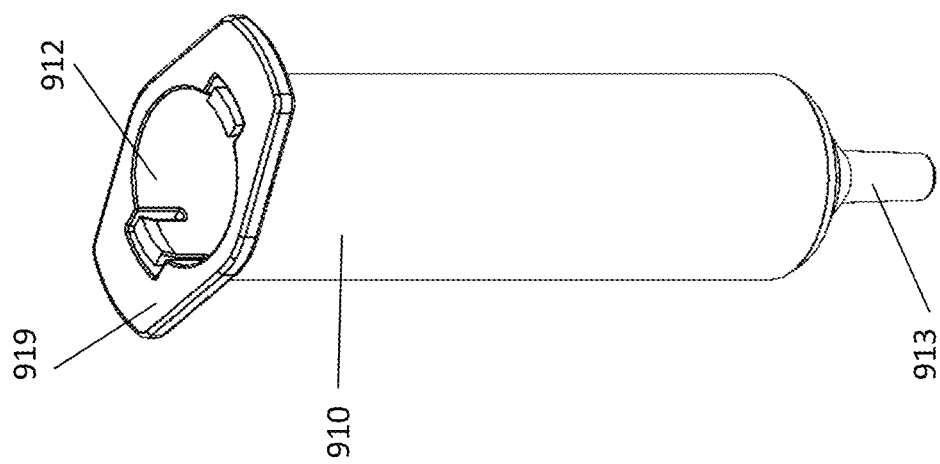
Figure 9C:
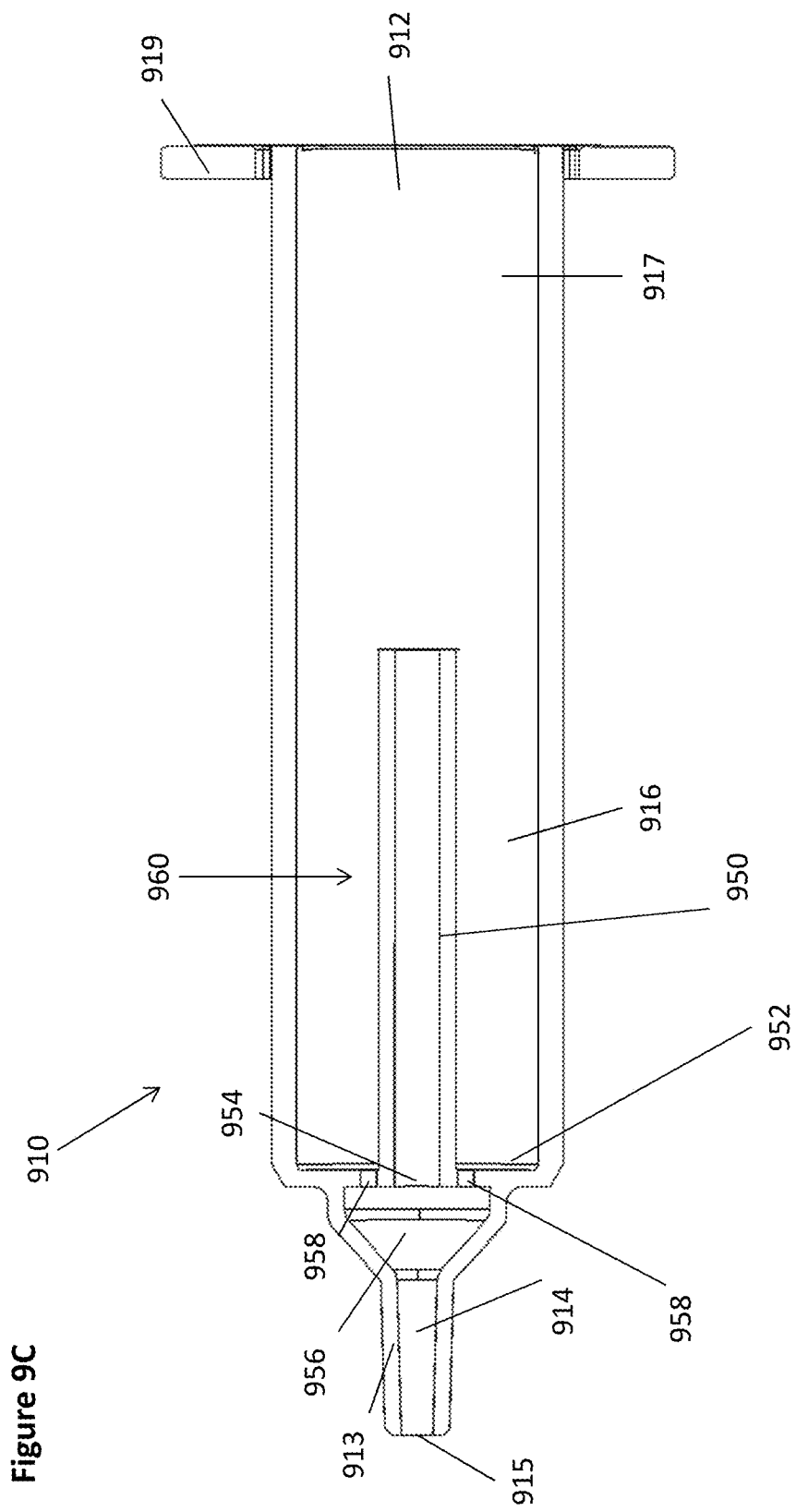
Figure 9D:
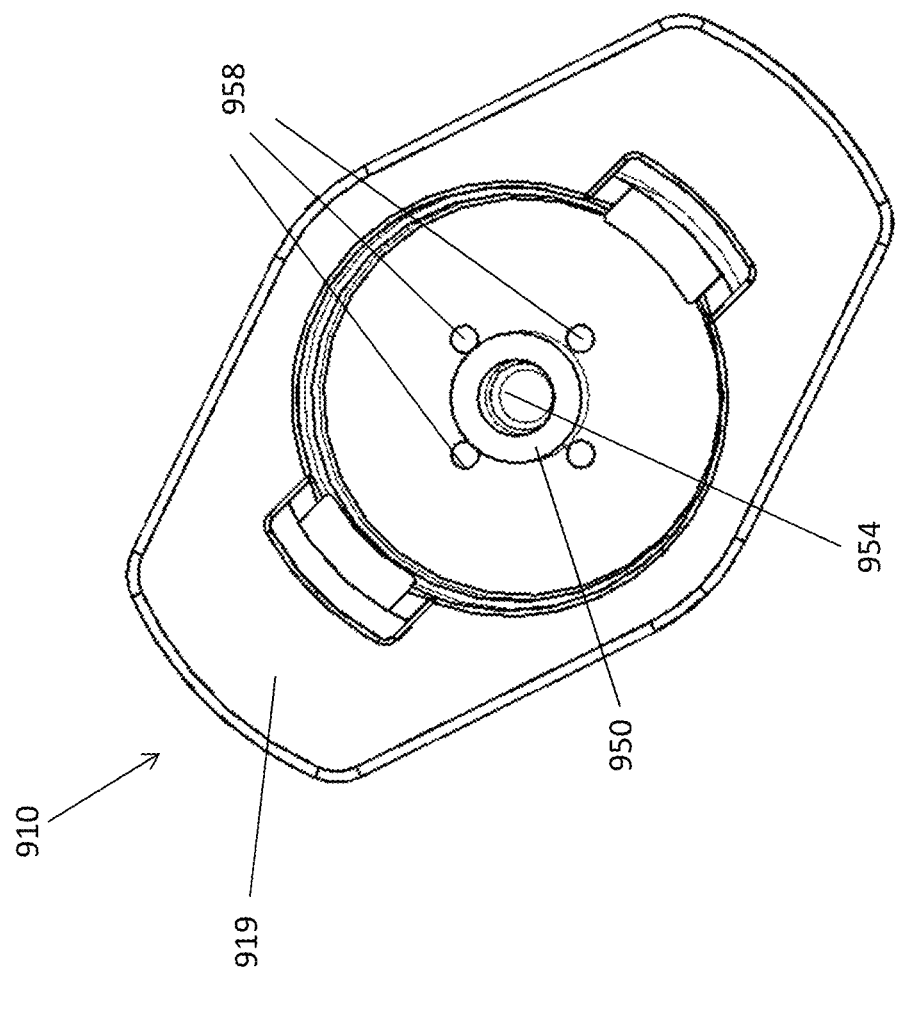
Figure 9E:
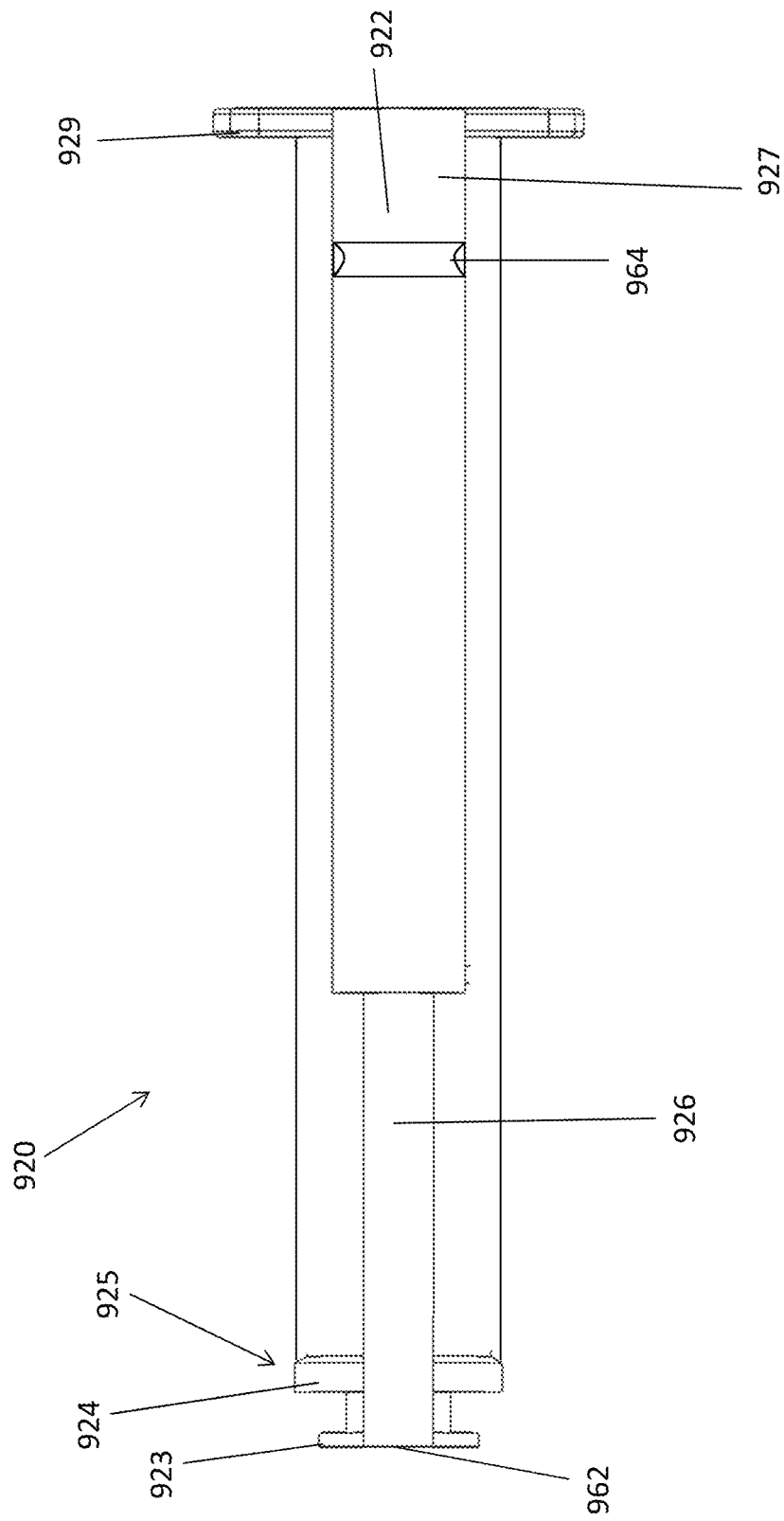

Base 952 further comprises at least one port 958 in base 952 providing fluid communication between outlet chamber 956 and the inner volume 960 of first chamber 910. As shown in FIG. 9D, base 952 comprises four ports 958 but this number should not be considered limiting and optionally more or less ports of the same or different sizes may be provided.

In some embodiments, first chamber 910 is tapered as known in the art on its upper inner surface 917 near opening 912 to provide greater resistance and prevent easy removal of inserted second chamber 920.

First chamber 910 comprise adaptor 913 for attachment to a catheter (not shown) or other medical device (not shown). Adaptor 913 comprises adaptor tube 914 which is open at adapter tip 915. Adaptor 913 has dimensions of syringe adaptors as known in the art including but not limited to Luer Lock tapered termination.

Second chamber 920 is a cylindrical hollow chamber open at opening 922 at chamber flange 929. Second chamber 920 comprises leading ring 923 and trailing ring 924 of plunger stopper 925. Leading ring 923 is sized so as to seal ports 958 when it makes contact with base 952 by covering ports 958. Trailing ring is sized so as to firmly engage the inner surfaces 916 and 917 of first chamber 910. Rings 923, 924 comprise rubber, silicone or other material known in the art for use in syringe plunger stoppers. Second chamber 920 is open at opening 962 in a bottom end of second chamber 920 where opening 962 extends through plunger stopper 925 so that second chamber 920 can fit over inner tube 950.

Second chamber 920 has a wider upper inner chamber 927 and a narrower lower inner chamber 926. Inner chamber 926 is sized so as to sealably fit over inner tube 950 when second chamber 920 is placed inside of first chamber 910. Second chamber 920 is preferably tapered as known in the art on its upper inner surface 927 near opening 922 to provide greater resistance and prevent easy removal of inserted plunger 930. In some embodiments, second chamber 920 comprises ridge 964 for creating greater resistance to insertion of plunger 930 as will be described below.

Plunger 930 is formed as a typical plunger as known in the art. The body of plunger 930 comprises up to four parallel blades 933 running the length of plunger 930. Alternatively more blades or no blades are provided. Plunger stopper 931 is affixed to the front of plunger 930. Stopper 931 is sized so as to sealably engage the inner upper wall 929 of second chamber 920. Plunger 930 comprises a plunger head 932 at its rear end formed for pushing plunger 930 into second chamber 920.

Stopper ring 924 has a diameter that is slightly bigger than the diameter at inner surfaces 917 and 916 such that stopper 924 sealably engages surfaces 916 and 917 preventing fluid from escaping around stopper 925 while allowing stopper 924 to move along surfaces 916 and 917. The "first chamber diameter difference" of stopper 925 to the diameter at surfaces 917 and 916 is optionally up to 1% bigger.

Plunger stopper 931 has a diameter that is slightly bigger than the upper inner walls 927 of second chamber 920 such that stopper 931 sealably engages surface 927 preventing fluid from escaping around stopper 931 while allowing stopper 931 to move along surface 927. The "second chamber diameter difference" of stopper 931 to the diameter at surface 927 is optionally up to 3% bigger.

Moving stopper 931 inside second chamber 920 therefore requires greater effort than moving stopper 925 inside first chamber 910 since stopper 931 has a higher diameter difference than stopper 925. The "diameter difference ratio" of first chamber diameter difference to second chamber diameter difference is preferably 1:3. The diameter difference ratio of first chamber diameter difference to second chamber diameter difference is optionally 1:4.

Figure 9F:
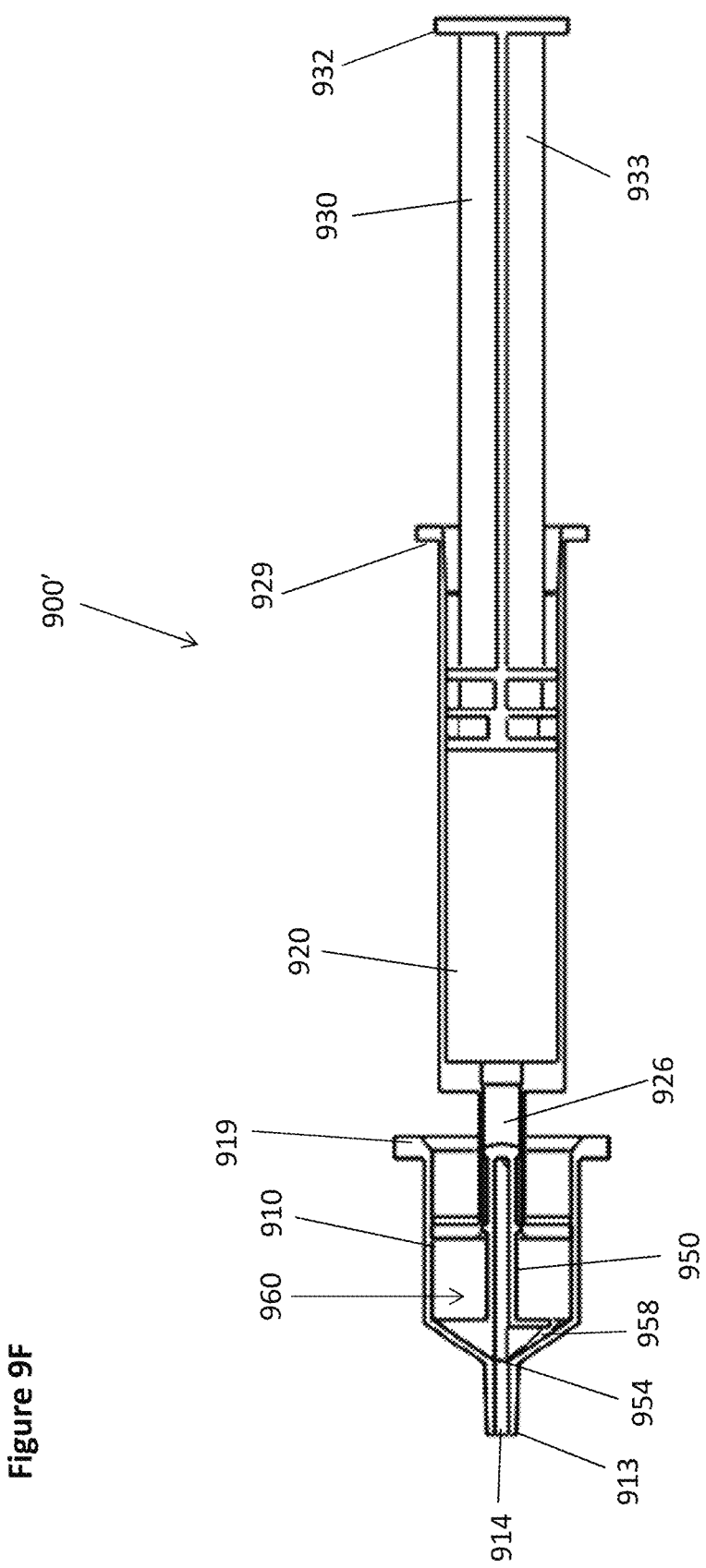
Figure 9G:
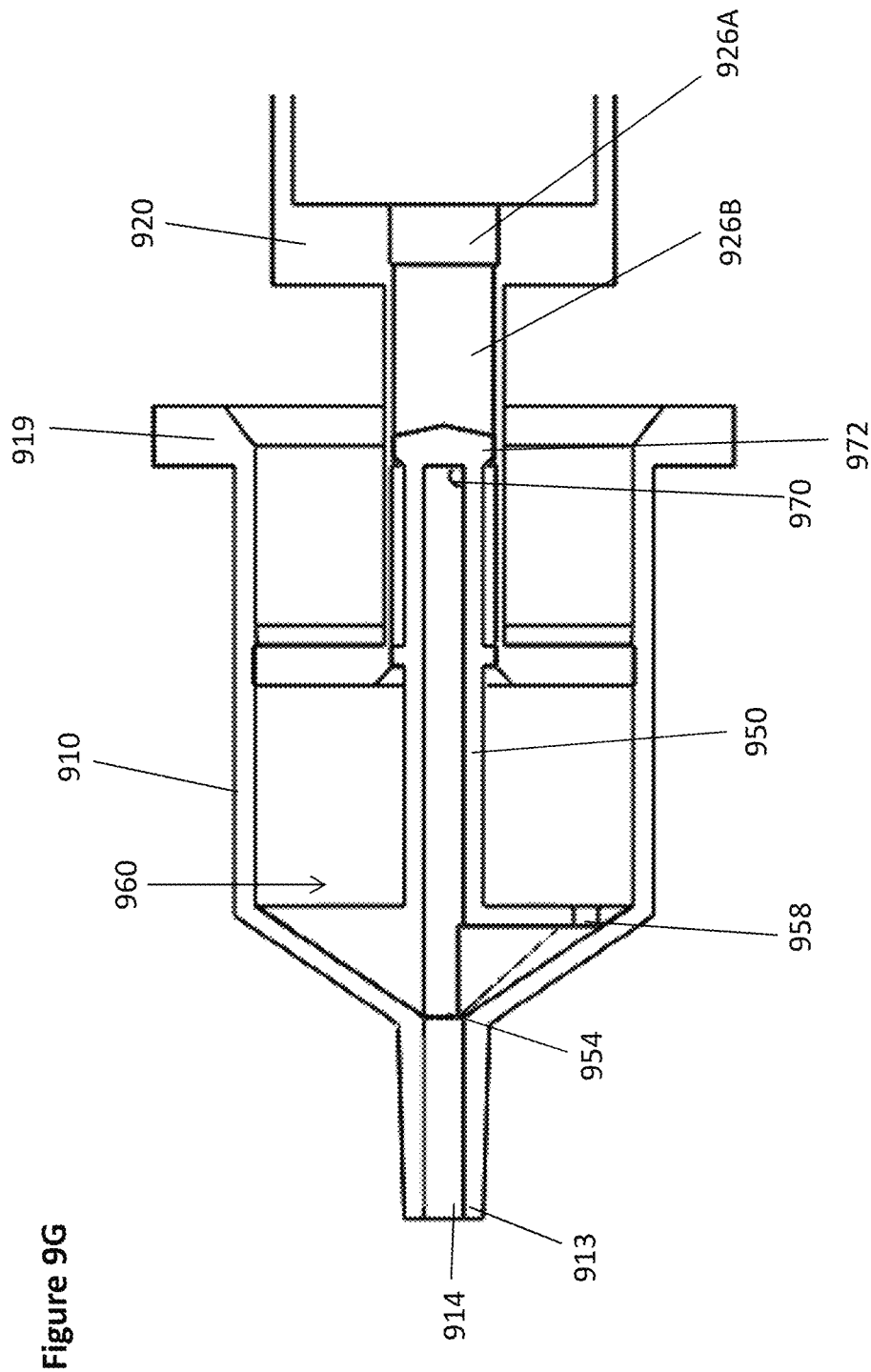
Figure 9H:
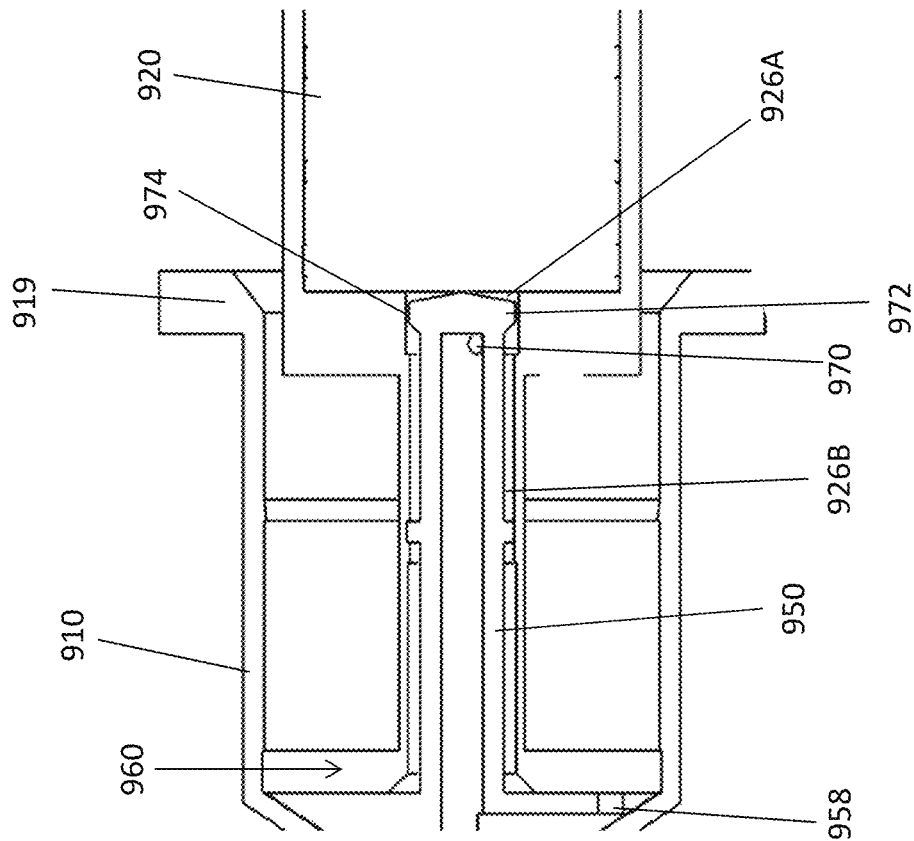

FIGS. 9F-9H show alternative embodiments of syringe 900 herein designated syringe 900'. Syringe 900' is structurally similar to syringe 900 but includes an additional flow safety mechanism for preventing mixing of the contents of first chamber 910 and second chamber 920. Mixing of the contents of first chamber 910 and second chamber 920 in syringe 900 is unlikely to occur due to the structure of syringe 900 but regulatory authorities may require such a flow safety mechanism as depicted in FIGS. 9F-9H for syringe 900'.

Inner tube 950 of syringe 900' comprises an upper port 970 for flow of fluids between inner tube 950 and second chamber 920 and an upper ring 972 for preventing or allowing flow of fluids between inner tube 950 and second chamber 920. The lower inner chamber 926 of second chamber 920 comprises a narrower portion 926B and a wider portion 926A.

As shown in FIG. 9G, when second chamber 920 is partially withdrawn from first chamber 910 but with upper ring 972 still engaging narrower portion 926B, no fluid can flow between inner tube 950 and second chamber 920.

As shown in FIG. 9H, when second chamber 920 is fully inserted from first chamber 910 such that upper ring 972 no longer engages narrower portion 926B, but rather sits within wider portion 926A, a gap 974 between upper ring 972 and wider portion 926A allows fluid to flow between inner tube 950 and second chamber 920 via upper port 970.

To further prevent mixing of contents of first chamber 910 and second chamber 920 in syringe 900', tube opening 954 is in direct fluid communication with adaptor tube 914 with no outlet chamber 956.

Figure 10A:
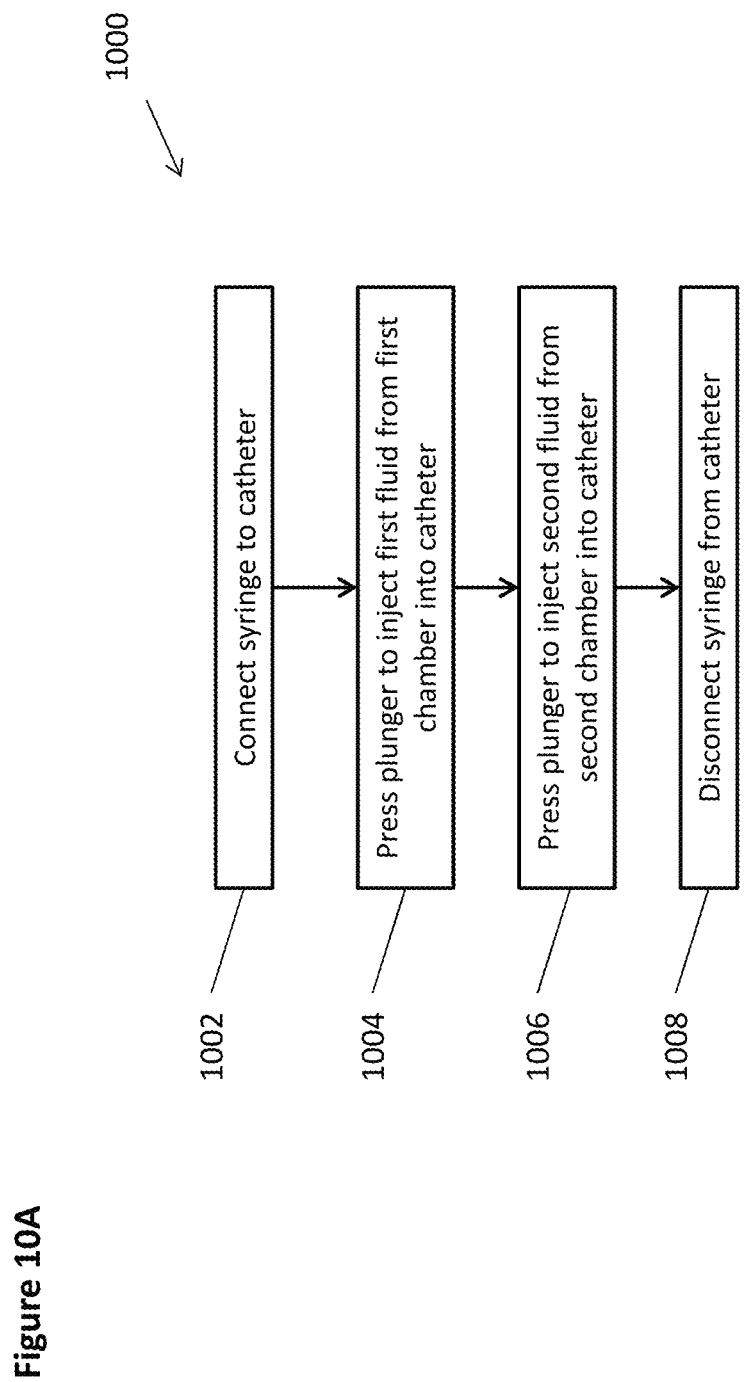
FIGS. 10A and 10B-10D are respectively a flow diagram and schematic illustrations showing operation of a syringe according to at least some embodiments of the present disclosure.
Figure 10B:
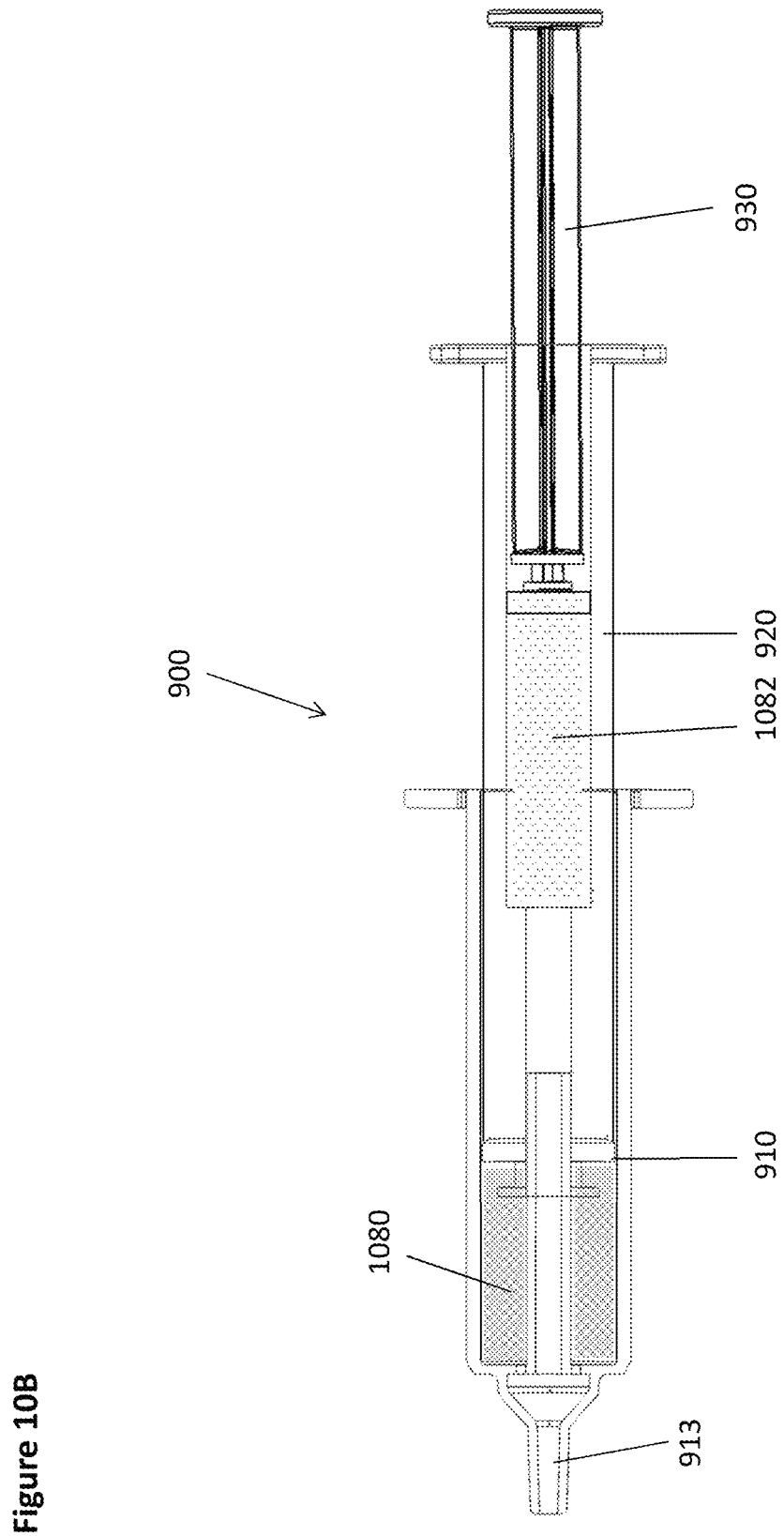

Reference is now made to FIGS. 10A and 10B-10D which are respectively a flow diagram and schematic illustrations showing operation of a syringe according to at least some embodiments of the present disclosure. The process 1000 of FIGS. 10A-10D relates to any process requiring consecutive injection of two different fluids such as but not limited to dialysis disconnection. As shown in FIG. 10B, the syringe 900 of FIG. 9A is provided with first chamber 910 filled with a first fluid 1080 for injection and second chamber 920 is filled with a second fluid 1082 for injection. Plunger 930 is partially inserted into second chamber 920. Syringe 900 is shown ready for use in FIG. 10B. Alternatively syringe 900' of FIGS. 9F-9H may be used for process 1000.

Plunger stopper 925 sealably engages the inner walls 916 of first chamber 910 and second chamber 920 thus functions as a syringe plunger for first chamber 910. Plunger head 932 sealably engages the inner walls 927 of second chamber 920 and thus plunger 930 functions as a syringe plunger for second chamber 920.

Figure 10C:
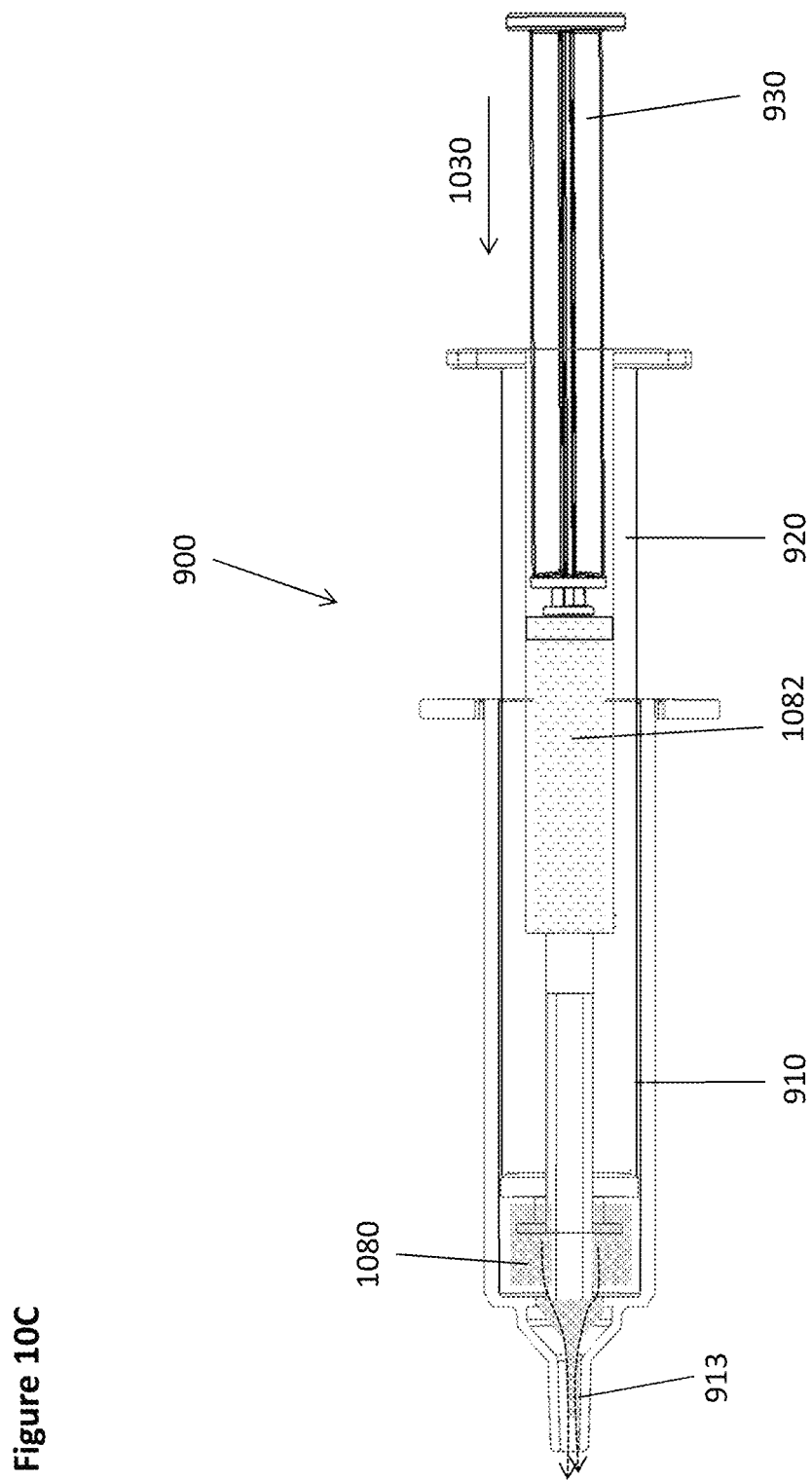

In step 1002, syringe 900 is connected at adaptor tip 915 to a catheter (not shown). In step 1004, as shown in FIG. 10C, plunger 930 is pushed inwards in the direction as shown by arrow 1030. Since the force needed to move plunger 930 inside second chamber 920 is higher than the force required to move second chamber 920 into first chamber 910, due to the diameter difference ratio as described above, pushing on plunger 930 results in second chamber 920 moving into first chamber 910. Additionally, optional ridge 964 provides further resistance against stopper 931 moving further into second chamber 920.

First fluid 1080 is therefore forced out of first chamber 910 through ports 958, through outlet chamber 956, and through adaptor tube 914 into the catheter (not shown). At the end of step 1004, first chamber 910 has therefore been emptied and second chamber 920 remains filled with second fluid 1082.

Figure 10D:
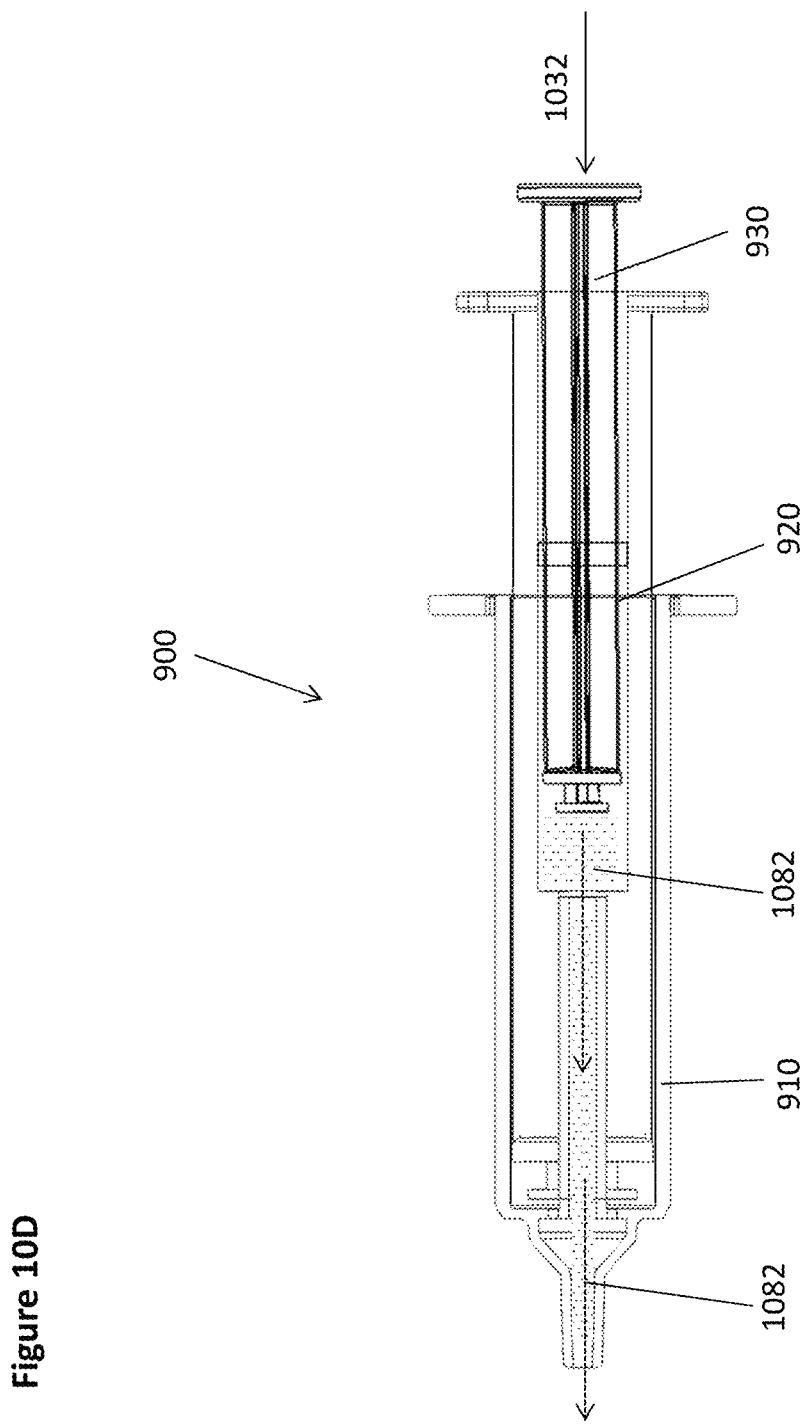

In step 1006, as shown in FIG. 10D the second fluid 1082 in second chamber 920 is injected into the catheter. Plunger 930 is depressed in the direction as shown by arrow 1032. Since second chamber 920 is pushed against base 952 of first chamber 910, plunger overcomes the resistance to movement and/or additionally the resistance of optional ridge 964 and starts to descend into second chamber 920. Plunger stopper 931 is sealably engaged with the upper inner walls 927 of second chamber 920 creating positive pressure and pushing the second fluid 1082 out of second chamber 920 through lower inner chamber 926, through inner tube 950, through opening 954, through outlet chamber 956, and through adaptor tube 914 into the attached catheter (not shown). When plunger stopper 931 reaches the bottom of upper inner chamber 927, it can no longer be pushed any further. At the end of step 1006, both first chamber 910 and second chamber 920 are emptied of, respectively, first fluid 1080 and second fluid 1082.

In step 1008 the syringe 900 is disconnected from the catheter and is preferably discarded. It should be appreciated that syringe 900 and process 1000 can be used for any situation requiring consecutive injection of two separate fluids into the same receptacle.

Figure 11A:
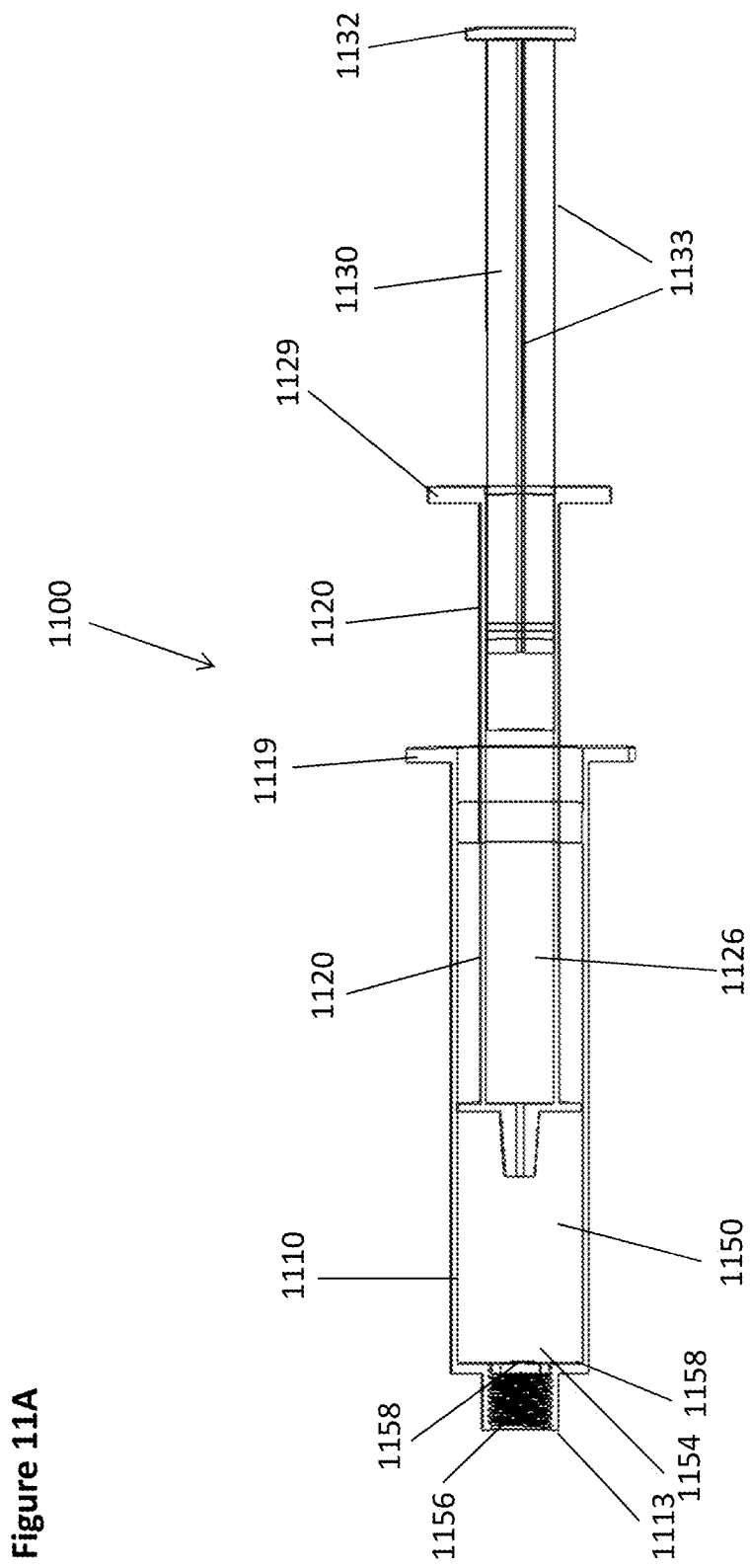
Figure 11C:
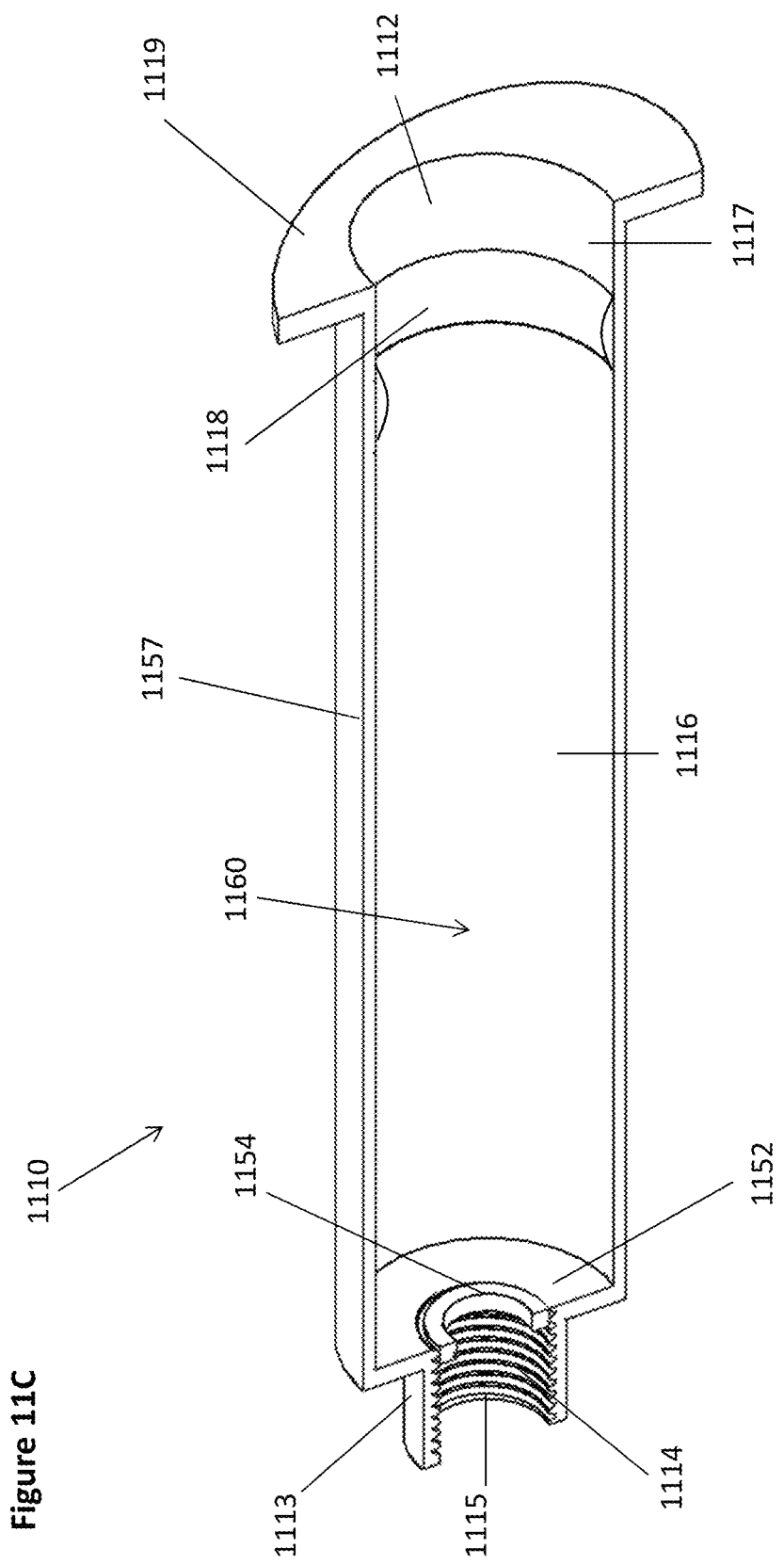
Figure 11D:
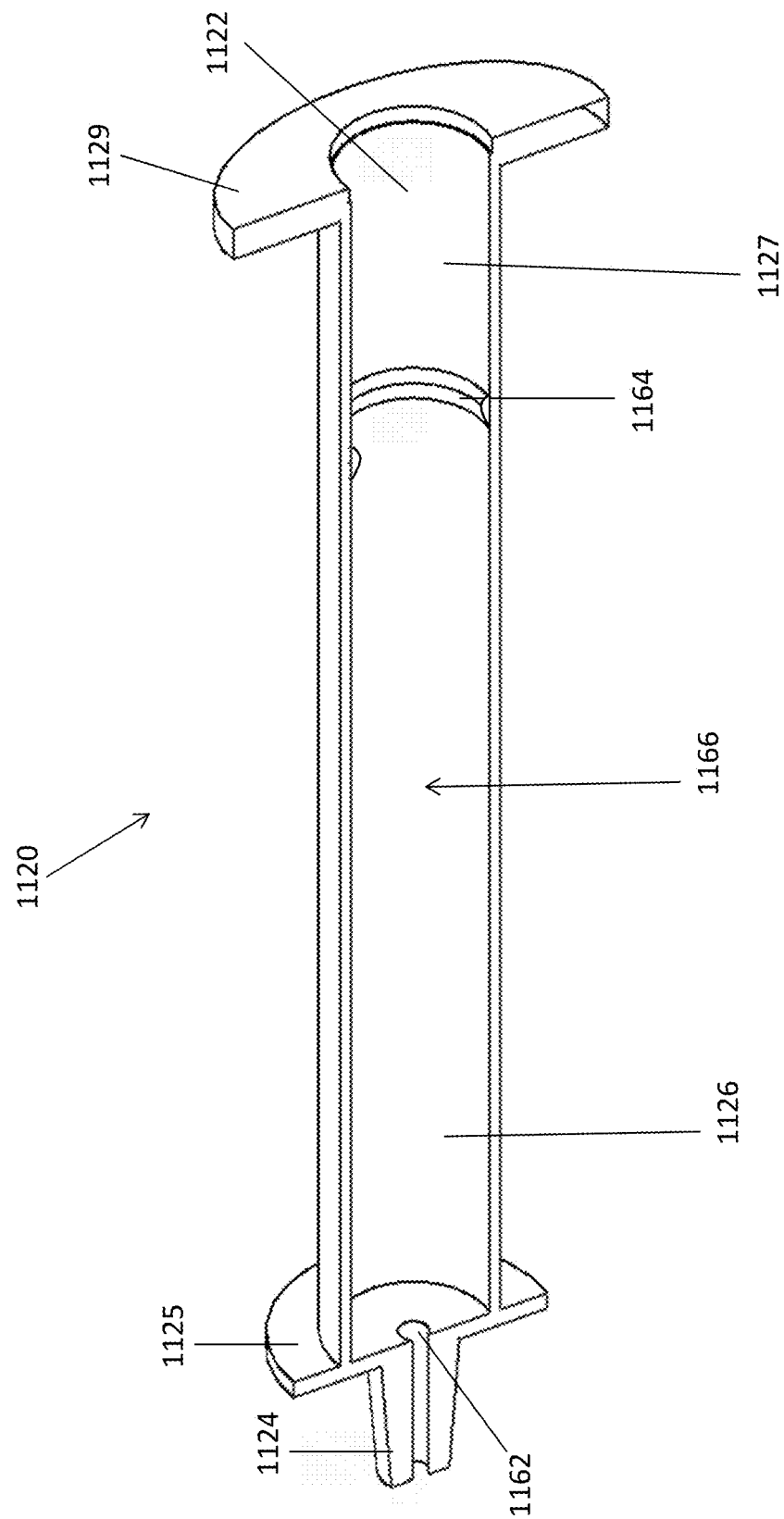

Reference is now made to FIGS. 11A-11D which are schematic illustrations of a syringe according to at least some embodiments of the present disclosure. As shown in FIG. 11A, a syringe 1100 comprises a first chamber 1110, second chamber 1120, and plunger 1130.

First chamber 1110 is a cylindrical hollow chamber open at opening 1112 at chamber flange 1119. First chamber 1110 comprises an opening 1154 in base 1152 at the lower end of first chamber 1110. Tube opening 1154 provides for fluid communication between inner volume 1160 of first chamber 1110 and adaptor tube 1114.

First chamber 1110 comprises ridge 1118 to prevent removal of inserted second chamber 1120. Additionally, first chamber 1110 is preferably tapered as known in the art on its upper inner surface 1117 near opening 1112 to provide greater resistance and prevent easy removal of inserted second chamber 1120.

First chamber 1110 comprise adaptor 1113 for attachment to a catheter (not shown) or other medical device (not shown). Adaptor 1113 comprises adaptor tube 1114 which is open at adapter tip 1115. Adaptor tube 1114 is optionally threaded to enable attachment of syringe 1100 to receptacles such as but not limited to catheters. Adaptor 1113 has dimensions of syringe adaptors as known in the art including but not limited to Luer Lock tapered termination.

Second chamber 1120 is a cylindrical hollow chamber open at opening 1122 at chamber flange 1129. Second chamber 1120 comprises plunger stopper 1125. Stopper 1125 is sized so as to firmly engage the inner surfaces 1117 and 1116 of first chamber 1110. Stopper 1125 comprises rubber, silicone or other material known in the art for use in syringe plunger stoppers. Second chamber 1120 is open at opening 1162 in a bottom end of second chamber 1120 where opening 1162 extends through connector tube 1124 for providing fluid communication between the inner volume 1166 of second chamber and adaptor tube 1114 when second chamber 1120 is fully inserted into first chamber 1110.

The circumference of inner wall 1126 of second chamber 1120 is fixed along the majority of its length so as to engage stopper 1125. Inner upper wall 1127 is tapered at its rear end as is known in the art such that plunger 1130 cannot be easily pulled out. Second chamber 1120 further comprises ridge 1164 to provide resistance for insertion of plunger 130.

Plunger 1130 is formed as a typical plunger as known in the art. The body of plunger 1130 comprises up to four parallel blades 1133 running the length of plunger 1130. Alternatively more blades 1133 or no blades are provided. Plunger stopper 1131 is affixed to the front of plunger 1130. Stopper 1131 is sized so as to sealably engage the inner walls 1127 and 1126 of second chamber 1120. Plunger 1130 comprises a plunger head 1132 at its rear end formed for pushing plunger 1130 into second chamber 1120.

Stopper 1125 has a diameter that is slightly bigger than the diameter at inner surfaces 1117 and 1116 such that stopper 1125 sealably engages surfaces 1116 and 1117 preventing fluid from escaping around stopper 1125 while allowing stopper 1125 to move along surfaces 1116 and 1117. The "first chamber diameter difference" of stopper 1125 to the diameter at surfaces 1117 and 1116 is optionally up to 1% bigger.

Plunger stopper 1131 has a diameter that is slightly bigger than the inner walls 1127 and 1126 of second chamber 1120 such that stopper 1131 sealably engages surfaces 1126 and 1127 preventing fluid from escaping around stopper 1131 while allowing stopper 1131 to move along surfaces 1126 and 1127. The "second chamber diameter difference" of stopper 1131 to the diameter at surfaces 1127 and 1126 is optionally up to 3% bigger.

Moving stopper 1131 inside second chamber 1120 therefore requires greater effort than moving stopper 1125 inside first chamber 1110 since stopper 1131 has a higher diameter difference than stopper 1125. The "diameter difference ratio" of first chamber diameter difference to second chamber diameter difference is preferably 1:3. The diameter difference ratio of first chamber diameter difference to second chamber diameter difference is optionally 1:4.

Figure 12A:
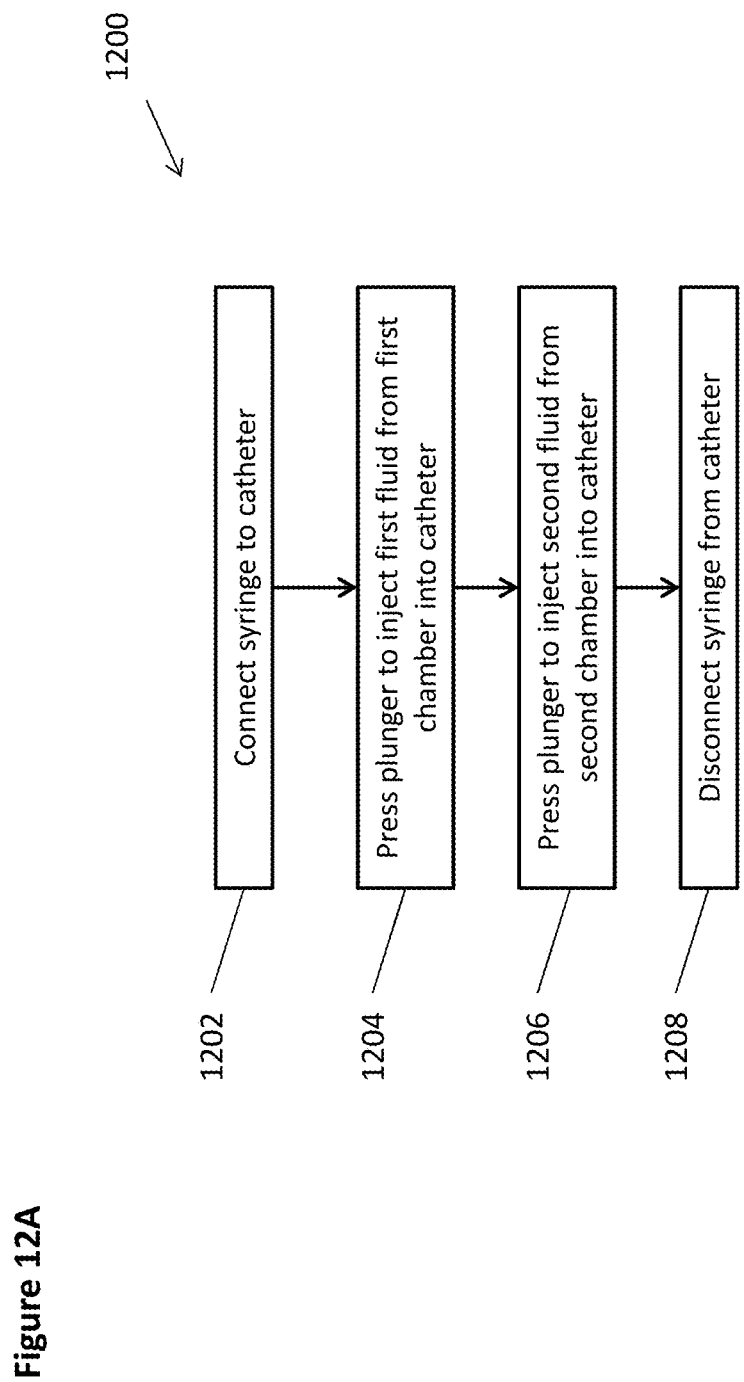
FIGS. 12A and 12B-12D are respectively a flow diagram and schematic illustrations showing operation of a syringe according to at least some embodiments of the present disclosure.
Figure 12B:
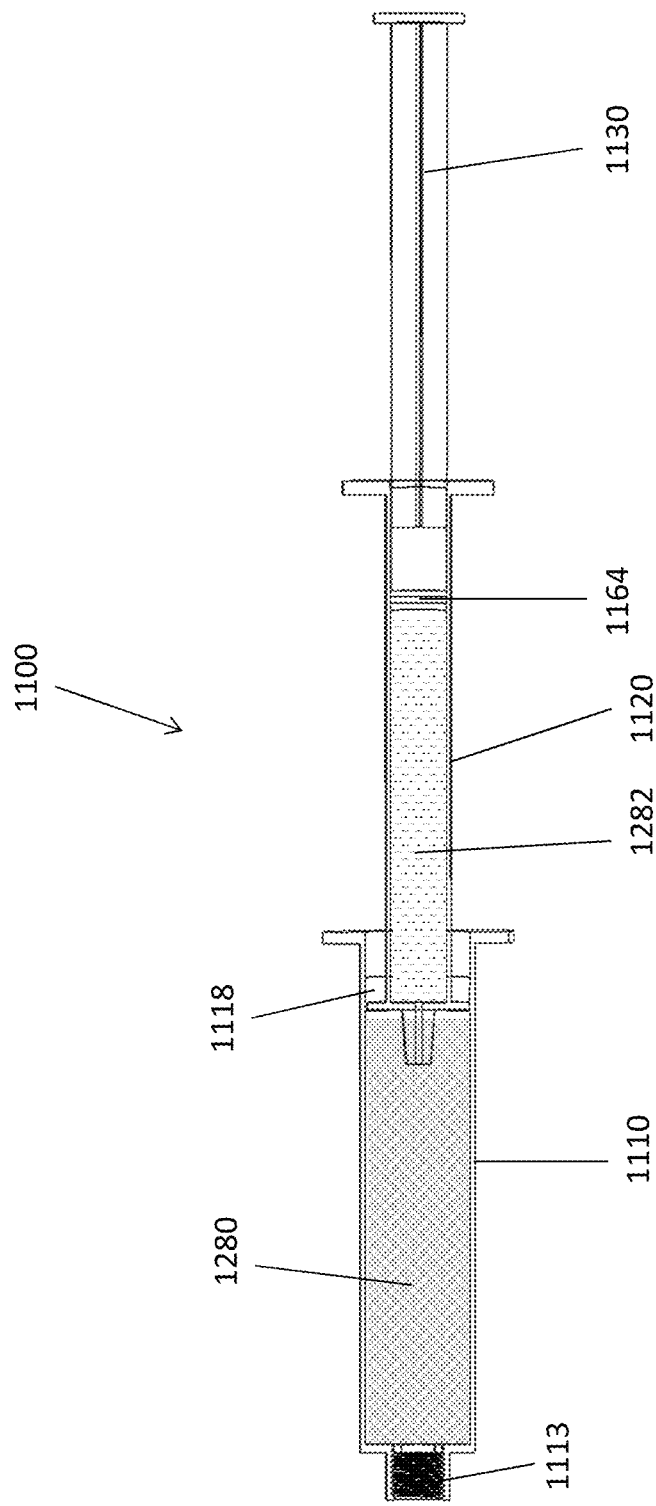

Reference is now made to FIGS. 12A and 12B-12D which are respectively a flow diagram and schematic illustrations showing operation of a syringe according to at least some embodiments of the present disclosure. The process 1200 of FIGS. 12A-12D relates to any process requiring consecutive injection of two different fluids. As shown in FIG. 12B, the syringe 1100 of FIG. 11A is provided with first chamber 1110 filled with a first fluid 1280 for injection and second chamber 1120 is filled with a second fluid 1282 for injection. Second chamber 1120 is partially inserted into first chamber 1110 with stopper 1125 past ridge 1118 and plunger 1130 is partially inserted into second chamber 1120 before ridge 1164. Syringe 1100 is shown ready for use in FIG. 12B.

Plunger stopper 1125 sealably engages the inner walls 1117 and 1116 of first chamber 1110 and second chamber 1120 thus functions as a syringe plunger for first chamber 1110. Plunger head 1132 sealably engages the inner walls 1126 and 1127 of second chamber 1120 and plunger 1130 thus functions as a syringe plunger for second chamber 1120.

Figure 12C:
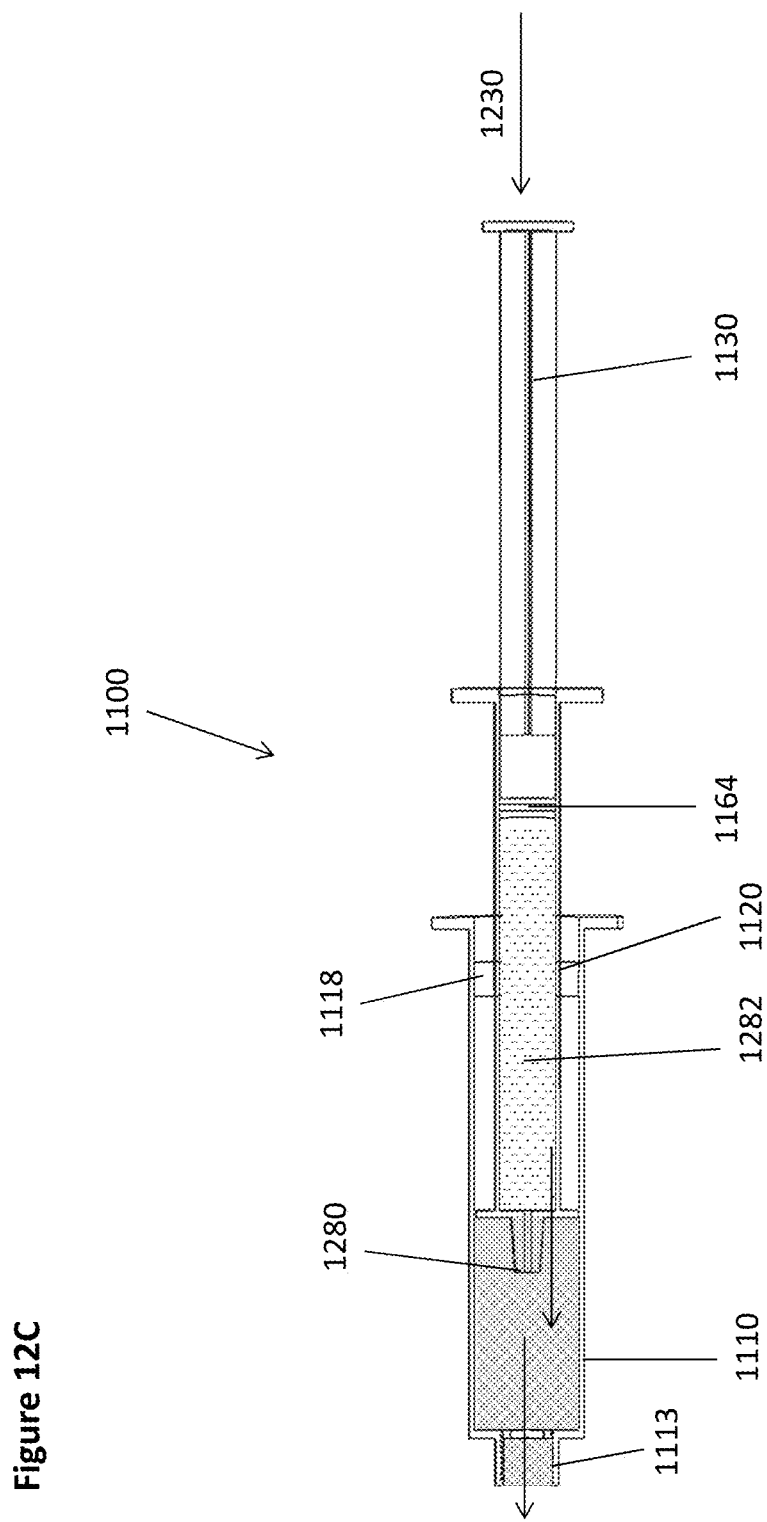

In step 1202, syringe 1100 is connected at adaptor 1113 to a catheter (not shown). In step 1204, as shown in FIG. 12C, plunger 1130 is pushed inwards in the direction as shown by arrow 1230. Since the force needed to move plunger 1130 inside second chamber 1120 is higher than the force required to move second chamber 1120 into first chamber 1110, due to the diameter difference ratio as described above, pushing on plunger 1130 results in second chamber 1120 moving into first chamber 1110. Additionally, ridge 1164 provides further resistance against stopper 1131 moving further into second chamber 1120.

First fluid 1280 is therefore forced out of first chamber 1110 through adaptor tube 1114 into the catheter (not shown). At the end of step 1204, first chamber 1110 has therefore been emptied, second chamber 1120 remains filled with second fluid 1282 and second chamber 1120 is pressed against base 1152 of first chamber 1110 such that connector tube 1124 is inserted into adaptor tube 1114.

Figure 12D:
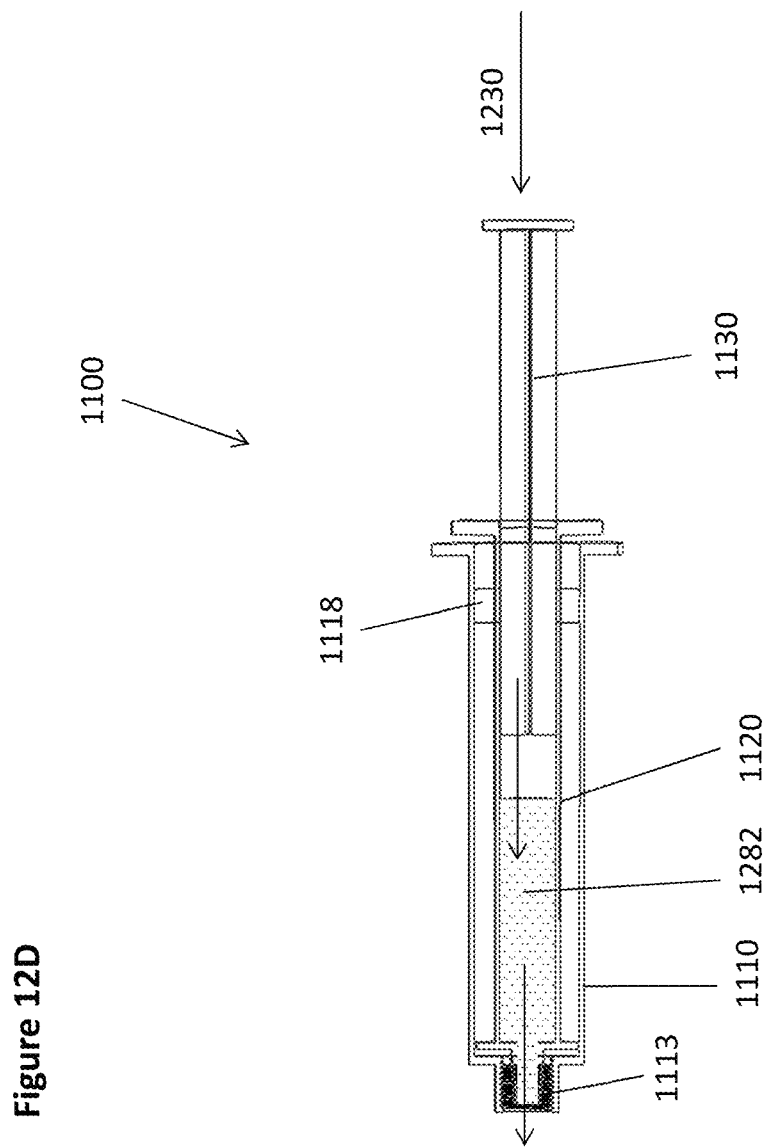

In step 1206, as shown in FIG. 12D second fluid 1282 in second chamber 1120 is injected into the catheter. Plunger 1130 continues to be pressed in the direction as shown by arrow 1230. Since second chamber 1120 is pushed against base 1152 of first chamber 1110, plunger 1130 overcomes the resistance created by the diameter difference and also pushes past ridge 1164 and starts to descend into second chamber 1120. Plunger stopper 1131 thus pushes second fluid 1282 out of second chamber 1120 through opening 1162, through connector tube 1124, and through adaptor tube 1114 into the attached catheter (not shown). When plunger stopper 1131 reaches the bottom of second chamber 1120, it can no longer be pushed any further. At the end of step 1206, both first chamber 1110 and second chamber 1120 are emptied of, respectively, first fluid 1280 and second fluid 1282.

In step 1208 syringe 1100 is disconnected from the catheter and is preferably discarded. It should be appreciated that syringe 1100 and process 1200 can be used for any situation requiring consecutive injection of two separate fluids into the same receptacle.

Figure 13A:
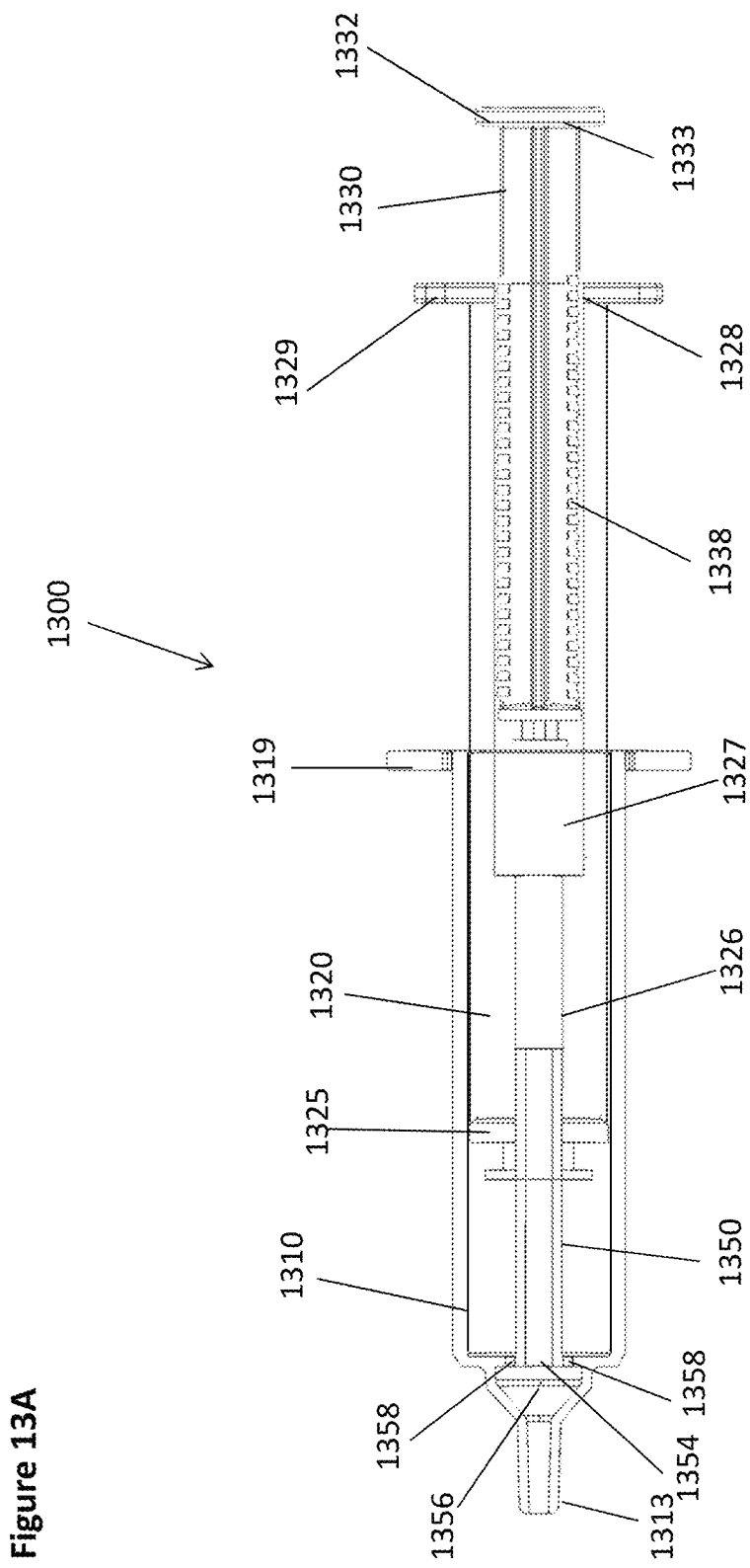
FIGS. 13A-13C are schematic illustrations of a syringe according to at least some embodiments of the present disclosure.
Figure 13B:
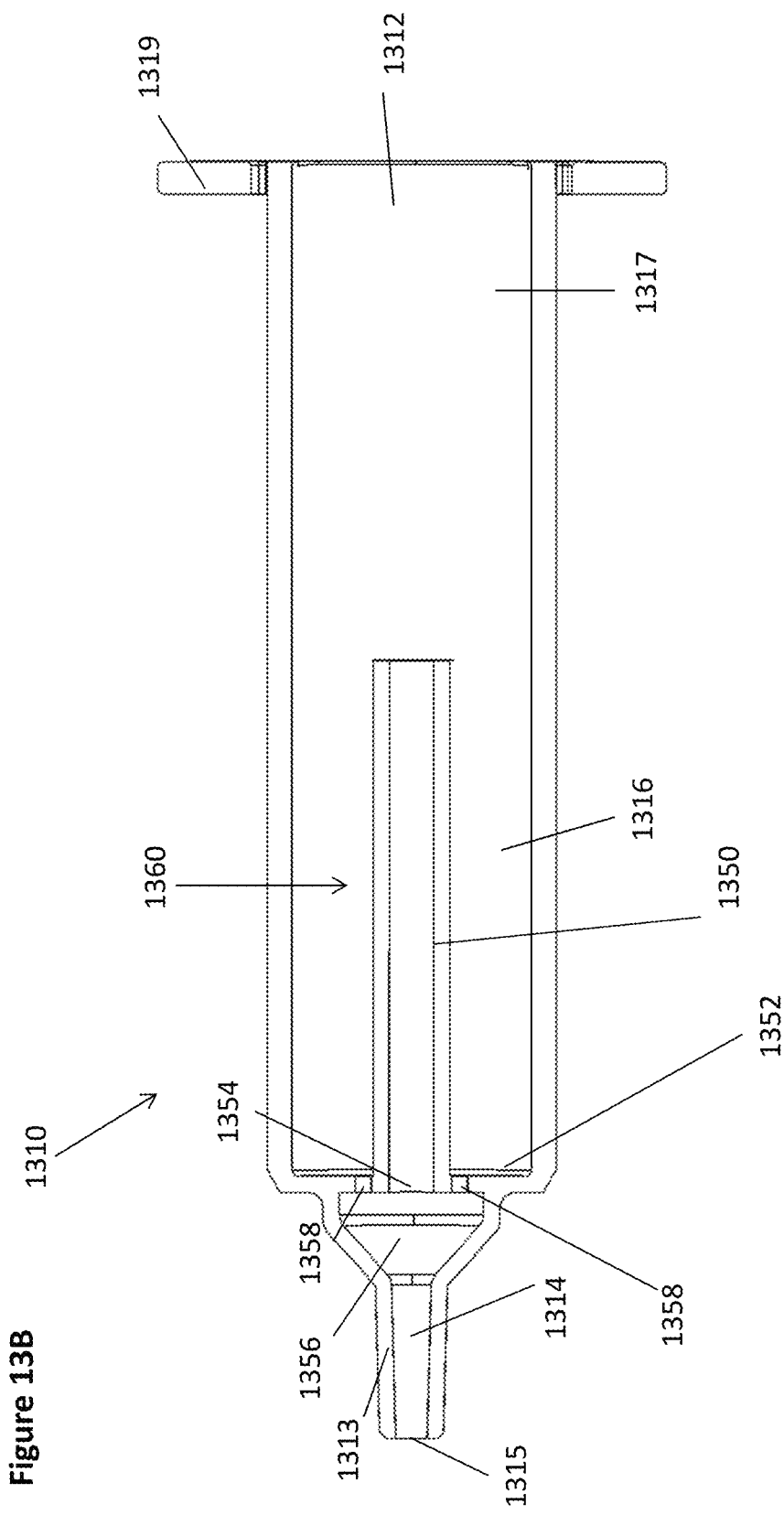
Figure 13C:
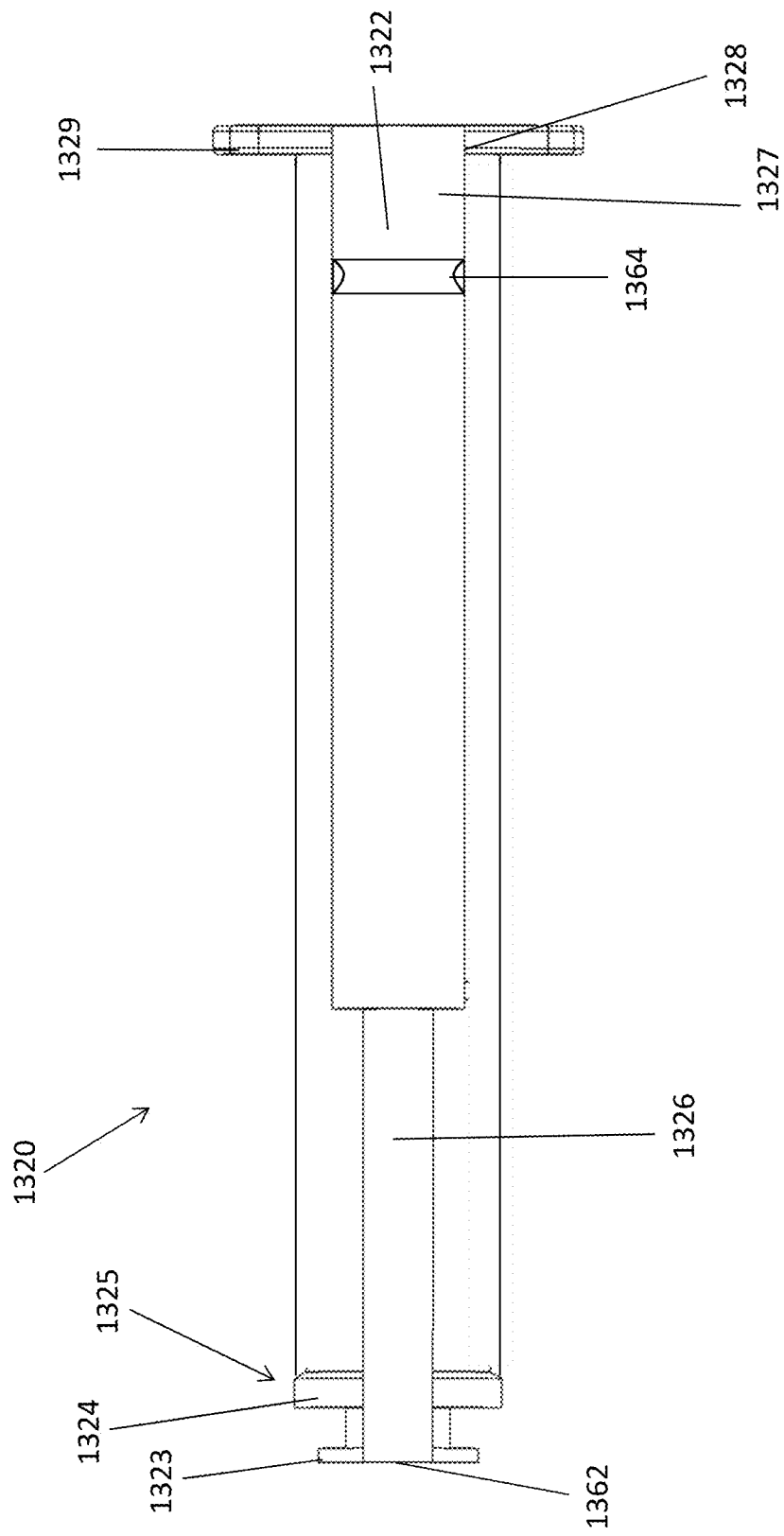

Reference is now made to FIGS. 13A-13C which are schematic illustrations of a syringe according to at least some embodiments of the present disclosure. As shown in FIG. 13A, a syringe 1300 comprises a first chamber 1310, second chamber 1320, and plunger 1330.

First chamber 1310 is a cylindrical hollow chamber open at opening 1312 at chamber flange 1319. First chamber 1310 comprises an inner tube 1350 extending from the base 1352 of first chamber 1310 and defining an opening 1354 in base 1352 at the lower end of the inner tube 1350. Tube opening 1354 provides for fluid communication between tube 1350 and outlet chamber 1356. Outlet chamber 1356 is in fluid communication with adaptor tube 1314.

Base 1352 further comprises a plurality of ports 1358 in base 1352 providing fluid communication between outlet chamber 1356 and the inner volume 1360 of first chamber 1310. As shown in FIG. 13A, base 1352 comprises two ports 1358 but this number should not be considered limiting and optionally more or less ports of the same or different sizes may be provided.

First chamber 1310 comprise adaptor 1313 for attachment to a catheter (not shown) or other medical device or receptacle (not shown). Adaptor 1313 comprises adaptor tube 1314 which is open at adapter tip 1315. Adaptor 1313 has dimensions of syringe adaptors as known in the art including but not limited to Luer Lock tapered termination.

Second chamber 1320 is a cylindrical hollow chamber open at opening 1322 at chamber flange 1329. Second chamber 1320 comprises leading ring 1323 and trailing ring 1324 of plunger stopper 1325. Leading ring 1323 is sized so as to seal ports 1358 when it makes contact with base 1352 by covering them. Trailing ring is sized so as to firmly engage the lower inner surface 1316 of first chamber 1310. Rings 1323, 1324 comprise rubber, silicone or other material known in the art for use in syringe plunger stoppers.

Second chamber 1320 is open at opening 1362 in a bottom end of second chamber 1320 where opening 1362 extends through plunger stopper 1325 so that second chamber 1320 can fit over inner tube 1350.

Chamber flange 1329 comprises notches 1328 for engaging with ratchet 1338 of plunger 1330.

Second chamber 1320 has a wider upper inner chamber 1327 and a narrower lower inner chamber 1326. Inner chamber 1326 is sized so as to sealably fit over inner tube 1350 when second chamber 1320 is placed inside of first chamber 1310. The diameter of second chamber 1320 is preferably tapered as known in the art on its upper inner surface 1327 near opening 1322 to provide greater resistance and prevent easy removal of inserted plunger 1330.

Plunger 1330 comprises linear ratchet 1338 for engaging with notch 1328 of second chamber 1320. The diameter of upper wall 1327 of second chamber 1320 is fixed along the majority of its length so as to engage plunger 1330. The diameter of inner upper wall 1327 is tapered at its rear end as is known in the art such that plunger 1330 cannot be easily pulled out.

Plunger 1330 is formed as a typical plunger as known in the art. The body of plunger 1330 comprises up to four parallel blades 1333 running the length of plunger 1330. Alternatively more blades or no blades are provided. Plunger stopper 1331 is affixed to the front of plunger 1330. Stopper 1331 is sized so as to sealably engage the inner upper wall 1327 of second chamber 1320. Plunger 1330 comprises a plunger head 1332 at its rear end formed for pushing plunger 1330 into second chamber 1320.

First chamber 1310 is preferably tapered as known in the art at the upper part of inner surface 1316 to provide greater resistance and prevent removal of inserted second chamber 1320. Linear ratchet 1338 preferably comprises a stop mechanism at its lower end to prevent removal of plunger 1330 from second chamber 1320. The stop mechanism may for example be a square tooth or opposite facing tooth on ratchet 1338 that cannot be pulled past notch 118.

Figure 14A:
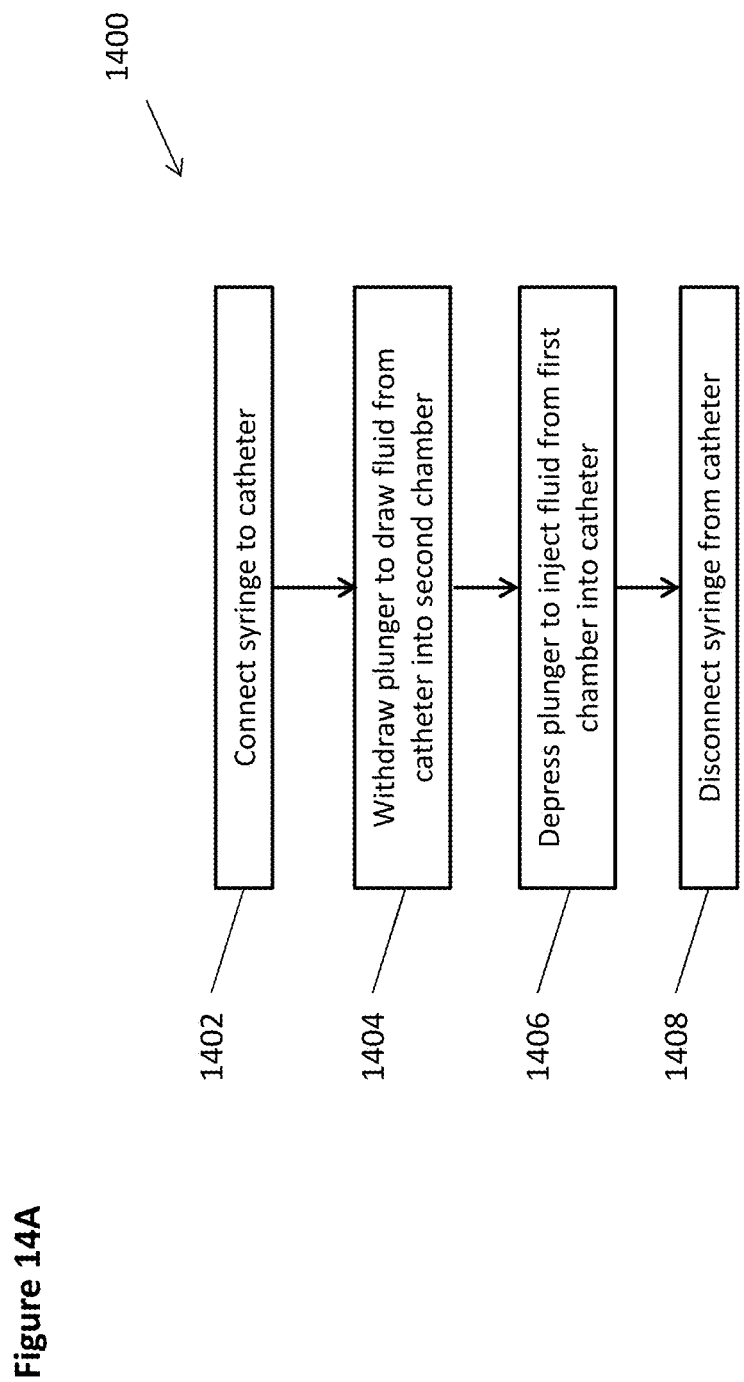
FIGS. 14A and 14B-14E which are respectively a flow diagram and schematic illustrations showing operation of a syringe according to at least some embodiments of the present disclosure
Figure 14B:
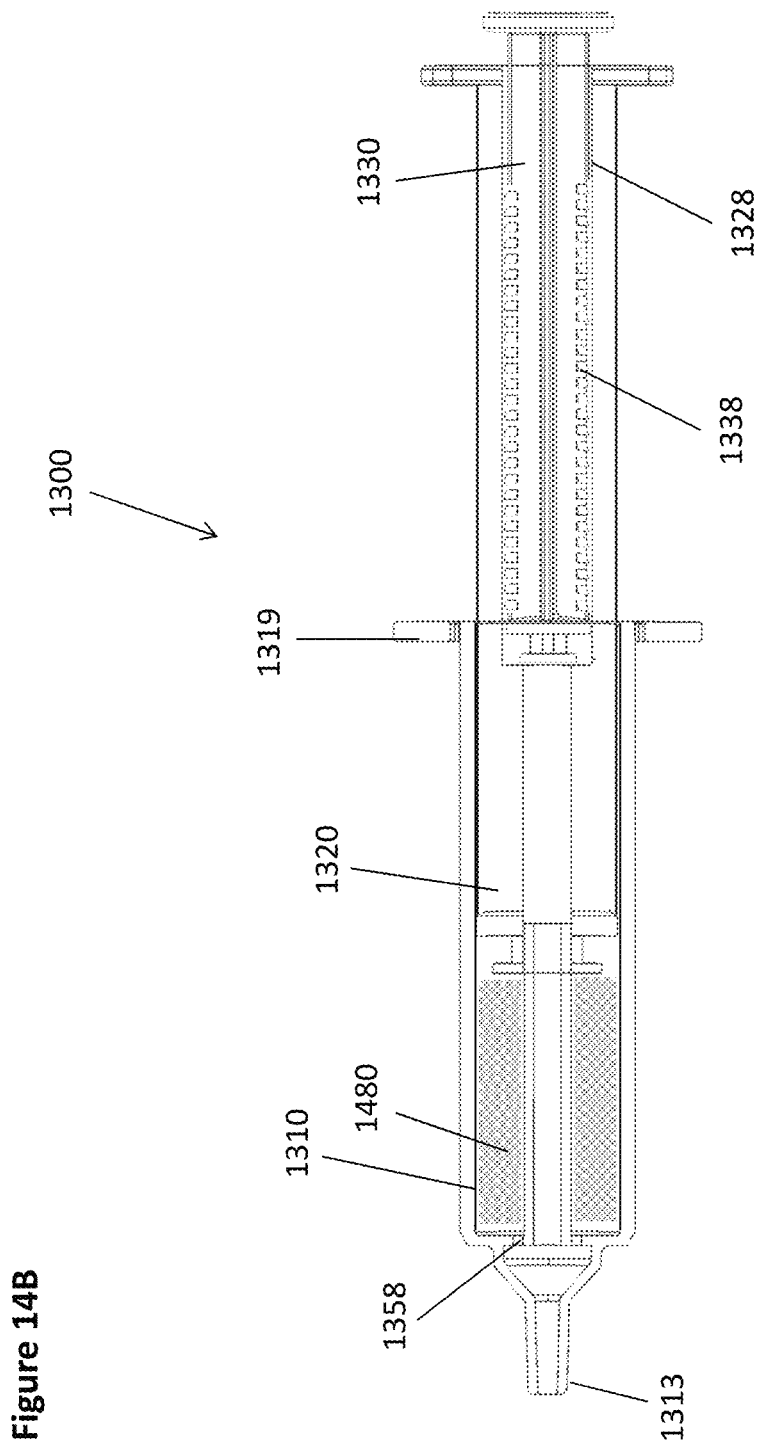
Figure 14C:
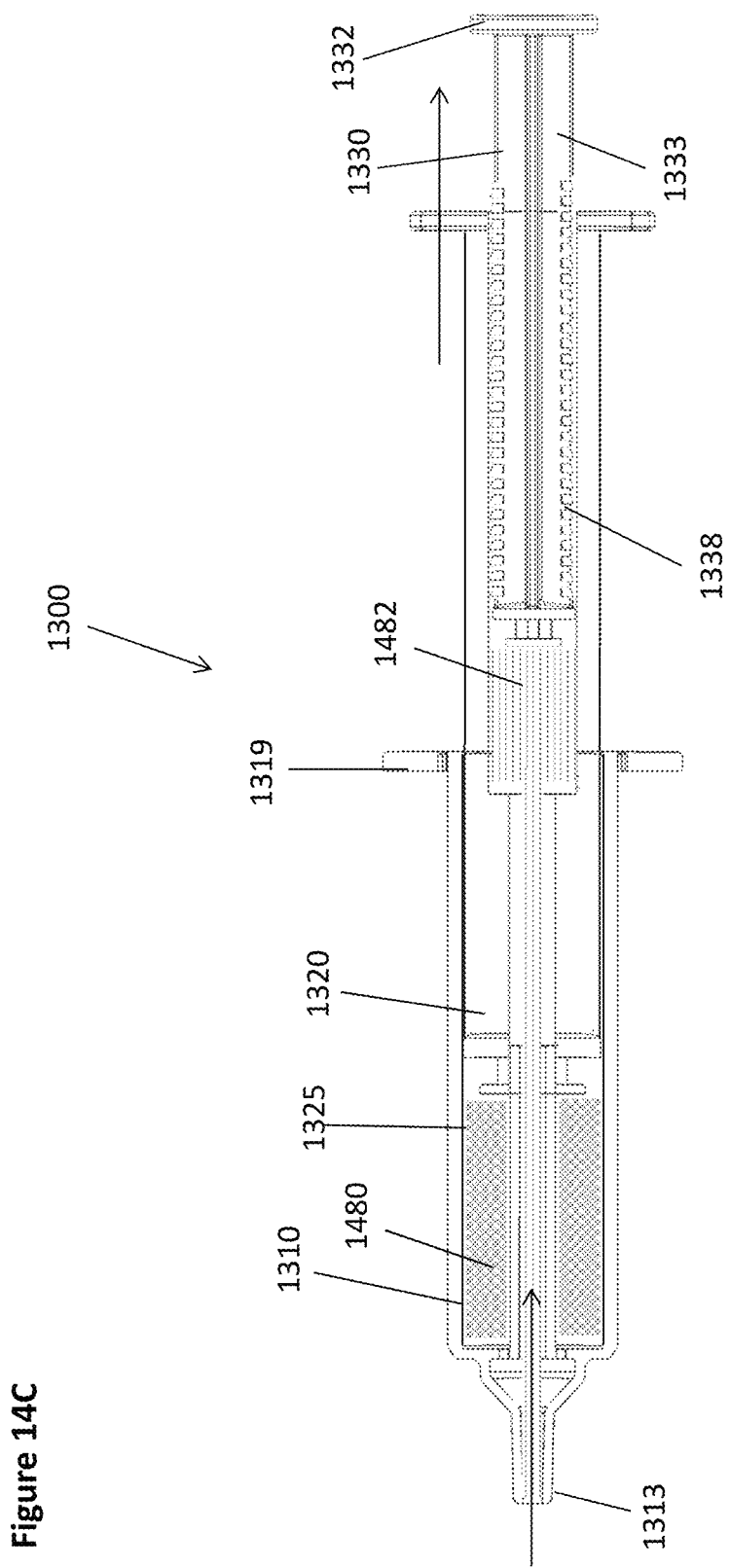
Figure 14D:
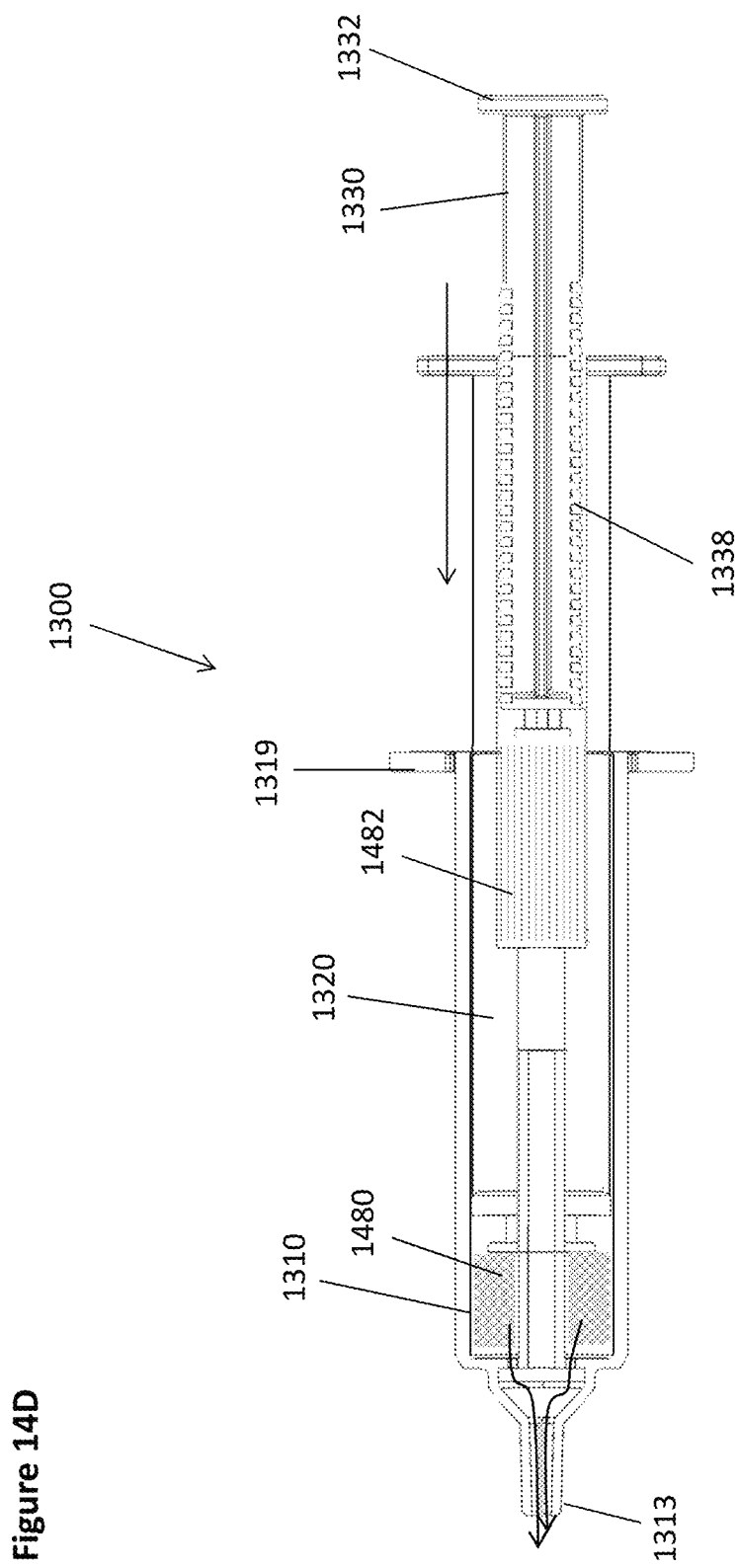
Figure 14E:
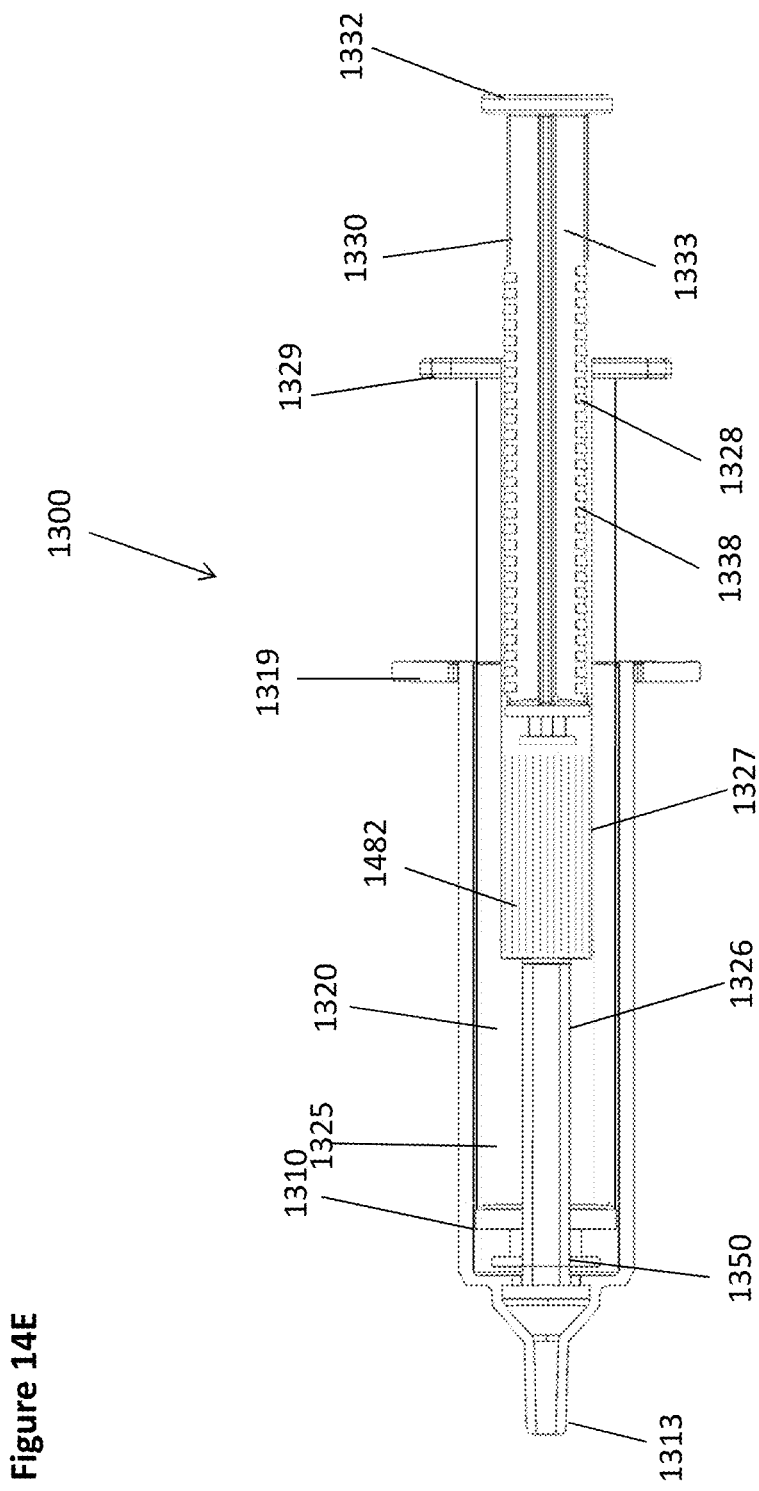

Reference is now made to FIGS. 14A and 14B-14E which are respectively a flow diagram and schematic illustrations showing operation of a syringe according to at least some embodiments of the present disclosure. The process 1400 of FIGS. 14A-14E relates to connection of a CVC (Central Venous Catheter) or any catheter or medical tube to a dialysis machine or any process requiring suction followed by injection of different fluids. As shown in FIG. 14B, the syringe 1300 of FIGS. 13A-13C is provided with plunger 1330 inserted fully into second chamber 1320 and second chamber partially inserted into first chamber 1310 where first chamber 1320 is pre-filled with physiological solution 1480 or other fluid 1480. Syringe 1300 is shown ready for use in FIG. 14B.

The functioning process 1400 of syringe 1300 is as for syringe 700 described above in process 800, but in step 1404 (FIG. 14C), following connection of a catheter in step 1402, plunger 1330 is withdrawn along ratchet 1338 to draw fluid 1482 from a catheter into second chamber 1320. Once sufficient fluid 1482 has been drawn, in step 1406, plunger 1330 is pressed (FIGS. 14D and 14E) and second chamber 1320 is pushed into first chamber 1310 to force the solution 1480 out of syringe 1300 via ports 1358, outlet chamber 1356 and adaptor tube 1314. In step 1408 syringe 1300 is preferably disconnected and discarded.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features and features or aspects of certain embodiments are also considered to be within the scope of some embodiments of the disclosure. For example, components or aspects of certain syringe embodiments described above may be utilized in other syringe embodiments even though not explicitly presented above.

While the disclosure has been described with respect to a limited number of embodiments, it will be appreciated that many variations, modifications and other applications of the disclosure may be made.

What is claimed is:

1. A nested syringe comprising:
   a first chamber including an inner tube, wherein the inner tube includes a port;
   a second chamber configured to fit into the first chamber and including a first inner chamber having first and second portions,
   wherein the first inner chamber is configured to fit over the inner tube,
   wherein the first portion is configured to prevent fluid flow through the port when the port is in the first portion, and wherein the second portion is configured to allow fluid flow through the port when the port is in the second portion.

2. The nested syringe of claim 1, wherein the first portion is narrower than the second portion.

3. The nested syringe of claim 1, further including a plunger configured to be inserted into the second chamber.

4. The nested syringe of claim 1, further including an adapter tube, wherein the inner tube extends from a base of the first chamber and defines an opening in the base, and wherein the adapter tube is in fluid communication with the inner tube via the opening.

5. The nested syringe of claim 2, wherein the first portion is positioned between the second portion and a second inner chamber of the second chamber.

6. The nested syringe of claim 2, wherein the second portion is positioned between the first portion and a second inner chamber of the second chamber.

7. The nested syringe of claim 5, configured such that the port is in the first portion when the second chamber is fully inserted into the first chamber.

8. The nested syringe of claim 6, configured such that the port is in the second portion when the second chamber is fully inserted into the first chamber.

9. The nested syringe of claim 4, wherein the base includes a base port providing fluid communication between the adapter tube and a first chamber inner volume.

* * * * *